United States Patent
Hu et al.

(10) Patent No.: US 10,730,858 B2
(45) Date of Patent: Aug. 4, 2020

(54) LACTAM, CYCLIC UREA AND CARBAMATE, AND TRIAZOLONE DERIVATIVES AS POTENT AND SELECTIVE ROCK INHIBITORS

(71) Applicant: BRISTOL-MYERS SQUIBB COMPANY, Princeton, NJ (US)

(72) Inventors: Zilun Hu, Jamison, PA (US); Cailan Wang, New Hope, PA (US); Mimi L. Quan, Yardley, PA (US); Peter W. Glunz, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/315,674

(22) PCT Filed: Jul. 6, 2017

(86) PCT No.: PCT/US2017/040846
§ 371 (c)(1),
(2) Date: Jan. 7, 2019

(87) PCT Pub. No.: WO2018/009622
PCT Pub. Date: Jan. 11, 2018

(65) Prior Publication Data
US 2019/0300510 A1    Oct. 3, 2019

Related U.S. Application Data

(60) Provisional application No. 62/359,341, filed on Jul. 7, 2016.

(51) Int. Cl.
| | |
|---|---|
| C07D 403/10 | (2006.01) |
| C07D 403/14 | (2006.01) |
| C07D 405/14 | (2006.01) |
| C07D 487/04 | (2006.01) |
| C07D 495/04 | (2006.01) |
| C07D 401/14 | (2006.01) |
| C07D 413/10 | (2006.01) |
| C07D 413/14 | (2006.01) |
| C07D 417/14 | (2006.01) |
| C07D 401/10 | (2006.01) |

(52) U.S. Cl.
CPC ......... C07D 403/10 (2013.01); C07D 401/10 (2013.01); C07D 401/14 (2013.01); C07D 403/14 (2013.01); C07D 405/14 (2013.01); C07D 413/10 (2013.01); C07D 413/14 (2013.01); C07D 417/14 (2013.01); C07D 487/04 (2013.01); C07D 495/04 (2013.01)

(58) Field of Classification Search
CPC .. C07D 403/10; C07D 403/14; C07D 405/14; C07D 487/04; C07D 417/14; C07D 495/04; C07D 413/14; C07D 413/10; C07D 401/10; C07D 401/14
See application file for complete search history.

(56) References Cited

U.S. PATENT DOCUMENTS

2014/0206686 A1*    7/2014    Glunz ................. C07D 401/10
514/234.5

FOREIGN PATENT DOCUMENTS

| WO | WO2006036981 A2 | 4/2006 |
|---|---|---|
| WO | WO2014134391 A1 | 9/2014 |
| WO | WO2014113620 A3 | 10/2014 |
| WO | WO2014169843 A1 | 10/2014 |
| WO | WO2015002915 A1 | 1/2015 |
| WO | WO2015002926 A1 | 1/2015 |
| WO | WO2016010950 A1 | 1/2016 |
| WO | WO2016028971 A1 | 2/2016 |
| WO | WO2016112236 A1 | 7/2016 |

(Continued)

OTHER PUBLICATIONS

Demirayak, et al., "Some Pyridazinone and Phthalazinone Derivatives and Their Vasodilator Activities", Arch Pharm Res., vol. 27(1), pp. 13-18 (2004).

(Continued)

*Primary Examiner* — Alexander R Pagano
*Assistant Examiner* — Ebenezer O Sackey
(74) *Attorney, Agent, or Firm* — Hong Liu

(57) ABSTRACT

The present invention provides compounds of Formula (I): Formula (I) or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

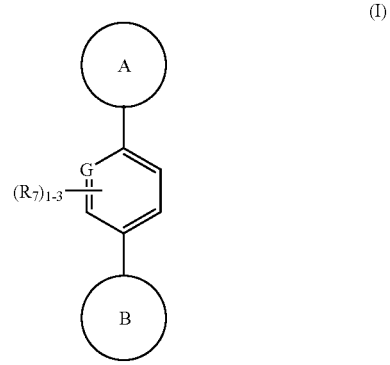

14 Claims, No Drawings
Specification includes a Sequence Listing.

(56) References Cited

FOREIGN PATENT DOCUMENTS

| WO | WO2016144936 A1 | 9/2016 |
| WO | WO2017123860 A1 | 7/2017 |
| WO | WO2017205709 A1 | 11/2017 |
| WO | WO2018009625 A1 | 1/2018 |
| WO | WO2018009627 A1 | 1/2018 |
| WO | WO2018102325 A1 | 6/2018 |

OTHER PUBLICATIONS

Wasfy, et al., "An efficient synthesis of some new 1,4-disubstituted phthalazine derivatives and their anticancer activity", Der Pharma Chemica, vol. 5(2), pp. 82-96 (2013).

\* cited by examiner

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: FITC-AHA at N Terminus attached at A1 - A11
<220> FEATURE:
<221> NAME/KEY: MISC_FEATURE
<223> OTHER INFORMATION: OH at C Terminus attached at A1 - A11

<400> SEQUENCE: 1

Ala Lys Arg Arg Arg Leu Ser Ser Leu Arg Ala
1               5                   10
```

LACTAM, CYCLIC UREA AND CARBAMATE, AND TRIAZOLONE DERIVATIVES AS POTENT AND SELECTIVE ROCK INHIBITORS

CROSS REFERENCE TO RELATED APPLICATIONS

This application is a 371 application of PCT/US2017/040846 filed Jul. 6, 2017 which is entitled to priority pursuant to 35 U.S.C. § 119(e) to U.S. provisional patent application No. 62/359,341, filed Jul. 7, 2016, which is incorporated herein in its entirety.

FIELD OF THE INVENTION

The present invention relates to novel lactam, cyclic urea and carbamate, and triazolone derivatives, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example, angiotensin II (Yamakawa, T. et al., *Hypertension*, 35:313-318 (2000)), urotension II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. 1*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vase. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol. Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol. Sci.*, 13:8293-8307 (2012); Zhou, L. et al., *Am. J. Nephrol.*, 34:468-475 (2011)), as well as neurological disorders, such as spinal-cord injury, Alzheimer disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010 ~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2008/0275062 A1), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel lactam, cyclic urea and carbamate, and triazolone derivatives including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

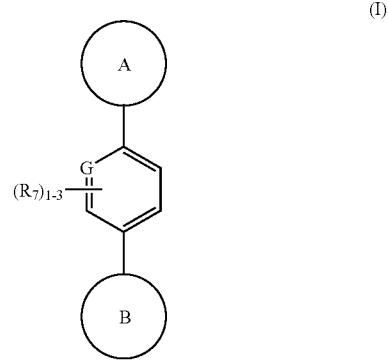

or stereoisomers, enantiomers, diastereoisomers, tautomers, pharmaceutically acceptable salts, solvates, or prodrugs thereof, wherein
Ring A is independently selected from

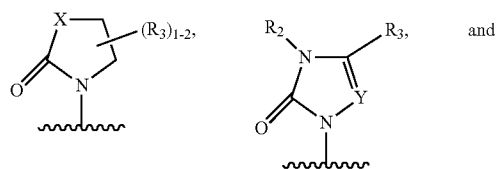

-continued

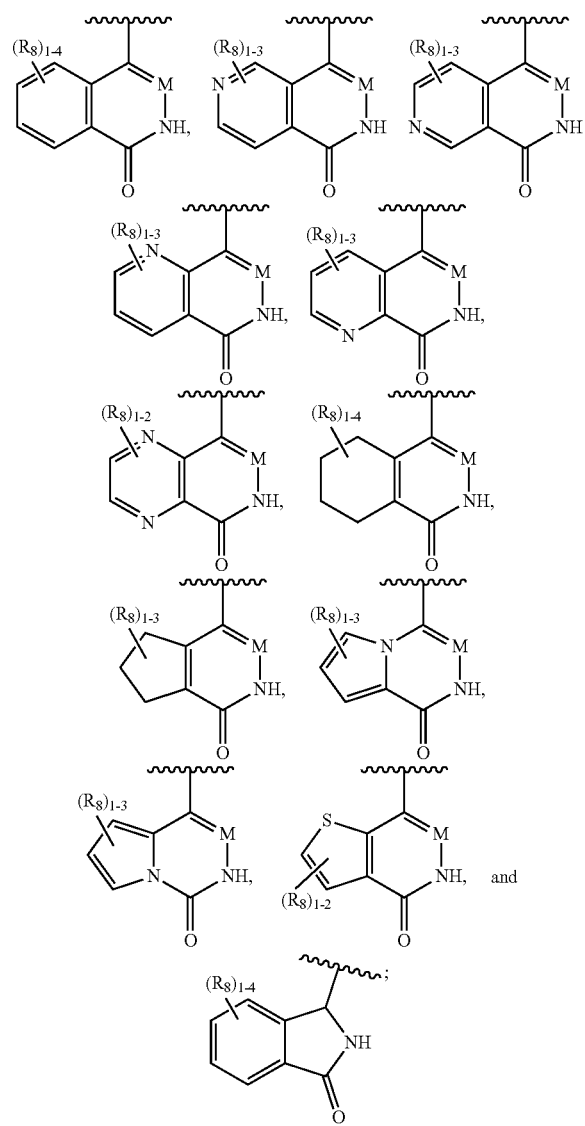

Ring B is independently selected from

G is independently selected from N and $CR_7$;
M is independently selected from N and $CR_9$;
X is independently selected from $CR_1$, $NR_2$, and O;
Y is independently selected from $CR_3$ and N;
L is absent or independently selected from —$NR_4$—, —C(O)$NR_4$($CR_4R_4$)$_n$—, and —O—;
$R_1$ is L-$R_5$;
$R_2$ is —($CR_4R_4$)$_n$—$R_5$;
$R_3$ is independently selected from H, $C_{1-4}$alkyl substituted with 0-4 $R_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, (—CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$-$C_{3-6}$ carbocyclyl substituted with 0-3 $R_e$, and —(CH$_2$)$_r$-heterocyclyl substituted with 0-3 $R_e$;
$R_4$ is independently selected from H and $C_{1-4}$alkyl substituted with 0-4 $R_e$;
$R_5$ is independently selected from $C_{3-6}$ cycloalkyl, heterocyclyl, aryl and heteroaryl, each substituted with 1-5 $R_6$;
alternatively, when L is —$NR_4$—, —C(O)$NR_4$—, $R_4$ and $R_5$ together with the nitrogen atom to which they are both attached form a heterocyclic ring substituted with 1-5 $R_6$;
$R_6$ is independently selected from H, =O, F, Cl, Br, $C_{1-4}$alkyl, $C_{2-4}$alkenyl, $C_{2-4}$alkynyl, nitro, —(CR$_d$R$_d$)$_r$S(O)$_p$R$_c$, —(CR$_d$R$_d$)$_r$S(O)$_p$NR$_a$R$_a$, —(CR$_d$R$_d$)$_r$NR$_a$S(O)$_p$R$_c$, —(CR$_d$R$_d$)$_r$OR$_b$, —(CR$_d$R$_d$)$_r$CN, —(CR$_d$R$_d$)$_r$NR$_a$R$_a$, —(CR$_d$R$_d$)$_r$NR$_a$C(=O)R$_b$, —(CR$_d$R$_d$)$_r$NR$_a$C(=O)NR$_a$R$_a$, —(CR$_d$R$_d$)$_r$NR$_a$C(=O)OR$_b$, —(CR$_d$R$_d$)$_r$C(=O)OR$_b$, —(CR$_d$R$_d$)$_r$C(=O)NR$_a$R$_a$, —(CR$_d$R$_d$)$_r$C(=O)R$_b$, —(CR$_d$R$_d$)$_r$OC(=O)R$_b$, —(CR$_d$R$_d$)$_r$OC(=O)NR$_a$R$_a$, —(CR$_d$R$_d$)$_r$-cycloalkyl, —(CR$_d$R$_d$)$_r$-heterocyclyl, —(CR$_d$R$_d$)$_r$-aryl, and —(CR$_d$R$_d$)$_r$-heteroaryl, wherein said alkyl, cycloalkyl, heterocyclyl, aryl, or heteroaryl is substituted with 0-4 $R_e$;
$R_7$ is independently selected from H, F, Cl, Br, CN, $C_{1-4}$ alkyl substituted with 0-3 $R_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—$C_{3-6}$ carbocyclyl substituted with 0-3 $R_e$, and —(CH$_2$)$_r$-heterocyclyl substituted with 0-3 $R_e$;
$R_8$ is independently selected from H, F, Cl, Br, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—$C_{3-6}$ carbocyclyl substituted with 0-3 $R_e$, and —(CH$_2$)$_r$-heterocyclyl substituted with 0-3 $R_e$;
$R_9$ is independently selected from H and $C_{1-4}$alkyl substituted with 0-4 $R_e$;
$R_a$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;
$R_b$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;
$R_c$ is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $C_{3-6}$ carbocyclyl, and heterocyclyl;
$R_d$ is independently selected from H and $C_{1-4}$alkyl substituted with 0-5 $R_e$;
$R_e$ is independently selected from $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$—$C_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$ and —(CH$_2$)$_r$NR$_f$R$_f$;

R$_f$ is independently selected from H, F, Cl, Br, CN, OH, C$_{1-5}$alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

n, at each occurrence, is independently selected from 0, 1, 2, and 3;

p, at each occurrence, is independently selected from 0, 1, and 2; and r is independently selected from 0, 1, 2, 3, and 4.

In another aspect, the present invention provides compounds of Formula (II):

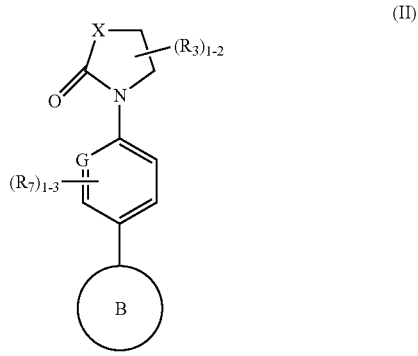

(II)

or stereoisomers, enantiomers, diastereoisomers, tautomers, pharmaceutically acceptable salts, solvates, or prodrugs thereof, wherein Ring B is selected from

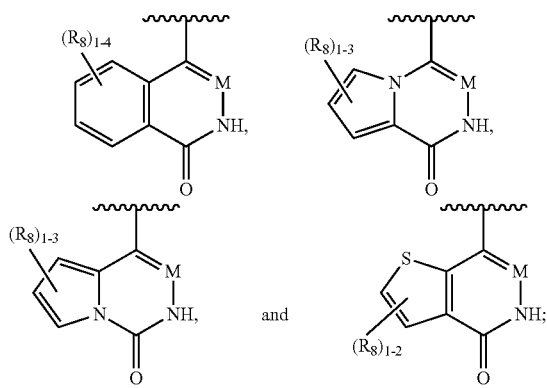

G is selected from N and CR$_7$;
M is independently selected from N and CR$_9$;
X is independently selected from CR$_1$, NR$_2$, and O;
L is absent or independently selected from —NR$_4$—, —C(O)NR$_4$(CR$_4$R$_4$)$_n$—, and —O—;
R$_1$ is L-R$_5$;
R$_2$ is —(CR$_4$R$_4$)$_n$—R$_5$;
R$_3$ is independently selected from H, C$_{1-4}$alkyl substituted with 0-4 R$_e$, (CH$_2$)$_r$—C$_{3-6}$ carbocyclyl substituted with 0-3 R$_e$, and —(CH$_2$)$_r$-heterocyclyl substituted with 0-3 R$_e$;
R$_4$ is independently selected from H and C$_{1-4}$alkyl substituted with 0-4 R$_e$;

R$_5$ is independently selected from C$_{3-6}$ cycloalkyl, heterocyclyl, aryl and heteroaryl, each substituted with 1-5 R$_6$;

alternatively, when L is —NR$_4$—, —C(O)NR$_4$—, R$_4$ and R$_5$ together with the nitrogen atom to which they are both attached form a heterocyclic ring substituted with 1-5 R$_6$;

R$_6$ is independently selected from H, =O, F, Cl, Br, C$_{1-4}$alkyl, C$_{2-4}$ alkenyl, C$_{2-4}$ alkynyl, nitro, —(CR$_d$R$_d$)$_r$S(O)$_p$R$_c$, —(CR$_d$R$_d$)$_r$S(O)$_p$NR$_a$R$_a$, —(CR$_d$R$_d$)$_r$NR$_a$S(O)$_p$R$_c$, —(CR$_d$R$_d$)$_r$OR$_b$, —(CR$_d$R$_d$)$_r$CN, —(CR$_d$R$_d$)$_r$NR$_a$R$_a$, —(CR$_d$R$_d$)$_r$NR$_a$C(=O)R$_b$, —(CR$_d$R$_d$)$_r$NR$_a$C(=O)NR$_a$R$_a$, —(CR$_d$R$_d$)$_r$NR$_a$C(=O)OR$_b$, —(CR$_d$R$_d$)$_r$C(=O)OR$_b$, —(CR$_d$R$_d$)$_r$C(=O)NR$_a$R$_a$, —(CR$_d$R$_d$)$_r$C(=O)R$_b$, —(CR$_d$R$_d$)$_r$OC(=O)R$_b$, —(CR$_d$R$_d$)$_r$OC(=O)NR$_a$R$_a$, —(CR$_d$R$_d$)$_r$-cycloalkyl, —(CR$_d$R$_d$)$_r$-heterocyclyl, —(CR$_d$R$_d$)$_r$-aryl, and —(CR$_d$R$_d$)$_r$-heteroaryl, wherein said alkyl, cycloalkyl, heterocyclyl, aryl, or heteroaryl is substituted with 0-4 R$_e$;

R$_7$ is independently selected from H, F, Cl, Br, CN, C$_{1-4}$ alkyl substituted with 0-3 R$_e$, —(CH$_2$)$_r$OR$_b$;

R$_8$ is independently selected from H, F, Cl, Br, and —(CH$_2$)$_r$OR$_b$;

R$_9$ is independently selected from H and C$_{1-4}$alkyl substituted with 0-4 R$_e$;

R$_a$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$ is independently selected from C$_{1-6}$ alkyl substituted with 0-5 R$_e$, C$_{2-6}$ alkenyl substituted with 0-5 R$_e$, C$_{2-6}$ alkynyl substituted with 0-5 R$_e$, C$_{3-6}$ carbocyclyl, and heterocyclyl;

R$_d$, at each occurrence, is independently selected from H and C$_{1-4}$alkyl substituted with 0-5 R$_e$;

R$_e$ is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$ and —(CH$_2$)$_r$NR$_f$R$_f$;

R$_f$ is independently selected from H, F, Cl, Br, CN, OH, C$_{1-5}$alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

n, at each occurrence, is independently selected from 0, 1, and 2;

p, at each occurrence, is independently selected from 0, 1, and 2; and r is independently selected from 0, 1, 2, 3, and 4.

In another aspect, the present invention provides compounds of Formula (III):

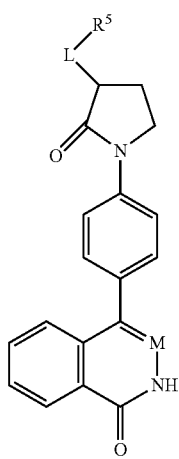

(III)

or stereoisomers, tautomers, pharmaceutically acceptable salts, solvates, or prodrugs thereof, wherein L is absent or independently from —$NR_4$—, —C(O)$NR_4$($CR_4R_4$)$_n$—, and —O—;

M is independently selected from N and CH;

$R_4$ is independently selected from H and $C_{1-4}$alkyl substituted with 0-4 $R_e$;

$R_5$ is independently selected from $C_{3-6}$ cycloalkyl, heterocyclyl, aryl and heteroaryl, each substituted with 1-5 $R_6$; alternatively, when L is —$NR_4$—, —C(O)$NR_4$—, $R_4$ and $R_5$ together with the nitrogen atom to which they are both attached form a heterocyclic ring substituted with 1-5 $R_6$;

$R_6$ is independently selected from H, =O, F, Cl, Br, $C_{1-4}$alkyl, $C_{2-4}$ alkenyl, $C_{2-4}$ alkynyl, nitro, —($CR_dR_d$)$_r$S(O)$_p$$R_c$, —($CR_dR_d$)$_r$S(O)$_p$$NR_aR_a$, —($CR_dR_d$)$_r$$NR_a$S(O)$_p$$R_c$, —($CR_dR_d$)$_r$$OR_b$, —($CR_dR_d$)$_r$CN, —($CR_dR_d$)$_r$$NR_a$$R_a$, —($CR_dR_d$)$_r$$NR_a$C(=O)$R_b$, —($CR_dR_d$)$_r$$NR_a$C(=O)$NR_aR_a$, —($CR_dR_d$)$_r$$NR_a$C(=O)$OR_b$, —($CR_dR_d$)$_r$C(=O)$OR_b$, —($CR_dR_d$)$_r$C(=O)$NR_aR_a$, —($CR_dR_d$)$_r$C(=O)$R_b$, —($CR_dR_d$)$_r$OC(=O)$R_b$, —($CR_dR_d$)$_r$OC(=O)$NR_aR_a$, —($CR_dR_d$)$_r$-cycloalkyl, —($CR_dR_d$)$_r$-heterocyclyl, —($CR_dR_d$)$_r$-aryl, and —($CR_dR_d$)$_r$-heteroaryl, wherein said alkyl, cycloalkyl, heterocyclyl, aryl, or heteroaryl is substituted with 0-4 $R_e$;

$R_a$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —($CH_2$)$_r$—$C_{3-10}$carbocyclyl substituted with 0-5 $R_e$, and —($CH_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —($CH_2$)$_r$—$C_{3-10}$carbocyclyl substituted with 0-5 $R_e$, and —($CH_2$)$_r$-heterocyclyl substituted with 0-5 $R_e$;

$R_c$ is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$ is independently selected from $C_{1-6}$ alkyl substituted with 0-5 $R_f$, $C_{2-6}$ alkenyl, $C_{2-6}$ alkynyl, —($CH_2$)$_r$—$C_{3-6}$ cycloalkyl, —($CH_2$)$_r$—$C_{4-6}$ heterocyclyl, —($CH_2$)$_r$-aryl, —($CH_2$)$_r$-heteroaryl, F, Cl, Br, CN, $NO_2$, =O, $CO_2$H, —($CH_2$)$_r$$OR_f$, S(O)$_p$$R_f$, C(=O)$NR_fR_f$, $NR_f$C(=O)$R_d$, S(O)$_p$$NR_fR_f$, $NR_f$S(O)$_p$$R_d$, $NR_f$C(=O)$OR_d$, OC(=O)$NR_fR_f$ and —($CH_2$)$_r$$NR_fR_f$;

$R_f$ is independently selected from H, F, Cl, Br, CN, OH, $C_{1-5}$alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from 0, 1, and 2; and r is independently selected from 0, 1, 2, 3, and 4.

In another aspect, the present invention provides compounds of Formula (III) or stereoisomers, enantiomers, diastereoisomers, tautomers, pharmaceutically acceptable salts, solvates, or prodrugs thereof, wherein L is independently selected from —$NR_4$—, —C(O)$NR_4$($CH_2$)$_{0-1}$—, and —O—;

$R_4$ is independently selected from H and $C_{1-4}$alkyl substituted with 0-4 $R_e$;

$R_5$ is independently selected from

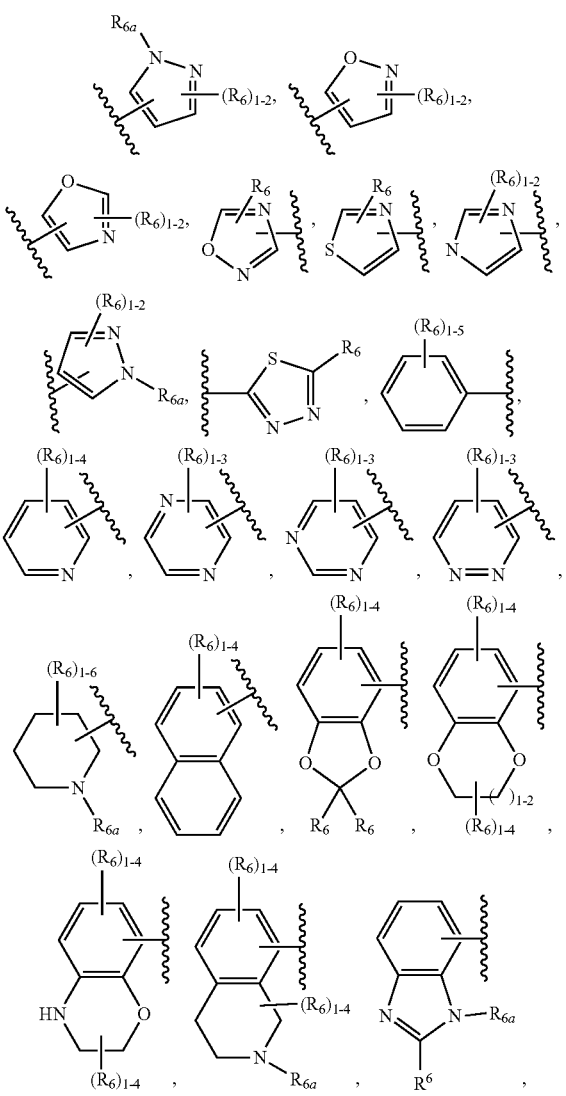

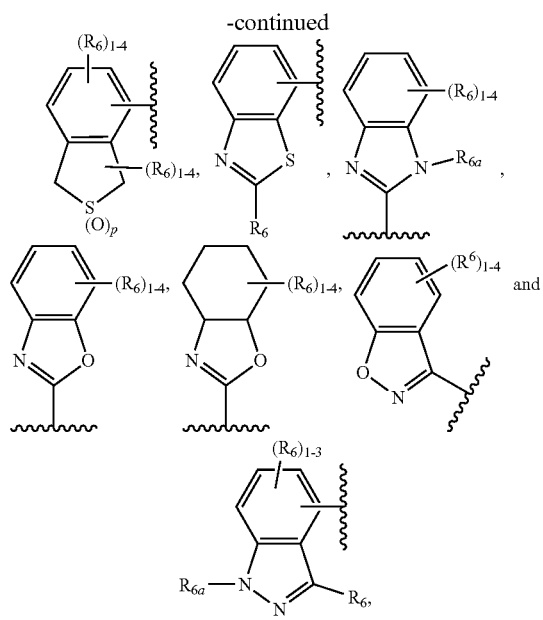

$R_6$ is independently selected from H, =O, F, Cl, Br, $C_{1-4}$alkyl, $C_{2-4}$ alkenyl, $C_{2-4}$ alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$NR$_a$C(=O)OR$_b$, —(CHR$_d$)$_r$C(=O)OR$_b$, —(CHR$_d$)$_r$C(=O)NR$_a$R$_a$, —(CHR$_d$)$_r$OC(=O)NR$_a$R$_a$, —(CHR$_d$)$_r$C(=O)R$_b$, —(CHR$_d$)$_r$ OC(=O)R$_b$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

$R_{6a}$ is independently selected from H, $C_{1-4}$ alkyl, —S(O)$_p$R$_c$, —S(O)$_p$NR$_a$R$_a$, —C(=O)OR$_b$, —(CH$_2$)$_r$C(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

$R_a$, at each occurrence, is independently selected from H, $C_{1-6}$ alkyl substituted with 0-5 R$_e$, $C_{2-6}$ alkenyl substituted with 0-5 R$_e$, $C_{2-6}$ alkynyl substituted with 0-5 R$_e$, —(CH$_2$)$_r$—$C_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

$R_b$, at each occurrence, is independently selected from H, $C_{1-6}$ alkyl substituted with 0-5 R$_e$, $C_{2-6}$ alkenyl substituted with 0-5 R$_e$, $C_{2-6}$ alkynyl substituted with 0-5 R$_e$, —(CH$_2$)$_r$—$C_{3-10}$carbocyclyl substituted with 0-5 R$_e$, and —(CH$_2$)$_r$-heterocyclyl substituted with 0-5 R$_e$;

$R_c$, at each occurrence, is independently selected from $C_{1-6}$ alkyl substituted with 0-5 R$_e$, $C_{2-6}$ alkenyl substituted with 0-5 R$_e$, $C_{2-6}$ alkynyl substituted with 0-5 R$_e$, $C_{3-6}$ carbocyclyl, and heterocyclyl;

$R_d$, at each occurrence, is independently selected from H and $C_{1-4}$alkyl substituted with 0-5 R$_e$;

$R_e$, at each occurrence, is independently selected from $C_{1-6}$ alkyl substituted with 0-5 R$_f$, $C_{2-6}$ alkenyl, $C_{2-6}$ alkynyl, —(CH$_2$)$_r$—$C_{3-6}$ cycloalkyl, —(CH$_2$)$_r$—$C_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from H, F, Cl, Br, CN, OH, $C_{1-5}$ alkyl, $C_{3-6}$ cycloalkyl, and phenyl;

or R$_f$ and R$_f$ together with the nitrogen atom to which they are both attached form a heterocyclic ring optionally substituted with $C_{1-4}$ alkyl;

p, at each occurrence, is independently selected from zero, 1, and 2; and r, at each occurrence, is independently selected from zero, 1, 2, 3, and 4; and other variables are as defined in Formula (III) above.

In another aspect, the present invention provides compounds of Formula (III) or stereoisomers, enantiomers, diastereoisomers, tautomers, pharmaceutically acceptable salts, solvates, or prodrugs thereof, wherein L is independently selected from —NR$_4$— and —C(O)NR$_4$—;

R$_4$ and R$_5$ are taken together with the nitrogen atom to which they are attached to form a heterocycle selected from

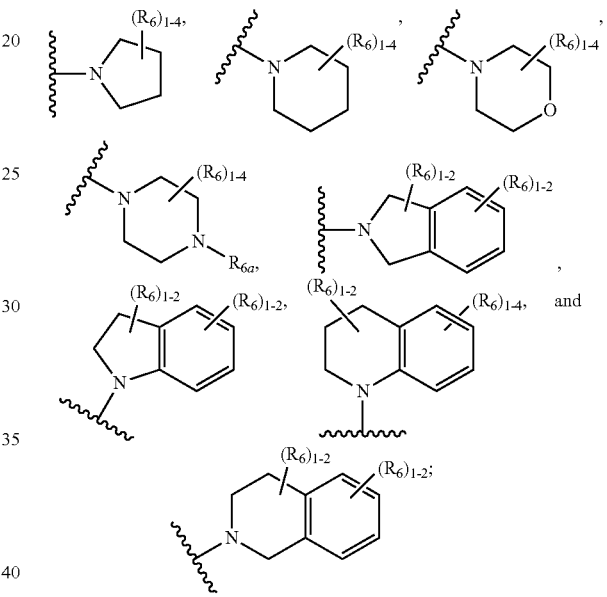

$R_6$ is independently selected from H, =O, F, Cl, Br, $C_{1-4}$alkyl, $C_{2-4}$ alkenyl, $C_{2-4}$ alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$NR$_a$C(=O)OR$_b$, —(CHR$_d$)$_r$C(=O)OR$_b$, —(CHR$_d$)$_r$C(=O)NR$_a$R$_a$, —(CHR$_d$)$_r$OC(=O)NR$_a$R$_a$, —(CHR$_d$)$_r$C(=O)R$_b$, —(CHR$_d$)$_r$ OC(=O)R$_b$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

$R_{6a}$ is independently selected from H, $C_{1-4}$ alkyl, —S(O)$_p$R$_c$, —S(O)$_p$NR$_a$R$_a$, —C(=O)OR$_b$, —(CH$_2$)$_r$C(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

$R_a$, at each occurrence, is independently selected from H, $C_{1-6}$ alkyl substituted with 0-5 R$_e$, $C_{2-6}$ alkenyl substituted with 0-5 R$_e$, $C_{2-6}$ alkynyl substituted with 0-5 R$_e$, —(CH$_2$)$_r$—$C_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$ alkyl;

p, at each occurrence, is independently selected from zero, 1, and 2; and r, at each occurrence, is independently selected from zero, 1, 2, 3, and 4; and other variables are as defined in Formula (III) above.

In another aspect, the present invention provides compounds of Formula (III) or stereoisomers, enantiomers, diastereoisomers, tautomers, pharmaceutically acceptable salts, solvates, or prodrugs thereof, wherein L is —O—;

$R_5$ is independently selected from

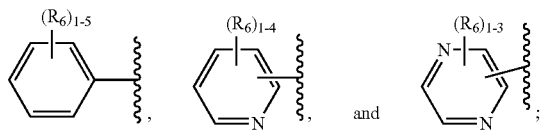

$R_6$ is independently selected from H, =O, F, Cl, Br, $C_{1-4}$alkyl, $C_{2-4}$ alkenyl, $C_{2-4}$ alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rNR_aC(=O)OR_b$, —$(CHR_d)_rC(=O)OR_b$, —$(CHR_d)_rC(=O)NR_aR_a$, —$(CHR_d)_rOC(=O)NR_aR_a$, —$(CHR_d)_rC(=O)R_b$, —$(CHR_d)_r$ $OC(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$; $R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$ alkyl;

p, at each occurrence, is independently selected from zero, 1, and 2; and r, at each occurrence, is independently selected from zero, 1, 2, 3, and 4; and other variables are as defined in Formula (III) above.

In another aspect, the present invention provides compounds of Formula (IV):

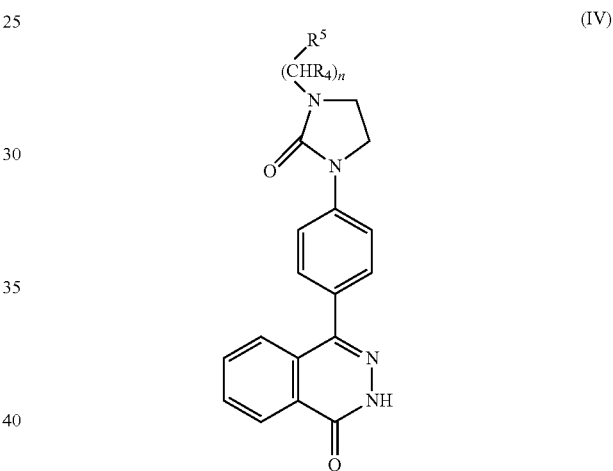

or stereoisomers, tautomers, pharmaceutically acceptable salts, solvates, or prodrugs thereof, wherein $R_4$ is independently selected from H and $C_{1-4}$alkyl substituted with 0-4 $R_e$;

$R_5$ is independently selected from $C_{3-6}$ cycloalkyl, heterocyclyl, aryl and heteroaryl, each substituted with 1-5 $R_6$;

$R_6$ is independently selected from H, =O, F, Cl, Br, $C_{1-4}$alkyl, $C_{2-4}$ alkenyl, $C_{2-4}$ alkynyl, nitro, —$(CR_dR_d)_rS(O)_pR_e$, —$(CR_dR_d)_rS(O)_pNR_aR_a$, —$(CR_dR_d)_rNR_aS(O)_pR_c$, —$(CR_dR_d)_rOR_b$, —$(CR_dR_d)_rCN$, —$(CR_dR_d)_rNR_aR_a$, —$(CR_dR_d)_rNR_aC(=O)R_b$, —$(CR_dR_d)_rNR_aC(=O)NR_aR_a$, —$(CR_dR_d)_rNR_aC(=O)OR_b$, —$(CR_dR_d)_rC(=O)OR_b$, —$(CR_dR_d)_rC(=O)NR_aR_a$, —$(CR_dR_d)_rC(=O)R_b$, —$(CR_dR_d)_rOC(=O)R_b$, —$(CR_dR_d)_rOC(=O)NR_aR_a$, —$(CR_dR_d)_r$-cycloalkyl, —$(CR_dR_d)_r$-heterocyclyl, —$(CR_dR_d)_r$-aryl, and —$(CR_dR_d)_r$-heteroaryl, wherein said alkyl, cycloalkyl, heterocyclyl, aryl, or heteroaryl is substituted with 0-4 $R_e$;

$R_a$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_c$ is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $C_{3-6}$ carbocyclyl, and heterocyclyl;

$R_e$ is independently selected from $C_{1-6}$ alkyl substituted with 0-5 $R_f$, $C_{2-6}$ alkenyl, $C_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O) NR$_f$R$_f$ and —(CH$_2$)$_r$NR$_f$R$_f$;

$R_f$ is independently selected from H, F, Cl, Br, CN, OH, $C_{1-5}$alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

n, at each occurrence, is independently selected from 0 and 1;

p, at each occurrence, is independently selected from 0, 1, and 2; and r is independently selected from 0, 1, 2, 3, and 4.

In another aspect, the present invention provides compounds of Formula (V):

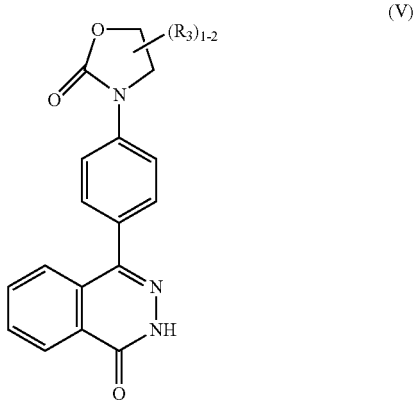

(V)

or stereoisomers, tautomers, pharmaceutically acceptable salts, solvates, or prodrugs thereof, wherein $R_3$ is independently selected from H, $C_{1-4}$alkyl substituted with 0-4 $R_e$, —(CH$_2$)$_r$OR$_b$, (CH$_2$)$_r$S(O)$_p$R$_c$, —(CH$_2$)$_r$C (=O)R$_b$, —(CH$_2$)$_r$NR$_a$R$_a$, —(CH$_2$)$_r$CN, —(CH$_2$)$_r$C (=O)NR$_a$R$_a$, —(CH$_2$)$_r$NR$_a$C(=O)R$_b$, —(CH$_2$)$_r$NR$_a$C (=O)NR$_a$R$_a$, —(CH$_2$)$_r$NR$_a$C(=O)OR$_b$, —(CH$_2$)$_r$OC (=O)NR$_a$R$_a$, —(CH$_2$)$_r$C(=O)OR$_b$, —(CH$_2$)$_r$S(O)$_p$ NR$_a$R$_a$, —(CH$_2$)$_r$NR$_a$S(O)$_p$NR$_a$R$_a$, —(CH$_2$)$_r$NR$_a$S(O)$_p$ R$_c$, (CH$_2$)$_r$—C$_{3-6}$ carbocyclyl substituted with 0-3 $R_e$, and —(CH$_2$)$_r$-heterocyclyl substituted with 0-3 $R_e$;

$R_a$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_c$ is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $C_{3-6}$ carbocyclyl, and heterocyclyl;

$R_e$ is independently selected from $C_{1-6}$ alkyl substituted with 0-5 $R_f$, $C_{2-6}$ alkenyl, $C_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O) NR$_f$R$_f$ and —(CH$_2$)$_r$NR$_f$R$_f$;

$R_f$ is independently selected from H, F, Cl, Br, CN, OH, $C_{1-5}$alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from 0, 1, and 2; and r is independently selected from 0, 1, 2, 3, and 4.

In another aspect, the present invention provides compounds of Formula (VI):

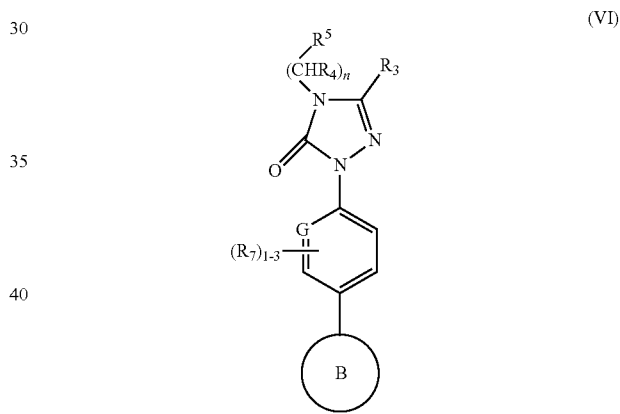

(VI)

or stereoisomers, tautomers, pharmaceutically acceptable salts, solvates, or prodrugs thereof, wherein Ring B is selected from

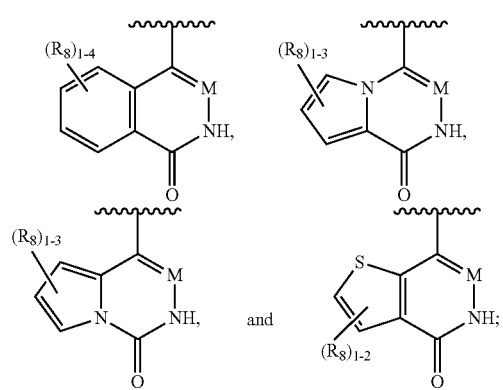

G is selected from N and CR$_7$;

M is independently selected from N and CR$_9$;

R$_3$ is independently selected from H, C$_{1-4}$alkyl substituted with 0-4 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_4$ is independently selected from H and C$_{1-4}$alkyl substituted with 0-4 R$_e$;

R$_5$ is independently selected from C$_{3-6}$ cycloalkyl, heterocyclyl, aryl and heteroaryl, each substituted with 1-5 R$_6$;

R$_6$ is independently selected from H, =O, F, Cl, Br, C$_{1-4}$alkyl, C$_{2-4}$ alkenyl, C$_{2-4}$ alkynyl, nitro, —(CR$_d$R$_d$)$_r$S(O)$_p$R$_e$, —(CR$_d$R$_d$)$_r$S(O)$_p$NR$_a$R$_a$, —(CR$_d$R$_d$)$_r$NR$_a$S(O)$_p$R$_c$, —(CR$_d$R$_d$)$_r$OR$_b$, —(CR$_d$R$_d$)$_r$CN, —(CR$_d$R$_d$)$_r$NR$_a$R$_a$, —(CR$_d$R$_d$)$_r$NR$_a$C(=O)R$_b$, —(CR$_d$R$_d$)$_r$NR$_a$C(=O)NR$_a$R$_a$, —(CR$_d$R$_d$)$_r$NR$_a$C(=O)OR$_b$, —(CR$_d$R$_d$)$_r$C(=O)OR$_b$, —(CR$_d$R$_d$)$_r$C(=O)NR$_a$R$_a$, —(CR$_d$R$_d$)$_r$C(=O)R$_b$, —(CR$_d$R$_d$)$_r$OC(=O)R$_b$, —(CR$_d$R$_d$)$_r$OC(=O)NR$_a$R$_a$, —(CR$_d$R$_d$)$_r$-cycloalkyl, —(CR$_d$R$_d$)$_r$-heterocyclyl, —(CR$_d$R$_d$)$_r$-aryl, and —(CR$_d$R$_d$)$_r$-heteroaryl, wherein said alkyl, cycloalkyl, heterocyclyl, aryl, or heteroaryl is substituted with 0-4 R$_e$;

R$_7$ is independently selected from H, F, Cl, Br, CN, C$_{1-4}$ alkyl substituted with 0-3 R$_e$, —(CH$_2$)$_r$OR$_b$;

R$_8$ is independently selected from H, F, Cl, Br, and —(CH$_2$)$_r$OR$_b$;

R$_9$ is independently selected from H and C$_{1-4}$ alkyl substituted with 0-4 R$_e$;

R$_a$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$ is independently selected from C$_{1-6}$ alkyl substituted with 0-5 R$_e$, C$_{2-6}$ alkenyl substituted with 0-5 R$_e$, C$_{2-6}$ alkynyl substituted with 0-5 R$_e$, C$_{3-6}$ carbocyclyl, and heterocyclyl;

R$_e$ is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$ and —(CH$_2$)$_r$NR$_f$R$_f$;

R$_f$ is independently selected from H, F, Cl, Br, CN, OH, C$_{1-5}$alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

n, at each occurrence, is independently selected from 0 and 1;

p, at each occurrence, is independently selected from 0, 1, and 2; and r is independently selected from 0, 1, 2, 3, and 4.

In another aspect, the present invention provides compounds of Formula (VII):

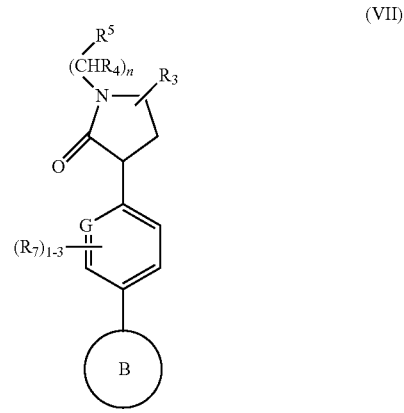

(VII)

or stereoisomers, enantiomers, diastereoisomers, tautomers, pharmaceutically acceptable salts, solvates, or prodrugs thereof, wherein Ring B is selected from

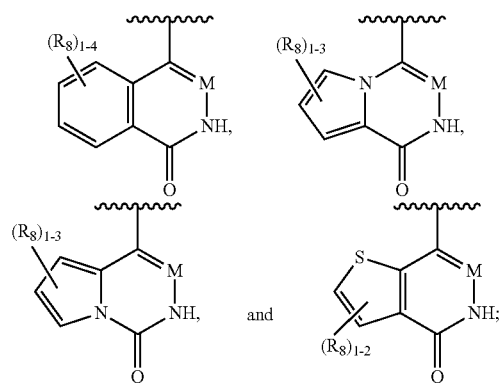

G is selected from N and CR$_7$;

M is independently selected from N and CR$_9$;

R$_3$ is independently selected from H, C$_{1-4}$alkyl substituted with 0-4 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_4$ is independently selected from H and C$_{1-4}$alkyl substituted with 0-4 R$_e$;

R$_5$ is independently selected from C$_{3-6}$ cycloalkyl, heterocyclyl, aryl and heteroaryl, each substituted with 1-5 R$_6$;

R$_6$ is independently selected from H, =O, F, Cl, Br, C$_{1-4}$alkyl, C$_{2-4}$ alkenyl, C$_{2-4}$ alkynyl, nitro, —(CR$_d$R$_d$)$_r$S(O)$_p$R$_e$, —(CR$_d$R$_d$)$_r$S(O)$_p$NR$_a$R$_a$, —(CR$_d$R$_d$)$_r$NR$_a$S(O)$_p$R$_c$, —(CR$_d$R$_d$)$_r$OR$_b$, —(CR$_d$R$_d$)$_r$CN, —(CR$_d$R$_d$)$_r$NR$_a$R$_a$, —(CR$_d$R$_d$)$_r$NR$_a$C(=O)R$_b$, —(CR$_d$R$_d$)$_r$NR$_a$C(=O)NR$_a$R$_a$, —(CR$_d$R$_d$)$_r$NR$_a$C(=O)OR$_b$, —(CR$_d$R$_d$)$_r$C(=O)OR$_b$, —(CR$_d$R$_d$)$_r$C(=O)NR$_a$R$_a$, —(CR$_d$R$_d$)$_r$C(=O)R$_b$, —(CR$_d$R$_d$)$_r$OC(=O)R$_b$, —(CR$_d$R$_d$)$_r$OC(=O)NR$_a$R$_a$, —(CR$_d$R$_d$)$_r$-cycloalkyl, —(CR$_d$R$_d$)$_r$-heterocyclyl, —(CR$_d$R$_d$)$_r$-aryl, and —(CR$_d$R$_d$)$_r$-heteroaryl, wherein said alkyl, cycloalkyl, heterocyclyl, aryl, or heteroaryl is substituted with 0-4 R$_e$;

R$_7$ is independently selected from H, F, Cl, Br, CN, C$_{1-4}$ alkyl substituted with 0-3 R$_e$, —(CH$_2$)$_r$OR$_b$;

R$_8$ is independently selected from H, F, Cl, Br, and —(CH$_2$)$_r$OR$_b$;

R$_9$ is independently selected from H and C$_{1-4}$alkyl substituted with 0-4 R$_e$;

R$_a$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$ is independently selected from C$_{1-6}$ alkyl substituted with 0-5 R$_e$, C$_{2-6}$ alkenyl substituted with 0-5 R$_e$, C$_{2-6}$ alkynyl substituted with 0-5 R$_e$, C$_{3-6}$ carbocyclyl, and heterocyclyl;

R$_e$ is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$ and —(CH$_2$)$_r$NR$_f$R$_f$;

R$_f$ is independently selected from H, F, Cl, Br, CN, OH, C$_{1-5}$alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

n, at each occurrence, is independently selected from 0 and 1;

p, at each occurrence, is independently selected from 0, 1, and 2; and r is independently selected from 0, 1, 2, 3, and 4.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments.

For example, in one non-limiting embodiment, ring A is

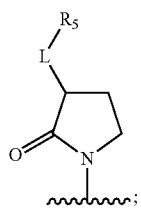

ring B is

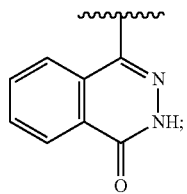 [SMILES: *c1n[nH]c(=O)c2ccccc12]

G is CH; L is —O—; R$_5$ is

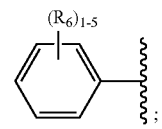

R$^6$ is independently selected from H, F, C$_1$, C$_{1-4}$ alkyl substituted with 0-3 R$^e$, and —OC$_{1-4}$ alkyl substituted with 0-3 R$^e$; and R$_e$ is independently selected from C$_{1-6}$ alkyl, F, Cl, Br, and CN.

In another non-limiting embodiment, ring A is

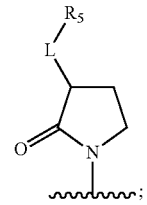

ring B is

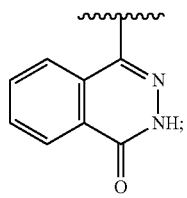 [SMILES: *c1n[nH]c(=O)c2ccccc12]

G is CH; L is —NH—; R$_5$ is independently selected from

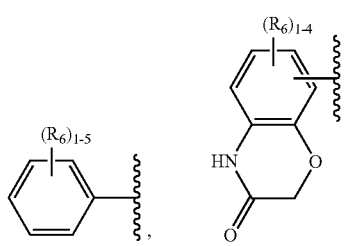

, and

-continued

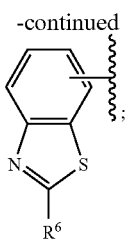

$R^6$ is independently selected from H, F, Cl, $C_{1-4}$ alkyl substituted with 0-3 $R^e$, and —$OC_{1-4}$ alkyl substituted with 0-3 $R^e$; and $R_e$ is independently selected from $C_{1-6}$ alkyl, F, Cl, Br, and CN.

In another non-limiting embodiment, ring A is

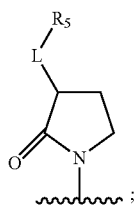

ring B is

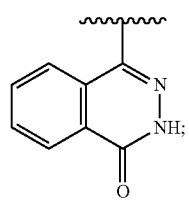 [SMILES: *c1n[nH]c(=O)c2ccccc12]

G is CH; L is —C(O)NR$_4$—; $R_4$ and $R_5$ are taken together with the nitrogen atom to which they are attached to form

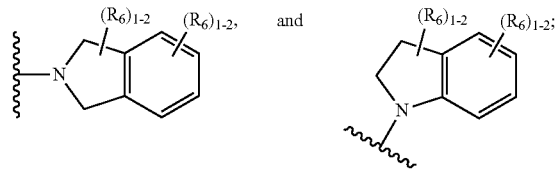

$R^6$ is independently selected from H, F, $C_1$, $C_{1-4}$ alkyl substituted with 0-3 $R^e$, and —$OC_{1-4}$ alkyl substituted with 0-3 $R^e$; and $R_e$ is independently selected from $C_{1-6}$ alkyl, F, Cl, Br, and CN.

In another aspect, the present invention provides a compound selected from any subset list of compounds exemplified in the present application.

In another embodiment, the compounds of the present invention have ROCK IC$_{50}$ values ≤10 µM.

In another embodiment, the compounds of the present invention have ROCK IC$_{50}$ values ≤1 µM.

In another embodiment, the compounds of the present invention have ROCK IC$_{50}$ values ≤0.5 µM.

In another embodiment, the compounds of the present invention have ROCK IC$_{50}$ values ≤0.1 µM.

In another embodiment, the compounds of the present invention have ROCK IC$_{50}$ values ≤0.05 µM.

In another embodiment, the compounds of the present invention have ROCK IC$_{50}$ values ≤0.01 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms.

Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and S(O)$_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard, H., Chapter 5, "Design and Application of Prodrugs", *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$ alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry, Academic Press*, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.
Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate $Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro (phenylmethylene)(triycyclohexyl-phosphine)ruthenium
HCl hydrochloric acid
HATU O-(7-azabenzotriazol-1-yl)-N,N,N',N'-tetramethyl-uronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS polystyrene
PyBOP benzotriazol-1-yl-oxytripyrrolidinophosphonium hexafluorophosphate
SEM-Cl 2-(trimethysilyl)ethoxymethyl chloride
2nd generation XPhos Chloro(2-dicyclohexylphosphino-2',4',6'-triisopropyl-1,1' precatalyst biphenyl)[2-(2'-amino-1,1'-biphenyl)]palladium(II), THF adduct
$SiO_2$ silica oxide
$SnCl_2$ tin(II) chloride
TBAI tetra-n-butylammonium iodide
TEA triethylamine
TFA trifluoroacetic acid
THF tetrahydrofuran
$TMSCHN_2$ trimethylsilyldiazomethane
T3P® propane phosphonic acid anhydride
TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 µL assay containing 20 mM HEPES, pH 7.5, 20 mM $MgCl_2$, 0.015% Brij-35, 4 mM DTT, 5 µM ATP and 1.5 µM peptide substrate (FITC-AHA-AKRRRLSSLRA-OH) (SEQ ID NO. 1). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LAB-CHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the $IC_{50}$; i.e., the concentration of compound required to inhibit 50% of kinase activity.

Representative Examples were tested in the ROCK2 assay described above and found having ROCK2 inhibitory activity. Their ROCK2 inhibitory activity ($IC_{50}$ values) of ≤2 µM (2000 nM) was observed and shown in Table A below. The ranges of the ROCK2 $IC_{50}$ values are as follows: ROCK2 $IC_{50}$: ++++ (<10 nM) +++ (10-100 nM) ++ (100-500 nM) + (500-2000 nM)

TABLE A

| Eample No. | ROCK2 $IC_{50}$ |
| --- | --- |
| 1 | ++ |
| 2 | ++++ |
| 3 | + |
| 4 | ++ |
| 5 | + |
| 6 | ++ |
| 7 | ++ |
| 8 | + |
| 9 | ++ |
| 10 | +++ |
| 11 | +++ |
| 12 | +++ |
| 13 | +++ |
| 14 | ++ |
| 15 | +++ |
| 18 | ++ |
| 17 | ++ |
| 16 | + |
| 19 | + |
| 20 | ++ |
| 21 | + |
| 22 | + |
| 23 | + |
| 24 | + |
| 25 | + |
| 26 | +++ |
| 27 | +++ |
| 28 | + |
| 29 | + |
| 30 | ++++ |
| 31 | +++ |
| 32 | +++ |
| 33 | +++ |
| 34 | +++ |
| 35 | +++ |
| 36 | +++ |
| 37 | +++ |
| 38 | +++ |
| 39 | +++ |
| 40 | +++ |
| 41 | ++ |
| 42 | +++ |
| 43 | +++ |
| 44 | + |
| 45 | + |
| 46 | ++ |
| 47 | + |
| 48 | +++ |
| 49 | +++ |
| 50 | +++ |
| 51 | +++ |
| 52 | ++++ |
| 53 | ++ |
| 54 | + |
| 55 | +++ |
| 56 | ++++ |
| 57 | +++ |
| 58 | ++++ |
| 59 | ++ |
| 60 | +++ |
| 61 | +++ |
| 62 | ++++ |
| 63 | ++ |
| 64 | +++ |
| 65 | ++ |
| 66 | ++++ |
| 67 | +++ |
| 68 | +++ |
| 69 | +++ |
| 70 | ++ |
| 71 | +++ |
| 72 | + |
| 73 | ++++ |
| 74 | +++ |
| 75 | + |
| 76 | +++ |
| 77 | +++ |
| 78 | +++ |
| 79 | ++++ |
| 80 | ++++ |
| 81 | +++ |
| 82 | ++++ |
| 83 | +++ |
| 84 | ++++ |
| 85 | ++++ |
| 86 | +++ |
| 87 | +++ |
| 88 | +++ |
| 89 | +++ |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example, as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples sections set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis,* 4th Edition, Wiley-Interscience (2006)).

Scheme 1.

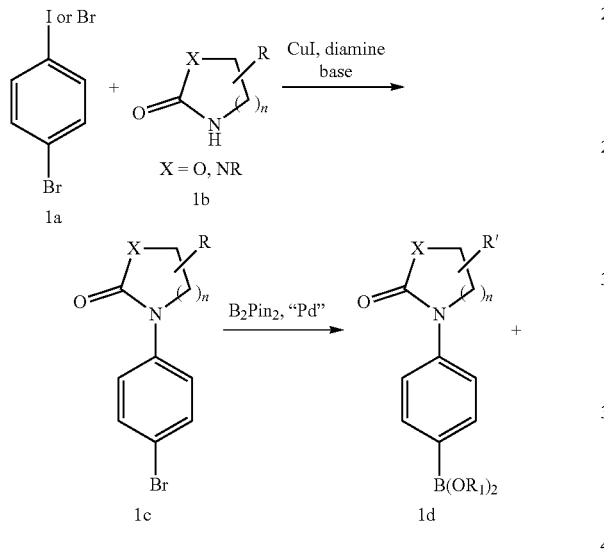

Scheme 2.

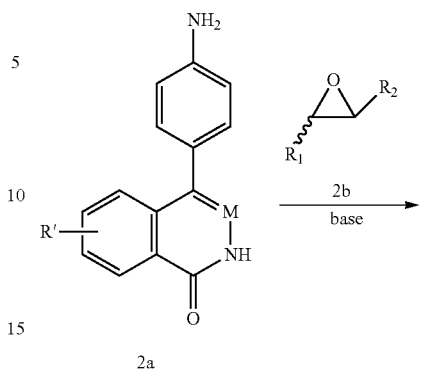

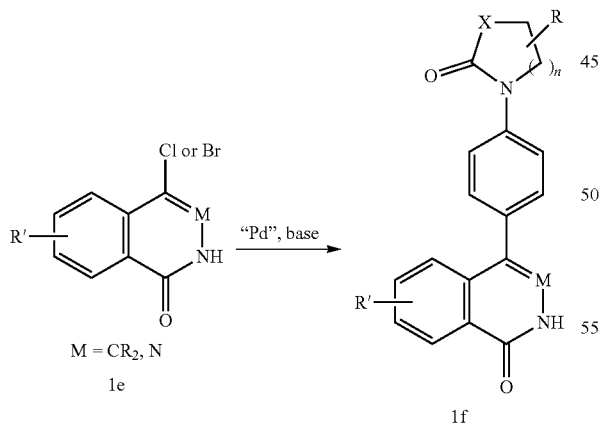

Scheme 1 shows the synthesis of generic compounds 1f. Ullmann-type coupling between aryl halide 1a and lactam, or urea, or cyclic carbamate 1b provides intermediate 1c. Intermediate 1c is converted to boronic acid, or boronate 1d, which undergoes Suzuki-Miyaura coupling with 1e in the presence of a base such as $K_3PO_4$ and a catalyst such as $Pd(PPh_3)_4$ to afford The oxazolidinone derivative 2d in Scheme 2 is formed via a cyclization reaction utilizing CDI from hydroxylamine intermediate 2c, which is obtained by reacting aniline derivative 2a with epoxide 2b under a basic reaction condition using a base such as TEA, $K_2CO_3$, or $Cs_2CO_3$.

Scheme 3.

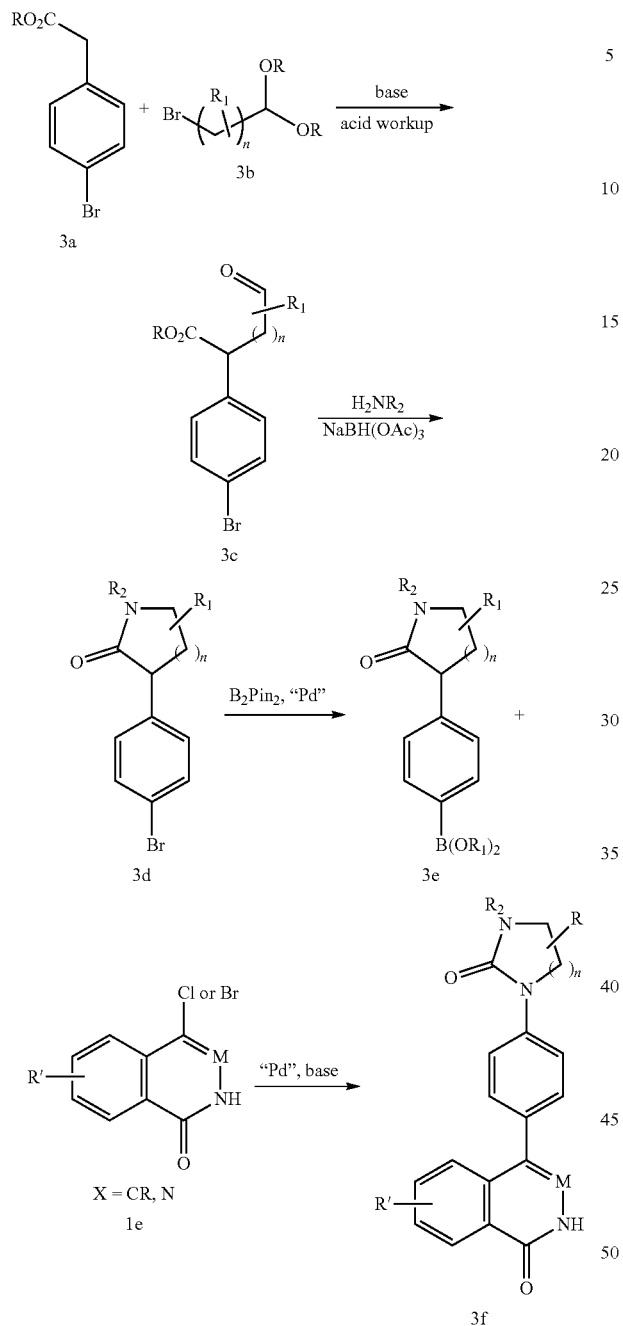

Scheme 4.

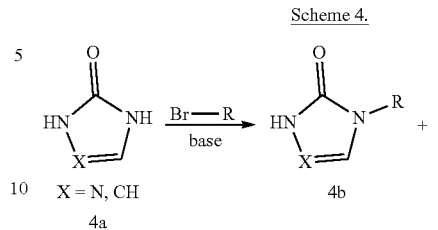

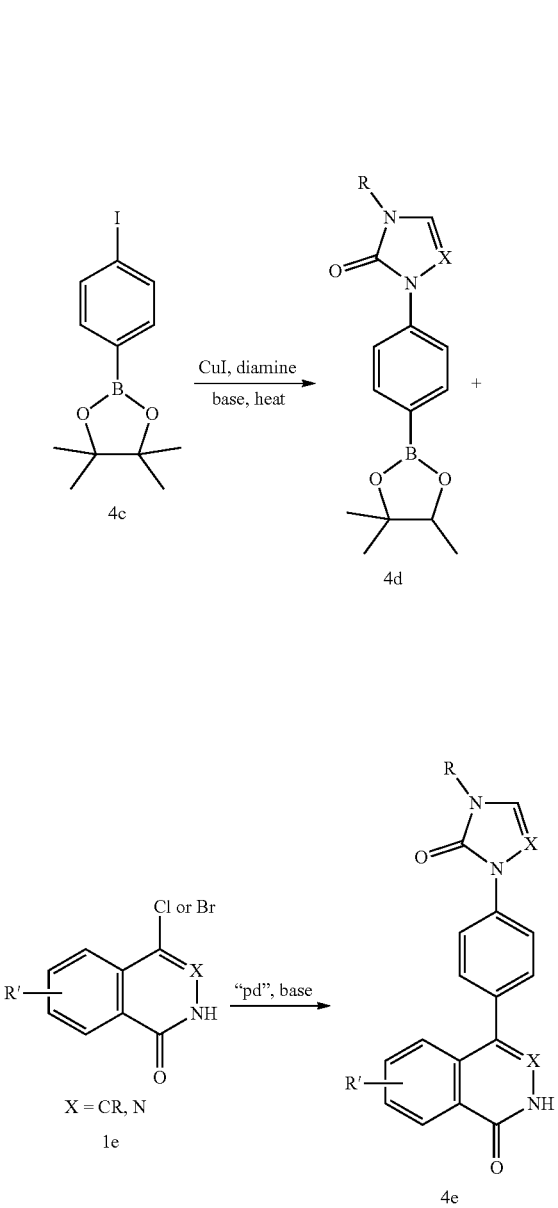

The synthesis of generic carbon-linked lactam target 3f was outlined in Scheme 3. Alkylation of 4-bromophenylacetate 3a with an appropriately functionalized alkylbromide 3b in the presence of a base, such as KHMDS, affords intermediate 3c after acidic workup. Intermediate 3c undergoes a reductive amination with a primary amine followed by in situ ring closing to afford lactam 3d. Intermediate 3d is converted to boronic acid, or boronate 3e, which reacts with 1e under Suzuki-Miyaura coupling condition in the presence of a base such as $K_3PO_4$ and a catalyst such as $Pd(PPh_3)_4$ to afford 3f Scheme 4 shows the synthesis of imidazolone or triazolone target 4e. Alkylation of 4a provides 4b. Ullmann-type reaction of 4b with aryl iodide 4c provides boronate 4d, which undergoes Suzuki-Miyaura coupling with 1e in the presence of a base such as $K_3PO_4$ and a catalyst such as $Pd(PPh_3)_4$ to afford target compound 4e.

Scheme 5.

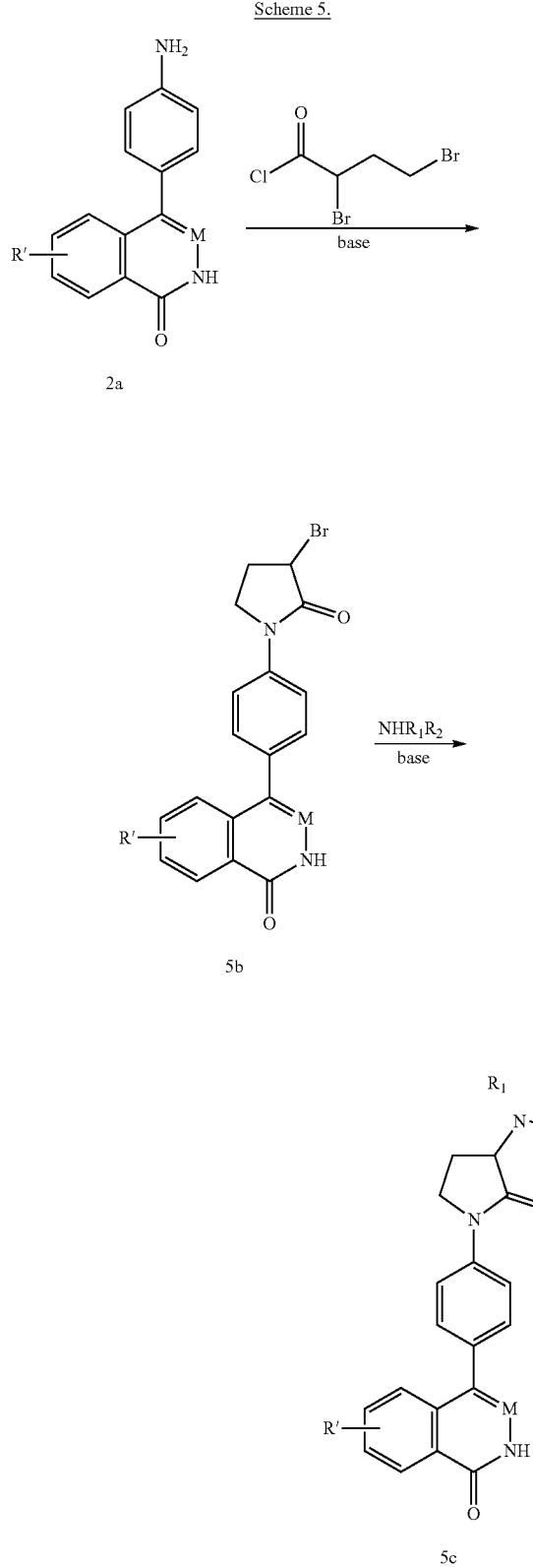

Scheme 6.

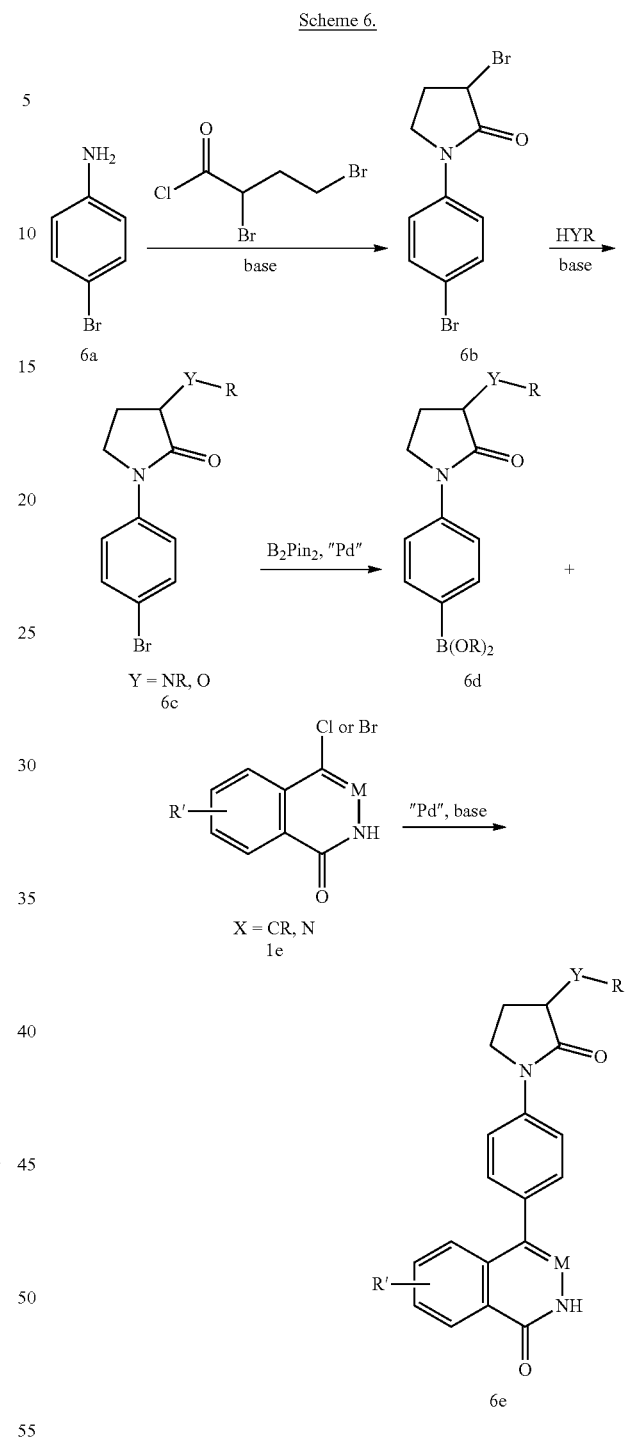

Scheme 5 shows the synthesis of lactam target 5c from 2a. Aniline 2a reacts with 2,4-dibromobutanoyl chloride at the presence of bases such as $K_3PO_4$, NaOH to provide bromolactam 5b. Intermediate 5b reacts with an amine to afford 5c.

Scheme 6 shows the synthesis of target 6e and an alternate synthesis of target 5c from aniline 6a. Under a basic condition, 6a reacts with 2,4-dibromobutanoyl chloride to provide dibromide 6b. Intermediate 6b reacts with an amine, or an alcohol, at the presence of a base such as $K_2CO_3$, to provide lactam derivative 6c. Aryl bromide 6c is converted to the aryl boronic acid or boronate ester 6d by coupling with bis(pinacolato)diboron in the presence of a base such a potassium acetate and a catalyst such as $PdCl_2(dppf)$. Suzuki-Miyaura coupling between 6d and aryl halide 1e in the presence of a base such as $K_3PO_4$ and a catalyst such as $Pd(PPh_3)_4$ affords target compound 6e.

Purification of intermediates and final products was carried out via either normal or reverse phase chromatography. Normal phase chromatography was carried out using pre-packed SiO$_2$ cartridges eluting with either gradients of hexanes and EtOAc or DCM and MeOH unless otherwise indicated. Reverse phase preparative HPLC was carried out using C18 columns eluting with gradients of Solvent A (90% H$_2$O, 10% MeOH, 0.1% TFA) and Solvent B (10% H$_2$O, 90% MeOH, 0.1% TFA, UV 220 nm) or with gradients of Solvent A (90% H$_2$O, 10% ACN, 0.1% TFA) and Solvent B (10% H$_2$O, 90% ACN, 0.1% TFA, UV 220 nm) or with gradients of Solvent A (98% H$_2$O, 2% ACN, 0.05% TFA) and Solvent B (98% ACN, 2% H$_2$O, 0.05% TFA, UV 220 nm) (or) Sunfire Prep C18 OBD 5u 30×100 mm, 25 min gradient from 0-100% B. A=H$_2$O/ACN/TFA 90:10:0.1. B=ACN/H$_2$O/TFA 90:10:0.1 (or) Waters XBridge C18, 19×200 mm, 5-μm particles; Guard Column: Waters XBridge C18, 19×10 mm, 5-μm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min.

Unless otherwise stated, analysis of final products was carried out by reverse phase analytical HPLC.

Method A:
Sunfire C18 column (3.5 μm C18, 3.0×150 mm). Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method B:
XBridge Phenyl column (3.5 μm C18, 3.0×150 mm). Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method C:
Waters BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes; Flow: 1.11 mL/min.

Method D:
Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.11 mL/min.

Intermediate 1:
4-(4-aminophenyl)phthalazin-1(2H)-one
Trifluoroacetic Acid Salt

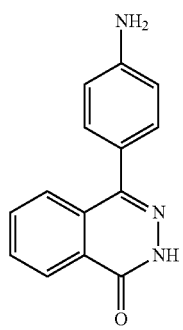 [SMILES: Nc1ccc(-c2n[nH]c(=O)c3ccccc23)cc1]

Intermediate 1A: ter t-butyl (4-(4-oxo-3,4-dihydrophthalazin-1-yl)phenyl)carbamate

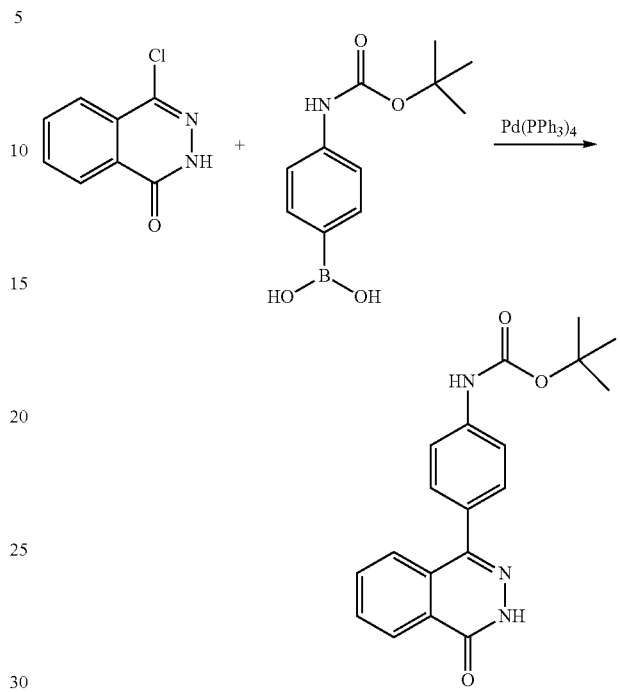

To 4-chlorophthalazin-1(2H)-one (118 mg, 0.653 mmol), (4-((tert-butoxycarbonyl)amino)phenyl)boronic acid (170 mg, 0.72 mmol) and K$_3$PO$_4$ (347 mg, 1.63 mmol), were added dioxane (9 mL) and water (1 mL). The mixture was degassed (evacuated and flushed with argon (5×)). Pd(PPh$_3$)$_4$ (37.8 mg, 0.033 mmol) was added, then the mixture was degassed (2×). The reaction vial was sealed and heated in a microwave reactor at 150° C. for 35 min. The reaction mixture was concentrated and purified via flash chromatography to afford 150 mg (68%) of Intermediate 1A. MS (ESI) m/z 338.1 (M+H)$^+$.

Intermediate 1B

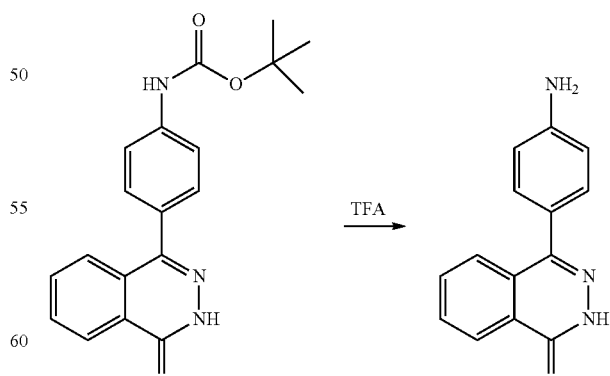

Intermediate 1A (150 mg, 0.45 mmol) was mixed with CH$_2$Cl$_2$ (3 mL), add TFA (2 mL), stirred at rt for 2 h. The mixture was concentrated and purified via flash chromatography, then preparative HPLC to afford 62 mg (59%) of Intermediate 3. MS (ESI) m/z 238.1 (M+H)+; 1H NMR (500 MHz, CD3OD) δ 8.44 (dt, J=4.7, 2.3 Hz, 1H), 7.97-7.87 (m, 2H), 7.81-7.75 (m, 1H), 7.71-7.61 (m, 2H), 7.41-7.30 (m, 2H)

Intermediate 2:
3-bromo-1-(4-bromophenyl)pyrrolidin-2-one

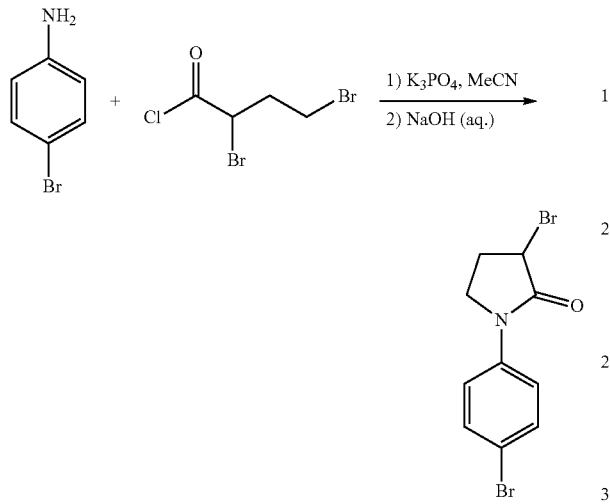

To a solution of 4-bromoaniline (4.85 g, 28.2 mmol) in acetonitrile (30 mL) were added K3PO4 (5.98 g, 28.2 mmol) and 2,4-dibromobutanoyl chloride (3.73 mL, 28.2 mmol) at 0° C. The reaction was stirred under N2 at rt for 1 h. To the reaction was then added 50% NaOH solution (7.44 mL, 141 mmol), and the reaction was stirred at rt for another 1 h. The solid was filtered off and washed with acetonitrile. The filtrate was dried over Na2SO4, filtered, and the solvent was removed. The crude product was purified by normal phase chromatography to provide Intermediate 2 (7.66 g, 85%) as a white solid. MS(ESI) m/z 317.9/319.9/321.9 (M+H)+; 1H NMR (400 MHz, CDCl3) δ 7.60-7.54 (m, 2H), 7.53-7.47 (m, 2H), 4.59 (dd, J=7.0, 2.9 Hz, 1H), 4.03 (ddd, J=9.8, 7.8, 6.6 Hz, 1H), 3.81 (ddd, J=10.0, 7.6, 2.6 Hz, 1H), 2.75 (dq, J=14.6, 7.5 Hz, 1H), 2.47 (ddt, J=14.4, 6.7, 2.9 Hz, 1H).

Intermediate 3: 4-(4-(3-bromo-2-oxopyrrolidin-1-yl)phenyl)phthalazin-1(2H)-one

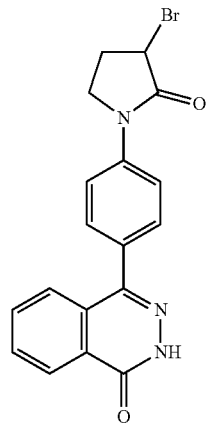

To a suspension of Intermediate 1 (300 mg, 1.26 mmol) in acetonitrile (10 mL) were added K3PO4 (268 mg, 1.26 mmol) and 2,4-dibromobutanoyl chloride (0.17 mL, 1.26 mmol) at 0° C. The reaction was stirred under N2 at rt for 1 h. Then to the reaction was added NaOH (50% aq. 0.33 mL, 6.32 mmol), and the reaction was stirred at rt for another 1 h. The solid was filtered off and washed with acetonitrile. The filtrate was dried over Na2SO4, filtered and the solvent was removed to afford Intermediate 3 as a solid. MS(ESI) m/z 384.0/386.0 (M+H)+.

Intermediate 4:
3-amino-1-(4-bromophenyl)pyrrolidin-2-one
Trifluoroacetic Acid Salt

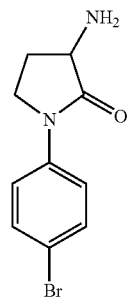

Intermediate 4A:
3-azido-1-(4-bromophenyl)pyrrolidin-2-one

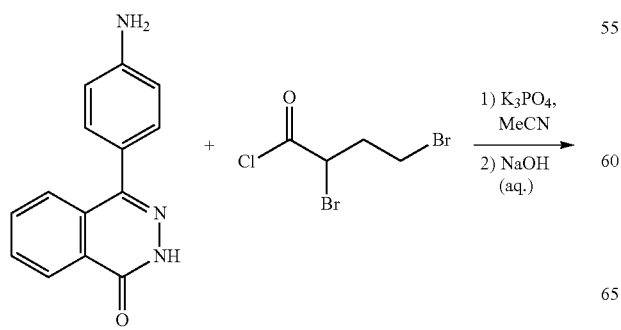

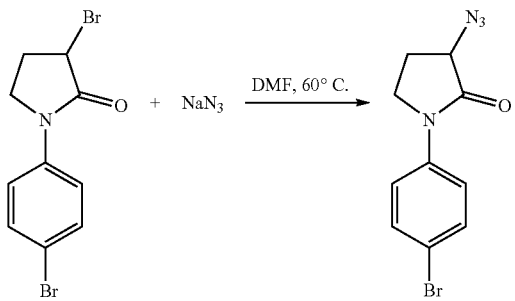 [SMILES: O=C1C(Br)CCN1c1ccc(Br)cc1 ; [N-]=[N+]=NC1CCN(c2ccc(Br)cc2)C1=O ; "NaN3"]

To a solution of Intermediate 2 (1.1 g, 3.45 mmol) in DMF (10 mL) was added NaN₃ (0.673 g, 10.4 mmol) at rt. The reaction was stirred under N₂ at 60° C. for 16 h. The reaction mixture was diluted with EtOAc, washed with H₂O and brine. The organic phase was dried over Na₂SO₄, filtered and concentrated. The crude product was purified by normal phase chromatography to provide Intermediate 4A (0.92 g, 95%) as a white solid. MS(ESI) m/z 281/283 (M+H)⁺. ¹H NMR (400 MHz, CDCl₃, ppm) δ 7.58-7.43 (m, 4H), 4.31 (t, J=8.4 Hz, 1H), 3.91-3.66 (m, 2H), 2.49 (dddd, J=13.1, 8.5, 7.0, 3.5 Hz, 1H), 2.00 (dq, J=13.0, 8.4 Hz, 1H).

Intermediate 4B

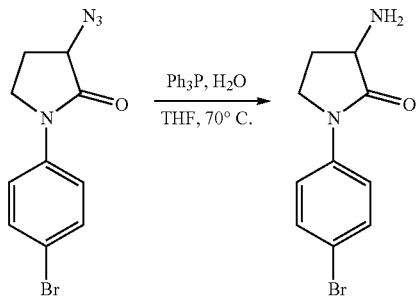 [SMILES: [N-]=[N+]=NC1CCN(c2ccc(Br)cc2)C1=O ; NC1CCN(c2ccc(Br)cc2)C1=O]

To a solution of Intermediate 4A (0.92 g, 3.27 mmol) in THF (20 mL) were added H₂O (5 ml, 278 mmol) and Ph₃P (1.29 g, 4.91 mmol) at rt. The reaction was stirred under N₂ at 70° C. for 5 h, and then it was cooled to rt. The reaction mixture was diluted with EtOAc, washed with H₂O and brine. The organic phase was dried over Na₂SO₄, filtered and concentrated. The crude product was purified by reverse phase chromatography to afford Intermediate 4 (trifluoroacetic acid salt, 0.85 g, 71%) as a white solid. MS (ESI) m/z 255/257 (M+H)⁺. ¹H NMR (400 MHz, CD₃OD) δ 7.73-7.62 (m, 2H), 7.59-7.50 (m, 2H), 4.26 (dd, J=10.9, 8.7 Hz, 1H), 4.02-3.84 (m, 2H), 2.77-2.62 (m, 1H), 2.25-2.08 (m, 1H).

Example 1: 4-[4-(2-oxo-3-phenylpyrrolidin-1-yl) phenyl]-1,2-dihydrophthalazin-1-one

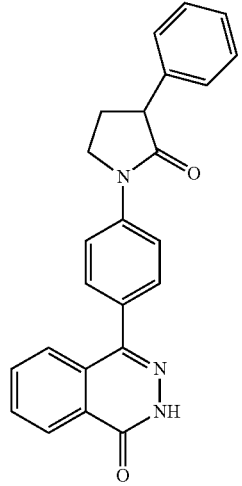 [SMILES: O=C1C(c2ccccc2)CCN1c1ccc(-c2n[nH]c(=O)c3ccccc23)cc1]

Example 1A: 3-phenylpyrrolidin-2-one

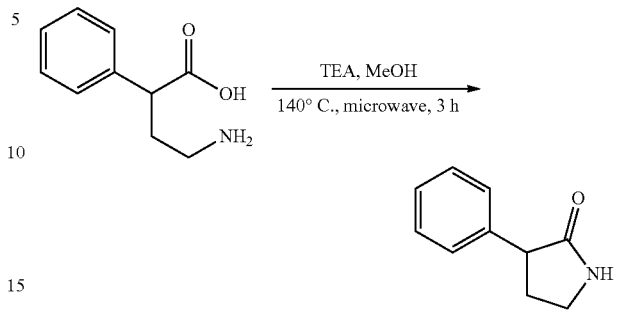

A solution of 4-amino-2-phenylbutanoic acid (250 mg, 1.40 mmol) and TEA (0.58 mL, 4.18 mmol) in MeOH (2 mL) was heated with microwave at 140° C. for 3 h. Purification by reverse phase chromatography provided Example 1A as a white solid (143 mg, 64%). MS (ESI) m/z 162 (M+H)⁺. ¹H NMR (500 MHz, CDCl₃) δ 7.54 (br. s., 1H), 7.39-7.32 (m, 2H), 7.30-7.24 (m, 3H), 7.21 (br. s., 1H), 3.68 (t, J=8.9 Hz, 1H), 3.52-3.35 (m, 2H), 2.59 (dddd, J=13.0, 9.3, 7.5, 3.9 Hz, 1H), 2.35-2.14 (m, 1H).

Example 1B:
1-(4-bromophenyl)-3-phenylpyrrolidin-2-one

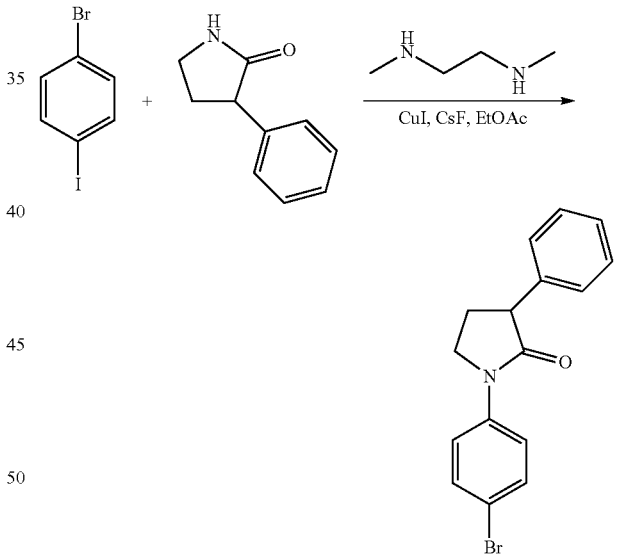

A mixture of 1-bromo-4-iodobenzene (235 mg, 0.83 mmol), Example 1A (147 mg, 0.91 mmol), copper(I) iodide (7.91 mg, 0.042 mmol), N₁,N₂-dimethylethane-1,2-diamine (7.32 mg, 0.083 mmol), cesium fluoride (315 mg, 2.08 mmol) in a sealed tube was filled with argon, and EtOAc (2 mL) was then added. The reaction was stirred at 60° C. for 16 h. The reaction was diluted with EtOAc and filtered. The solvent was removed from the filtrate. Purification by normal phase chromatography provided example 1B (180 mg, 69%) as a white solid. MS(ESI) m/z 316 (M+H)⁺; ¹H NMR (400 MHz, CDCl₃) δ 7.65-7.59 (m, 2H), 7.54-7.47 (m, 2H), 7.43-7.36 (m, 2H), 7.35-7.30 (m, 3H), 4.01-3.77 (m, 3H), 2.81-2.56 (m, 1H), 2.41-2.17 (m, 1H).

Example 1C: 3-phenyl-1-(4-(4,4,5,5-tetramethyl-1, 3,2-dioxaborolan-2-yl)phenyl)pyrrolidin-2-one Example 1: 4-[4-(2-oxo-3-phenylpyrrolidin-1-yl) phenyl]-1,2-dihydrophthalazin-1-one

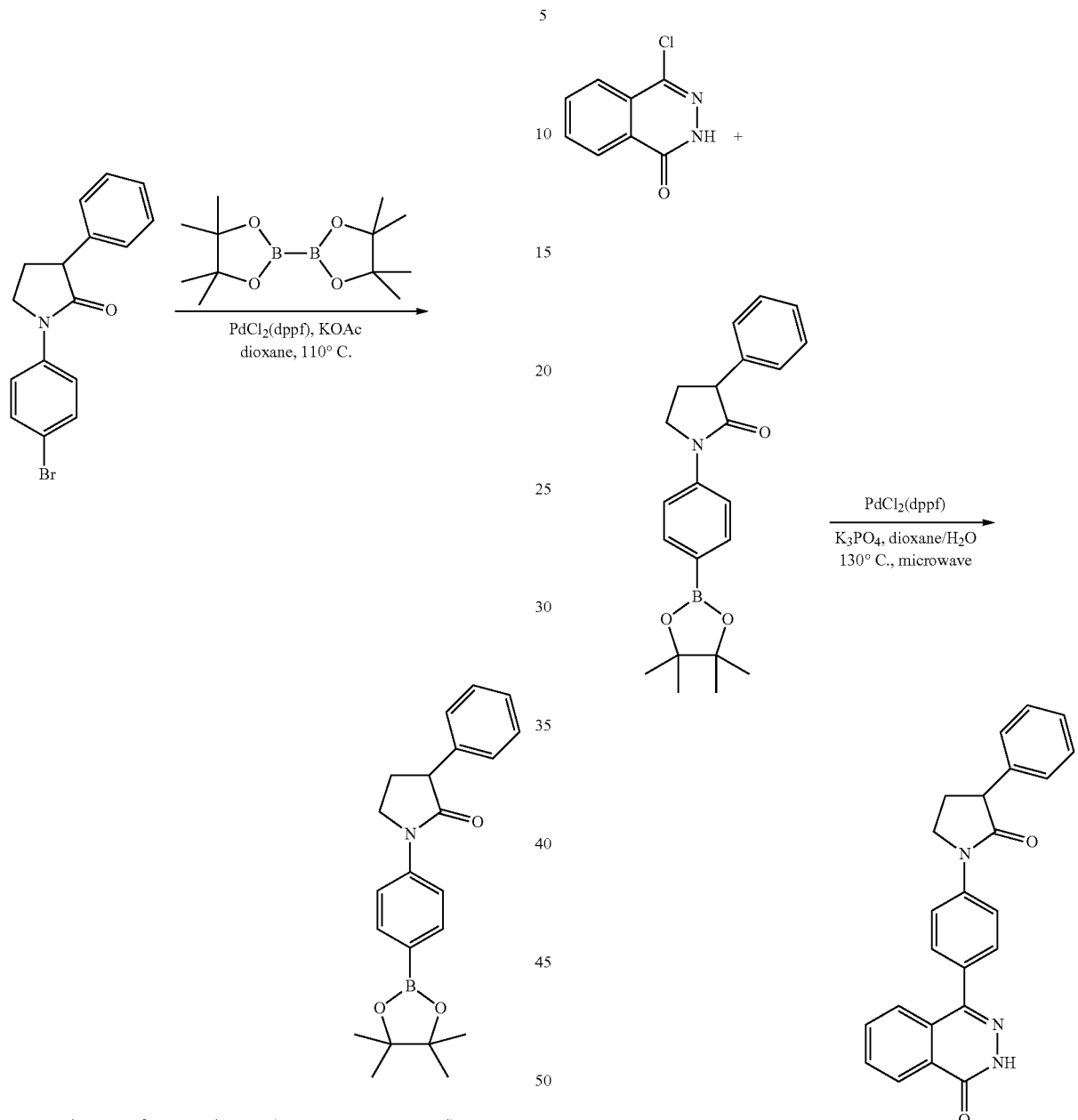

A mixture of Example 1B (105 mg, 0.33 mmol), 4,4,4', 4',5,5,5',5'-octamethyl-2,2'-bi(1,3,2-dioxaborolane) (93 mg, 0.37 mmol), KOAc (98 mg, 1.00 mmol) and PdCl$_2$(dppf)-CH$_2$Cl$_2$ adduct (7.29 mg, 9.96 μmol) in dioxane (2 mL) in a sealed vial was degassed and filled with argon. The mixture was then heated at 110° C. for 6 h. H$_2$O was added, and the reaction was extracted with EtOAc. The solvent was removed from organic phase. Purification by normal phase chromatography afforded Example 1C (65 mg, 54%) as a white solid. MS (ESI) m/z 364 (M+H)$^+$. $^1$H NMR (400 MHz, CDCl$_3$) δ 7.88-7.82 (m, 2H), 7.75-7.69 (m, 2H), 7.43-7.28 (m, 5H), 3.95 (dd, J=8.4, 5.5 Hz, 2H), 3.89 (t, J=9.0 Hz, 1H), 2.72-2.59 (m, 1H), 2.40-2.25 (m, 1H), 1.36 (s, 12H).

A microwave vial containing a solution of 4-chlorophthalazin-1(2H)-one (20 mg, 0.11 mmol), Example 1C (42 mg, 0.12 mmol) in dioxane (2 mL) were added K$_3$PO$_4$ (59 mg, 0.28 mmol), H$_2$O (0.2 mL) and PdCl$_2$(dppf)-CH$_2$Cl$_2$ (9.04 mg, 0.011 mmol) at rt. The reaction was purged with N$_2$ and then was heated with microwave at 130° C. for 15 min. The solvent was removed. Purification by reverse phase chromatography provided Example 1 (8.6 mg, 21%). MS (ESI) m/z 382.1 (M+H)$^+$. $^1$H NMR (500 MHz, DMSO-d$_6$, ppm) δ 8.44-8.27 (m, 1H), 7.98-7.83 (m, 4H), 7.72 (d, J=7.1 Hz, 1H), 7.63 (d, J=8.4 Hz, 2H), 7.43-7.22 (m, 5H), 4.12-3.97 (m, 3H), 2.71-2.58 (m, 1H), 2.23 (dd, J=12.5, 9.4 Hz, 1H). Analytical HPLC: RT=1.56 min (Method D).

Example 2: 4-[4-(2-oxo-3-phenylimidazolidin-1-yl)phenyl]-1,2-dihydrophthalazin-1-one Trifluoroacetic Acid Salt

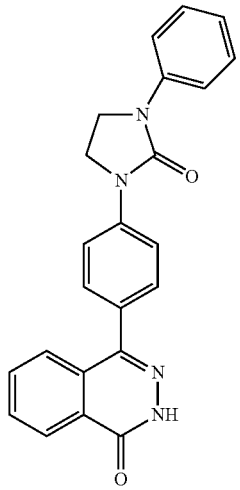 [SMILES: O=C1N(c2ccccc2)CCN1c1ccc(-c2n[nH]c(=O)c3ccccc23)cc1]

Example 2 was prepared by following a similar procedure to that described in Example 1 by replacing Example 1A with phenylimidazolidin-2-one in Example 1B. MS(ESI) m/z 383.2 (M+H)+. 1H NMR (500 MHz, DMSO-d6, ppm) δ 12.81 (s, 1H), 8.41-8.30 (m, 1H), 7.99-7.87 (m, 2H), 7.83 (d, J=8.8 Hz, 2H), 7.75 (d, J=7.2 Hz, 1H), 7.67 (d, J=8.0 Hz, 2H), 7.61 (d, J=8.8 Hz, 2H), 7.39 (t, J=8.0 Hz, 2H), 7.09 (t, J=7.3 Hz, 1H), 4.11-3.97 (m, 4H). Analytical HPLC: RT=1.73 min (Method C).

Example 3: 4-{4-[3-(2,3-dihydro-1H-indole-1-carbonyl)-2-oxopyrrolidin-1-yl]phenyl}-1,2-dihydrophthalazin-1-one

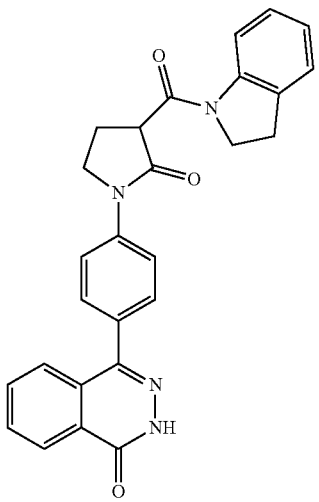 [SMILES: O=C1C(C(=O)N2CCc3ccccc32)CCN1c1ccc(-c2n[nH]c(=O)c3ccccc23)cc1]

Example 3A: 2-oxo-1-(4-(4-oxo-3,4-dihydrophthalazin-1-yl)phenyl)pyrrolidine-3-carboxylic Acid

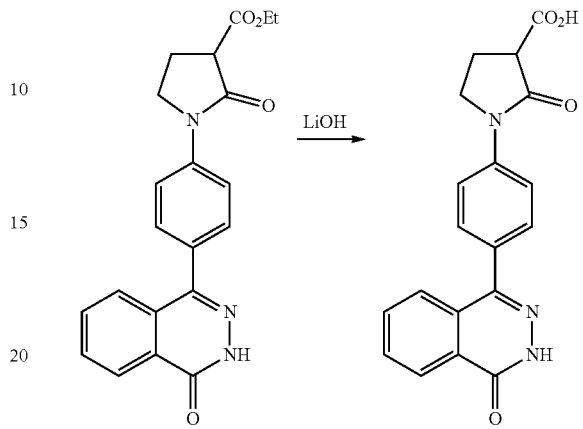

A solution of ethyl 2-oxo-1-(4-(4-oxo-3,4-dihydrophthalazin-1-yl)phenyl)pyrrolidine-3-carboxylate (33 mg, 0.087 mmol), which was prepared by following a similar procedure to that described in Example 1 by replacing Example 1A with ethyl 2-oxopyrrolidine-3-carboxylate, in THF (2 mL) was added 1.0 N LiOH (0.5 ml, 0.50 mmol). After stirring at rt for 2 h, the solvent was removed. Purification by reverse phase chromatography afforded Example 3A (12 mg, 39%) as a white solid. MS(ESI) m/z 350 (M+H)+. 1H NMR (500 MHz, CD3OD, ppm) δ 8.46-8.41 (m, 1H), 7.89-7.84 (m, 2H), 7.83-7.78 (m, 3H), 7.67-7.59 (m, 2H), 4.07 (dq, J=8.5, 4.8 Hz, 1H), 4.02-3.92 (m, 1H), 3.70-3.62 (m, 1H), 2.59-2.44 (m, 2H).

Example 3B

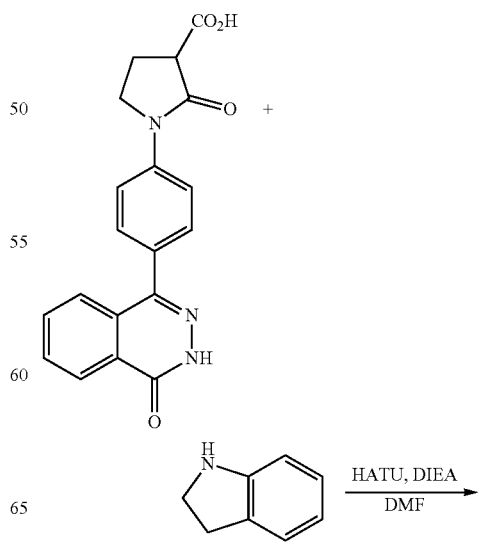

-continued

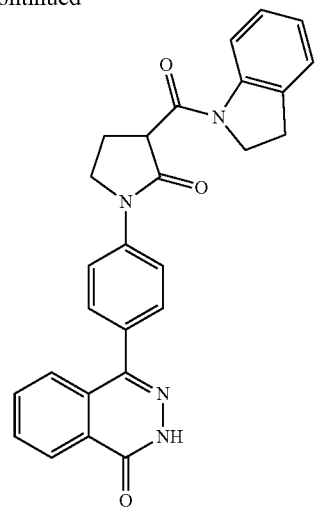

A solution of Example 3A (5 mg, 0.014 mmol), indoline (3.4 mg, 0.029 mmol), HATU (6.5 mg, 0.017 mmol) in DMF (1.5 mL) was add DIEA (0.012 mL, 0.072 mmol). The reaction was stirred at rt for 16 h. Purification by reverse phase chromatography afforded Example 3 (4.1 mg, 62%). MS(ESI) m/z 451.2 (M+H)$^+$. $^1$H NMR (500 MHz, DMSO-d$_6$, ppm) δ 12.85 (s, 1H), 8.38-8.32 (m, 1H), 8.11 (d, J=8.1 Hz, 1H), 7.94 (s, 1H), 7.92-7.83 (m, 4H), 7.71 (d, J=7.1 Hz, 1H), 7.63 (d, J=8.8 Hz, 2H), 7.28 (d, J=7.1 Hz, 1H), 7.18 (t, J=7.6 Hz, 1H), 7.09-7.00 (m, 1H), 4.49 (q, J=9.0 Hz, 1H), 4.33-4.24 (m, 2H), 4.09-3.94 (m, 2H), 3.39 (d, J=7.4 Hz, 1H), 3.20 (t, J=8.6 Hz, 2H), 2.64-2.55 (m, 1H), 2.42-2.32 (m, 1H). Analytical HPLC: RT=1.5 min (Method D).

Example 4: 4-[4-(2-oxo-4-phenylpyrrolidin-1-yl)phenyl]-1,2-dihydrophthalazin-1-one

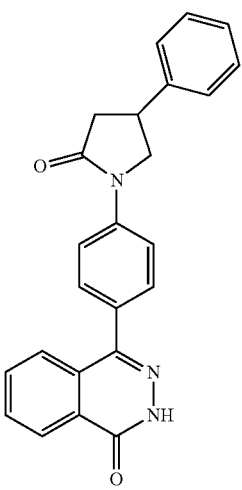 [SMILES: O=C1CC(c2ccccc2)CN1c1ccc(-c2n[nH]c(=O)c3ccccc23)cc1]

Example 4 was prepared by following a similar procedure to that described in Example 1 by replacing Example 1A with 4-phenylpyrrolidin-2-one. MS(ESI) m/z 382.1 (M+H)$^+$. $^1$H NMR (500 MHz, DMSO-d$_6$, ppm) δ 12.84 (s, 1H), 8.39-8.31 (m, 1H), 7.94-7.86 (m, 4H), 7.75-7.69 (m, 1H), 7.61 (d, J=8.4 Hz, 2H), 7.47-7.41 (m, 2H), 7.38 (t, J=7.6 Hz, 2H), 7.31-7.24 (m, 1H), 4.30 (t, J=8.8 Hz, 1H), 3.94 (t, J=8.8 Hz, 1H), 3.77 (t, J=8.6 Hz, 1H), 2.96 (dd, J=16.5, 8.4 Hz, 1H), 2.84-2.76 (m, 1H). Analytical HPLC: RT=1.52 min (Method D)

Example 5: 4{-4-[3-(2,3-dihydro-1H-isoindole-2-carbonyl)-2-oxopyrrolidin-1-yl]phenyl}-1,2-dihydrophthalazin-1-one Trifluoroacetic Acid Salt

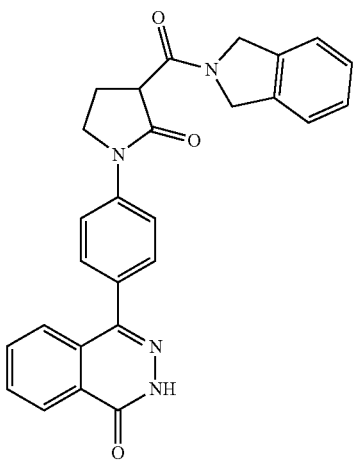 [SMILES: O=C(C1CCN(c2ccc(-c3n[nH]c(=O)c4ccccc34)cc2)C1=O)N1Cc2ccccc2C1]

Example 5 was prepared by following a similar procedure to that described in Example 3. MS(ESI) m/z 451.2 (M+H)$^+$. $^1$H NMR (500 MHz, DMSO-d$_6$, ppm) δ 12.85 (s, 1H), 8.39-8.24 (m, 1H), 7.97-7.82 (m, 4H), 7.71 (d, J=8.4 Hz, 1H), 7.62 (d, J=8.8 Hz, 2H), 7.42-7.35 (m, 2H), 7.35-7.29 (m, 2H), 5.22 (d, J=14.1 Hz, 1H), 5.04 (d, J=14.5 Hz, 1H), 4.79-4.65 (m, 2H), 4.20 (t, J=8.2 Hz, 1H), 4.10-3.93 (m, 2H), 3.47-3.33 (m, 1H), 2.60-2.52 (m, 1H), 2.36 (dd, J=8.8, 4.4 Hz, 1H). Analytical HPLC: RT=1.44 min (Method C).

Example 6: 2-oxo-1-[4-(4-oxo-3,4-dihydrophthalazin-1-yl)phenyl]-N-phenylpyrrolidine-3-carboxamide

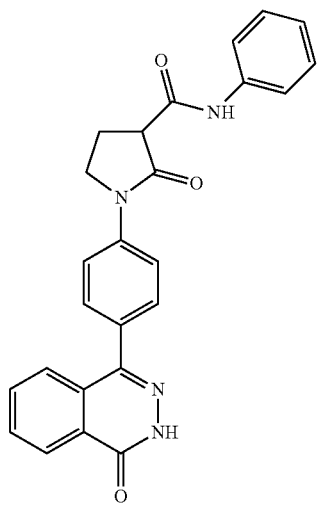 [SMILES: O=C(Nc1ccccc1)C1CCN(c2ccc(-c3n[nH]c(=O)c4ccccc34)cc2)C1=O]

Example 6 was prepared by following a similar procedure to that described in Example 3. MS(ESI) m/z 425.1 (M+H)$^+$.

¹H NMR (500 MHz, DMSO-d₆, ppm) δ 10.34 (s, 1H), 8.42-8.23 (m, 1H), 7.93-7.85 (m, 2H), 7.82 (d, J=8.8 Hz, 2H), 7.70 (d, J=8.4 Hz, 1H), 7.59 (t, J=7.6 Hz, 4H), 7.32 (t, J=7.7 Hz, 2H), 7.09 (t, J=7.2 Hz, 1H), 3.79 (t, J=8.6 Hz, 1H), 2.42 (d, J=7.7 Hz, 2H). Analytical HPLC: RT=1.39 min (Method D).

Example 7: N-benzyl-2-oxo-1-[4-(4-oxo-3,4-dihydrophthalazin-1-yl)phenyl]pyrrolidine-3-carboxamide

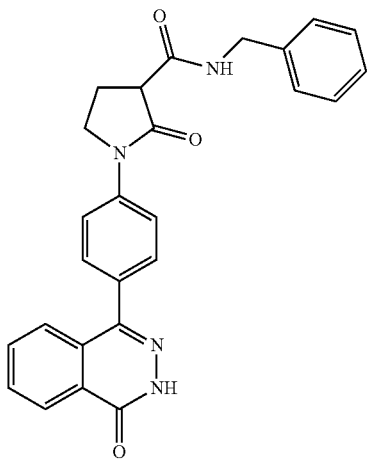 [SMILES: O=C(NCc1ccccc1)C1CCN(c2ccc(-c3n[nH]c(=O)c4ccccc34)cc2)C1=O]

Example 7 was prepared by following a similar procedure to that described in Example 3. MS(ESI) m/z 439.2 (M+H)⁺. ¹H NMR (500 MHz, DMSO-d₆, ppm) δ 8.79-8.72 (m, 1H), 8.33 (d, J=6.7 Hz, 1H), 7.90 (br. s., 2H), 7.83 (d, J=8.8 Hz, 2H), 7.70 (d, J=6.7 Hz, 1H), 7.60 (d, J=8.8 Hz, 2H), 7.35-7.27 (m, 5H), 7.23 (br. s., 2H), 4.40 (dd, J=15.3, 6.2 Hz, 1H), 4.28 (dd, J=15.3, 5.2 Hz, 1H), 4.20 (d, J=6.1 Hz, 1H), 4.11 (br. s., 1H), 3.97 (br. s., 1H), 3.91 (d, J=8.4 Hz, 1H), 2.35 (d, J=7.7 Hz, 2H). Analytical HPLC: RT=1.33 min (Method D).

Example 8: 4-[4-(1-benzyl-2-oxopyrrolidin-3-yl)phenyl]-1,2-dihydrophthalazin-1-one

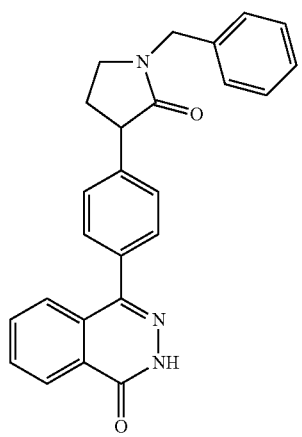 [SMILES: O=C1C(c2ccc(-c3n[nH]c(=O)c4ccccc34)cc2)CCN1Cc1ccccc1]

Example 8A: ethyl 2-(4-bromophenyl)-4-oxobutanoate

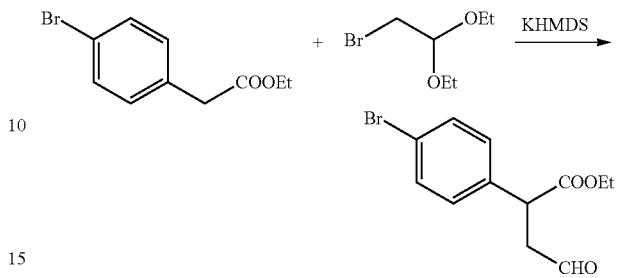

A solution of the ethyl 2-(4-bromophenyl)acetate (0.50 g, 2.1 mmol) in DMF (2 mL) was added to a solution of KHMDS (2.3 mL, 2.3 mmol). The reaction mixture was stirred at rt for 10 min before dropwise addition of 2-bromo-1,1-diethoxyethane (0.35 mL, 2.3 mmol). Then the reaction was heated at 45° C. for 2 h. The reaction was cooled to 0° C. and sat. NH₄Cl (5 mL) was added. The mixture was extracted with hexane. The organic phase was washed with H₂O and the solvent was removed. The resulted oil was suspended in H₂O (7 mL), cooled to 0° C., and treated with CHCl₃:TFA (1:1.5 mL) for 2 h. The reaction mixture was poured into a suspension of 1 M aqueous K₂CO₃ (5 mL) and CH₂Cl₂ (50 mL). Solid K₂CO₃ was added to pH 7.5. The organic phase was separated, and the aqueous layer was further extracted with CH₂Cl₂ (120 mL). The combined organic phase was washed with H₂O and brine, then dried over Na₂SO₄, filtered, and evaporated to give an oil. Normal phase chromatography afforded Example 8A (220 mg, 38%) as colorless oil. MS(ESI) m/z 285/287 (M+H)⁺. ¹H NMR (400 MHz, CDCl₃) 9.74 (s, 1H), 7.50-7.38 (m, 2H), 7.21-7.05 (m, 2H), 4.26-4.01 (m, 3H), 3.40-3.26 (m, 1H), 2.90-2.67 (m, 1H), 1.18 (t, J=7.2 Hz, 3H).

Example 8B: 1-benzyl-3-(4-bromophenyl)pyrrolidin-2-one

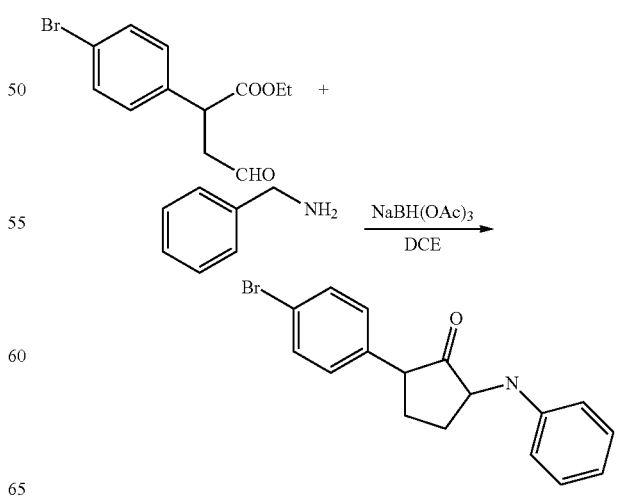

To a solution of Example 8A (115 mg, 0.40 mmol) in DCE were added benzylamine (0.053 mL, 0.48 mmol), NaBH(OAc)₃ (128 mg, 0.61 mmol) and 5 drops of AcOH. The reaction stirred rt for 16 h. The reaction was added H₂O, extracted with EtOAc, and the solvent was removed. Normal phase chromatography afforded example 8B (46 mg, 35%). MS(ESI) m/z 330/332 (M+H)⁺. ¹H NMR (500 MHz, CDCl₃) δ 7.50-7.43 (m, 2H), 7.39-7.23 (m, 5H), 7.19-7.11 (m, 2H), 4.58 (d, J=14.6 Hz, 1H), 4.46 (d, J=14.6 Hz, 1H), 3.68 (t, J=8.8 Hz, 1H), 3.36-3.22 (m, 2H), 2.56-2.40 (m, 1H), 2.09-2.00 (m, 1H)

Example 8C

Example 8 was prepared by following a similar procedure to that described in Example 1 by replacing Example 1B with Example 8B. MS(ESI) m/z 396.3 (M+H)⁺. ¹H NMR (500 MHz, DMSO-d₆, ppm) δ 12.86 (s, 1H), 8.40-8.26 (m, 1H), 7.96-7.86 (m, 2H), 7.78-7.67 (m, 1H), 7.61-7.51 (m, J=8.1 Hz, 2H), 7.49-7.41 (m, J=8.1 Hz, 2H), 7.41-7.35 (m, 2H), 7.33-7.23 (m, 3H), 4.55-4.41 (m, 2H), 3.87 (t, J=9.1 Hz, 1H), 3.41-3.29 (m, 2H), 2.56-2.52 (m, 1H), 2.10 (dq, J=12.6, 8.6 Hz, 1H). Analytical HPLC: RT=1.58 min (Method D).

Example 9: 4-[4-(2-oxo-1-phenylpyrrolidin-3-yl)phenyl]-1,2-dihydrophthalazin-1-one

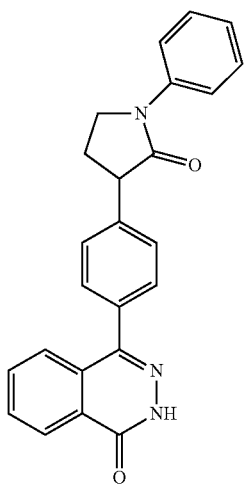

Example 9 was prepared by following a similar procedure to that described in Example 8 by replacing benzylamine with aniline in step 8B. MS(ESI) m/z 382.3 (M+H)⁺. ¹H NMR (500 MHz, DMSO-d₆, ppm) δ 12.87 (s, 1H), 8.39-8.31 (m, 1H), 7.97-7.87 (m, 2H), 7.71 (d, J=8.1 Hz, 3H), 7.64-7.55 (m, J=8.1 Hz, 2H), 7.54-7.47 (m, J=8.1 Hz, 2H), 7.40 (t, J=7.9 Hz, 2H), 7.17 (t, J=7.4 Hz, 1H), 4.06 (t, J=9.3 Hz, 1H), 3.96 (dd, J=8.4, 5.4 Hz, 2H), 2.68-2.58 (m, 1H), 2.36-2.17 (m, 1H). Analytical HPLC: RT=1.61 min (Method D).

Example 10: 4-[4-(3-benzyl-2-oxoimidazolidin-1-yl)phenyl]-1,2-dihydrophthalazin-1-one

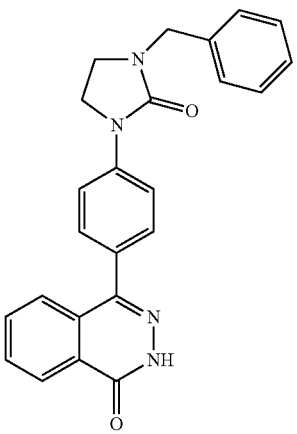 [SMILES: O=C1N(Cc2ccccc2)CCN1c1ccc(-c2n[nH]c(=O)c3ccccc23)cc1]

Example 10 was prepared by following a similar procedure to that described in Example 1 by replacing 1A with 1-benzylimidazolidin-2-one in step 1B. MS(ESI) m/z 397 (M+H)⁺. ¹H NMR (500 MHz, DMSO-d₆, ppm) δ 12.81 (s, 1H), 8.34 (d, J=7.1 Hz, 1H), 7.97-7.87 (m, 2H), 7.82-7.70 (m, 3H), 7.56 (d, J=8.8 Hz, 2H), 7.43-7.36 (m, 2H), 7.35-7.27 (m, 3H), 4.43 (s, 2H), 3.90 (t, J=8.1 Hz, 2H), 3.40 (d, J=9.8 Hz, 2H). Analytical HPLC: RT=1.66 min (Method C).

Example 11: 4-{4-[2-oxo-3-(pyridin-3-yl)imidazolidin-1-yl]phenyl}-1,2-dihydrophthalazin-1-one

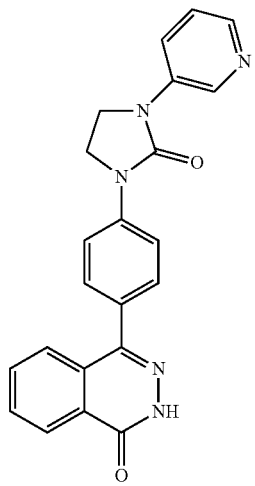 [SMILES: O=C1N(c2ccc(-c3n[nH]c(=O)c4ccccc34)cc2)CCN1c1cccnc1]

Example 11 was prepared by following a similar procedure to that described in Example 1 by replacing 1A with 1-(pyridin-3-yl)imidazolidin-2-one in step 1B. MS(ESI) m/z 384 (M+H)⁺. ¹H NMR (500 MHz, DMSO-d₆, ppm) δ 8.88 (d, J=2.0 Hz, 1H), 8.35 (d, J=7.4 Hz, 1H), 8.30 (d, J=3.7 Hz, 1H), 8.09 (d, J=8.4 Hz, 1H), 7.97-7.87 (m, 2H), 7.87-7.79 (m, J=8.8 Hz, 2H), 7.75 (d, J=7.4 Hz, 1H), 7.66-7.58 (m, J=8.4 Hz, 2H), 7.43 (dd, J=8.2, 4.5 Hz, 1H), 4.19-4.02 (m, 4H). Analytical HPLC: RT=1.16 min (Method D).

Example 12: 4-{4-[2-oxo-3-(pyridin-2-yl)imidazolidin-1-yl]phenyl}-1,2-dihydrophthalazin-1-one Trifluoroacetic Acid Salt

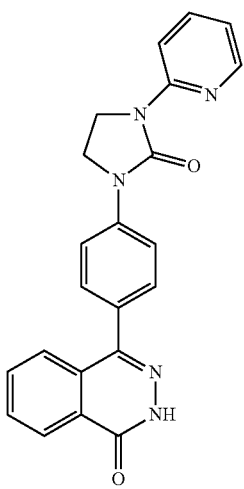 [SMILES: O=C1N(c2ccc(-c3n[nH]c(=O)c4ccccc34)cc2)CCN1c1ccccn1]

Example 12 was prepared by following a similar procedure to that described in Example 1 by replacing 1A with 1-(pyridin-2-yl)imidazolidin-2-one in step 1B. MS(ESI) m/z 384 (M+H)$^+$. $^1$H NMR (500 MHz, DMSO-d$_6$, ppm) δ 12.84 (s, 1H), 8.34 (s, 1H), 8.37 (s, 1H), 8.26 (d, J=8.8 Hz, 1H), 7.95-7.88 (m, 2H), 7.84 (d, J=8.8 Hz, 2H), 7.75 (d, J=8.1 Hz, 1H), 7.63 (d, J=8.4 Hz, 2H), 7.09 (s, 2H), 4.14 (d, J=8.4 Hz, 2H), 4.07 (d, J=8.8 Hz, 2H). Analytical HPLC: RT=1.43 min (Method D).

Example 13: 4-[4-(5-benzyl-2-oxo-1,3-oxazolidin-3-yl)phenyl]-1,2-dihydrophthalazin-1-one Trifluoroacetic Acid Salt

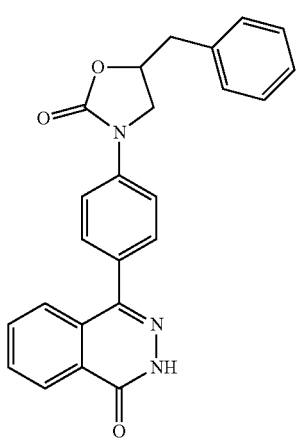 [SMILES: O=C1OC(Cc2ccccc2)CN1c1ccc(-c2n[nH]c(=O)c3ccccc23)cc1]

Example 13A: 4-(4-((2-hydroxy-3-phenylpropyl)amino)phenyl)phthalazin-1(2H)-one

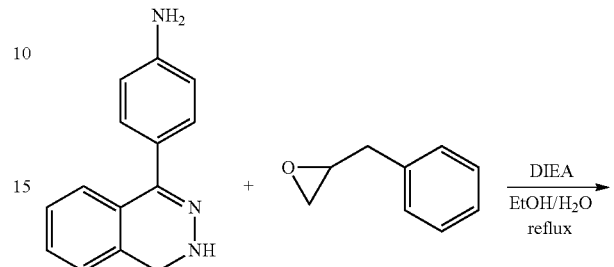

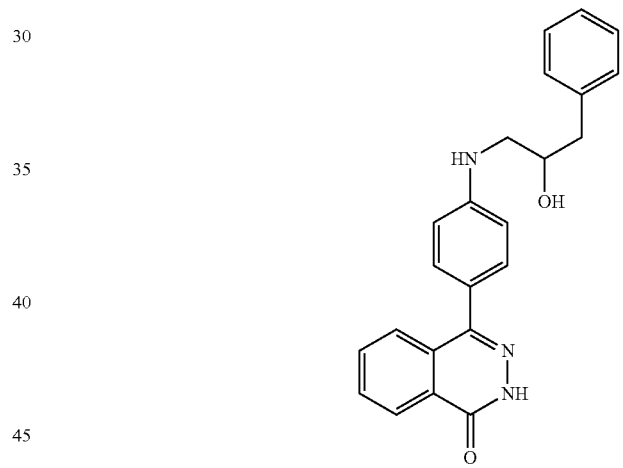

A mixture of Intermediate 1 (200 mg, 0.84 mmol), 2-benzyloxirane (136 mg, 1.01 mmol), DIEA (0.29 mL, 1.69 mmol) in EtOH (3.5 mL) and H$_2$O (3.5 mL) was refluxed for ~16 h under argon. During the reaction process, another two additional portions of 2-benzyloxirane (136 mg, 1.01 mmol) were added. After cooled to rt, the reaction was diluted with EtOAc and H$_2$O. The organic phase was separated and washed with H$_2$O and brine, dried over Na$_2$SO$_4$, filtered and concentrated. Normal phase chromatography afforded Example 13A (190 mg, 43%). MS(ESI) m/z 372 (M+H)$^+$. $^1$H NMR (400 MHz, DMSO-d$_6$) δ 12.65 (s, 1H), 8.40-8.28 (m, 1H), 7.87 (quin, J=7.5, 1.5 Hz, 2H), 7.80-7.71 (m, 1H), 7.38-7.23 (m, 6H), 7.22-7.11 (m, 1H), 6.73 (d, J=8.6 Hz, 2H), 4.01-3.84 (m, 1H), 3.22-3.09 (m, 1H), 3.07-2.97 (m, 1H), 2.90-2.80 (m, 1H), 2.77-2.65 (m, 1H).

Example 13B: 5-benzyl-3-(4-(4-oxo-3,4-dihydrophthalazin-1-yl)phenyl)oxazolidin-2-one Example 14: 4-[4-(2-oxo-4-phenyl-1,3-oxazolidin-3-yl)phenyl]-1,2-dihydrophthalazin-1-one, and
Example 15: 4-[4-(2-oxo-5-phenyl-1,3-oxazolidin-3-yl)phenyl]-1,2-dihydrophthalazin-1-one

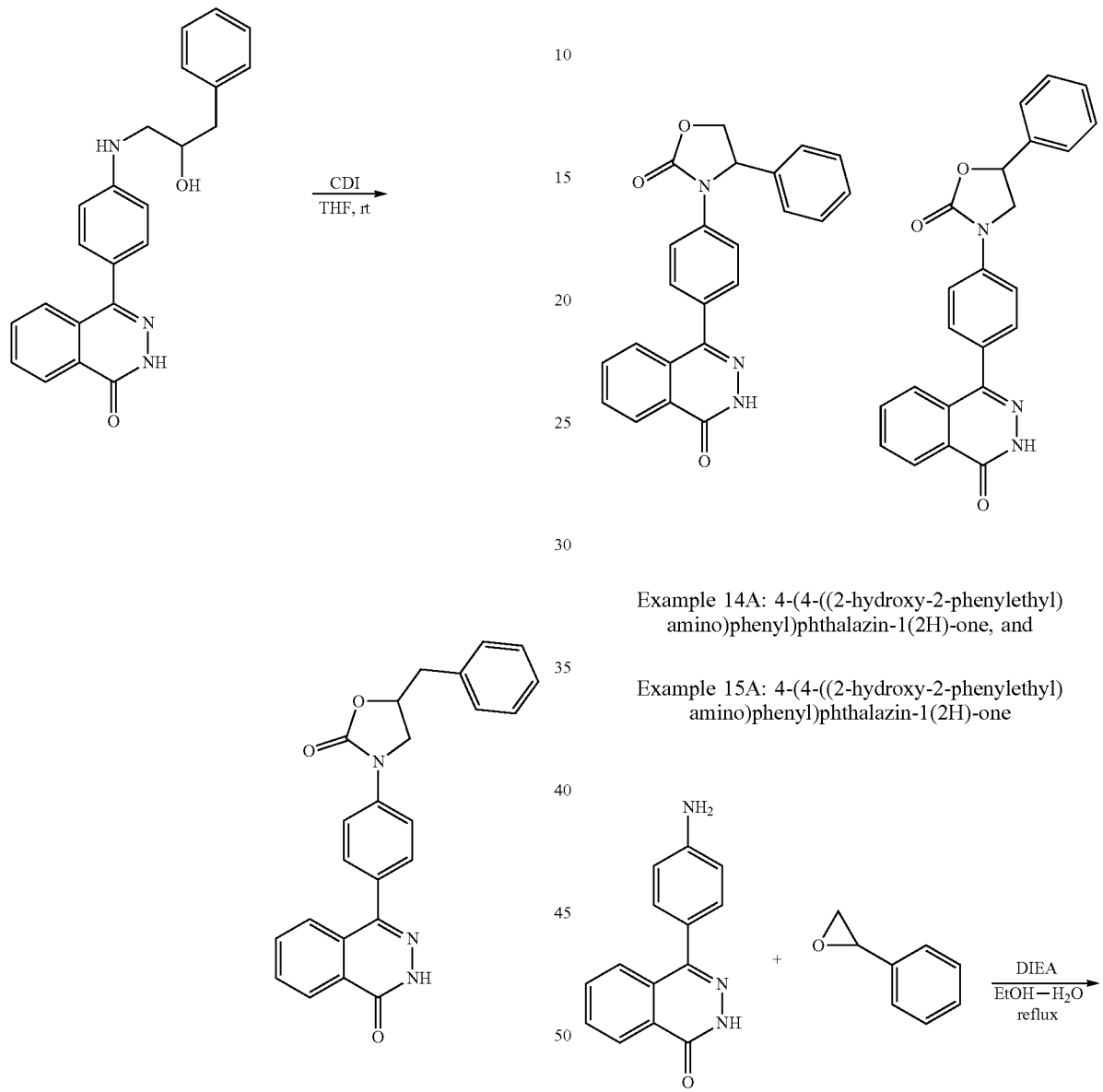

Example 14A: 4-(4-((2-hydroxy-2-phenylethyl)amino)phenyl)phthalazin-1(2H)-one, and Example 15A: 4-(4-((2-hydroxy-2-phenylethyl)amino)phenyl)phthalazin-1(2H)-one To a solution of Example 13A (140 mg, 0.26 mmol) in THF (4 mL) was added CDI (64 mg, 0.40 mmol) at rt. The mixture was stirred at rt for 3.5 h. The solvent was then removed. Purification by reverse phase chromatography afforded Example 13 (38 mg, 25%). MS(ESI) m/z 398 (M+H)+. $^1$H NMR (500 MHz, DMSO-$d_6$, ppm) δ 12.82 (s, 1H), 8.47-8.22 (m, 1H), 7.99-7.81 (m, 2H), 7.69 (d, J=8.5 Hz, 3H), 7.59 (d, J=8.5 Hz, 2H), 7.42-7.30 (m, 4H), 7.26 (dt, J=5.6, 2.9 Hz, 1H), 5.13-4.89 (m, 1H), 4.21 (t, J=8.9 Hz, 1H), 3.87 (dd, J=8.9, 6.7 Hz, 1H), 3.11 (d, J=6.1 Hz, 2H). Analytical HPLC: RT=1.68 min (Method C).

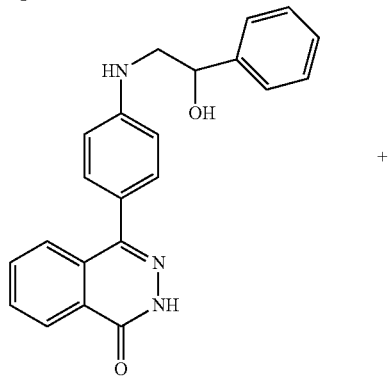

-continued

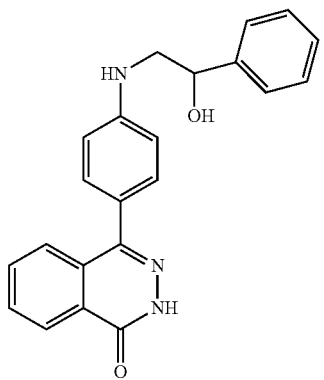

A mixture of Intermediate 1 (200 mg, 0.84 mmol), 2-phenyloxirane (0.12 mL, 1.01 mmol), DIEA (0.29 mL, 1.69 mmol) in EtOH (7 mL) and H₂O (1 mL) was refluxed for 2 h under argon. After cooled to rt, the reaction was diluted with EtOAc and H₂O. The organic phase was separated and washed with H₂O and brine, dried over Na₂SO₄, filtered and concentrated. Normal phase chromatography afforded a mixture of Example 14A and 15A (210 mg, 49%). MS(ESI) m/z 358 (M+H)⁺.

Example 14B and 15B

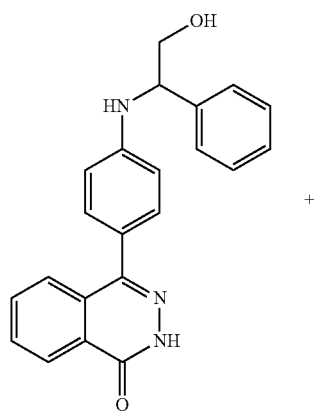

+

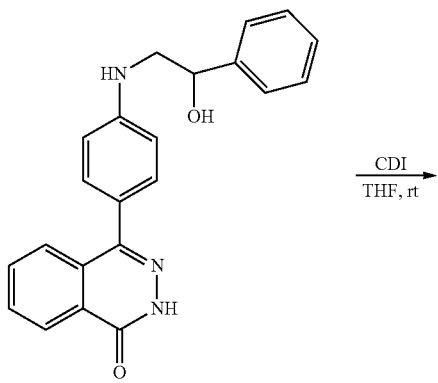

-continued

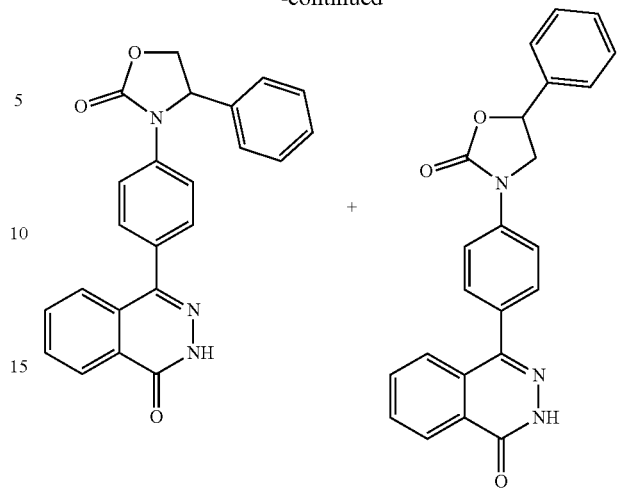

To a solution of a mixture of Example 14A and 15A (180 mg, 0.35 mmol) in THF (4 mL) were added CDI (131 mg, 0.81 mmol) and DMAP (8.6 mg, 0.071 mmol) at rt. The reaction was stirred at rt for 2 h, and then heated at 50° C. under argon for 1 h. The solvent was removed. Purification by reverse phase chromatography afforded Example 14 (15.5 mg, 11%) and Example 15 (8.5 mg, 6%).

Example 14: MS(ESI) m/z 384 (M+H)⁺. $^1$H NMR (500 MHz, DMSO-d₆) δ 12.80 (s, 1H), 8.37-8.28 (m, 1H), 7.91-7.83 (m, 2H), 7.62 (d, J=8.2 Hz, 3H), 7.52 (d, J=8.5 Hz, 2H), 7.45-7.35 (m, 4H), 7.34-7.27 (m, 1H), 5.79 (dd, 5.5 Hz, 1H), 4.88 (t, J=8.5 Hz, 1H), 4.18 (dd, J=8.5, 5.5 Hz, 1H). Analytical HPLC: RT=1.52 min (Method D).

Example 15: MS(ESI) m/z 384 (M+H)⁺. $^1$H NMR (500 MHz, DMSO-d₆, ppm) δ 12.83 (s, 1H), 8.40-8.29 (m, 1H), 7.97-7.86 (m, 2H), 7.78 (d, J=8.5 Hz, 2H), 7.71 (d, J=7.0 Hz, 1H), 7.63 (d, J=8.5 Hz, 2H), 7.57-7.52 (m, 2H), 7.50-7.38 (m, 3H), 5.81 (t, J=8.1 Hz, 1H), 4.57 (t, J=9.0 Hz, 1H), 4.09 (t, J=8.4 Hz, 1H). Analytical HPLC: RT=1.63 min (Method D).

Example 16: tert-butyl N-({2-oxo-3-[4-(4-oxo-3,4-dihydrophthalazin-1-yl)phenyl]-1,3-oxazolidin-5-yl}methyl)carbamate

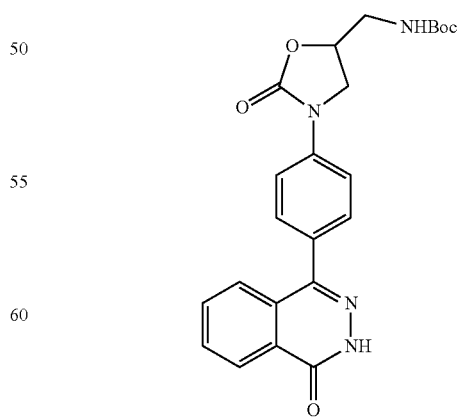

Example 16 was prepared by following a similar procedure to that described in Example 13 by replacing 2-benzyloxirane with tert-butyl (oxiran-2-ylmethyl)carbamate in 13A. MS(ESI) m/z 437 (M+H)+. $^1$H NMR (500 MHz, DMSO-$d_6$, ppm) δ 12.82 (s, 1H), 8.42-8.28 (m, 1H), 7.98-7.86 (m, 2H), 7.77-7.68 (m, 3H), 7.66-7.58 (m, 2H), 7.33-7.17 (m, 1H), 4.82-4.68 (m, 1H), 4.21 (t, J=8.9 Hz, 1H), 3.90 (dd, J=9.0, 5.9 Hz, 1H), 3.33 (t, J=5.2 Hz, 2H), 1.37 (s, 9H). Analytical HPLC: RT=6.94 min (Method B).

Example 17: 4-[4-(2-oxo-5-propyl-1,3-oxazolidin-3-yl)phenyl]-1,2-dihydrophthalazin-1-one

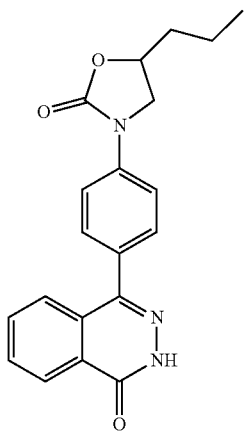 [SMILES: CCCC1CN(c2ccc(-c3n[nH]c(=O)c4ccccc34)cc2)C(=O)O1]

Example 17 was prepared by following a similar procedure to that described in Example 13 by replacing 2-benzyloxirane with 2-propyloxirane in 13A. MS(ESI) m/z 350 (M+H)+. $^1$H NMR (500 MHz, DMSO-$d_6$, ppm) δ 8.43-8.25 (m, 1H), 7.95-7.81 (m, 2H), 7.76-7.67 (m, 3H), 7.60 (d, J=8.5 Hz, 2H), 4.73 (quin, J=6.9 Hz, 1H), 4.21 (t, J=8.7 Hz, 1H), 3.77 (t, J=8.1 Hz, 1H), 1.83-1.61 (m, 2H), 1.43 (td, J=14.6, 7.3 Hz, 2H), 0.94 (t, J=7.3 Hz, 3H). Analytical HPLC: RT=1.59 min (Method C).

Example 18: N-({2-oxo-3-[4-(4-oxo-3,4-dihydrophthalazin-1-yl)phenyl]-1,3-oxazolidin-5-yl}methyl)benzamide Example 18A: 5-(aminomethyl)-3-(4-(4-oxo-3,4-dihydrophthalazin-1-yl)phenyl)oxazolidin-2-one Trifluoroacetic Acid Salt

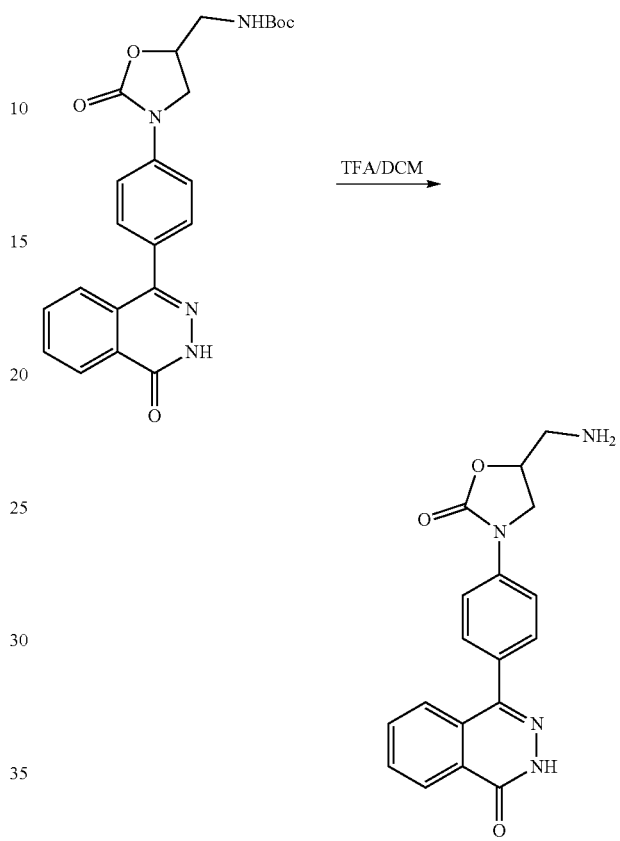

To a solution of Example 16 (10 mg, 0.023 mmol) in DCM (1.6 mL) was added TFA (0.40 mL). The reaction mixture was stirred at rt under argon for 25 min, and the solvent was removed to afford Example 18A (7.0 mg, 68% yield) as an off-white solid. MS (ESI) m/z 337 (M+H)+.

Example 18B

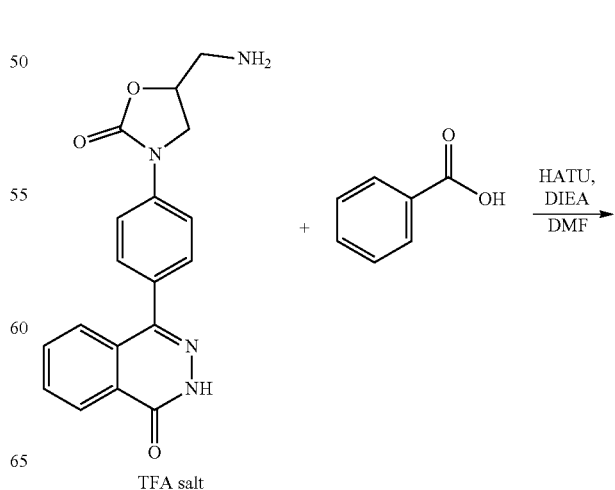

-continued

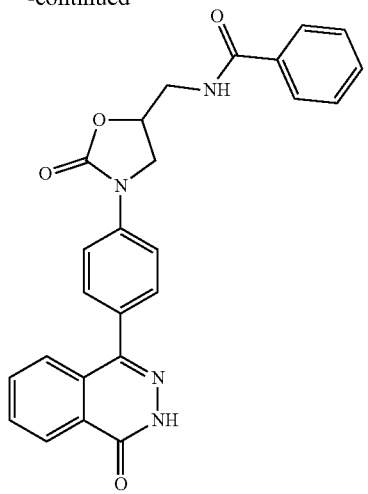

To a solution of Example 18A (7.0 mg, 0.016 mmol) in DMF (1 mL) were added benzoic acid (3.80 mg, 0.031 mmol), HATU (8.86 mg, 0.023 mmol), and DIPEA (0.014 mL, 0.078 mmol). The reaction mixture was stirred under argon at rt for 70 min. Purification by reverse phase chromatography provided Example 18 (4.4 mg, 64%). MS(ESI) m/z 441 (M+H)$^+$. $^1$H NMR (500 MHz, DMSO-d$_6$, ppm) δ 12.83 (s, 1H), 8.86 (t, J=5.6 Hz, 1H), 8.51-8.25 (m, 1H), 7.96-7.86 (m, 2H), 7.83 (d, J=7.3 Hz, 2H), 7.72 (d, J=8.5 Hz, 2H), 7.68 (d, J=7.0 Hz, 1H), 7.61 (d, J=8.5 Hz, 2H), 7.56-7.50 (m, 1H), 7.49-7.41 (m, 2H), 4.92 (dd, J=8.5, 5.2 Hz, 1H), 4.26 (t, J=8.9 Hz, 1H), 3.97 (dd, J=9.0, 6.0 Hz, 1H), 3.76-3.61 (m, 2H). Analytical HPLC: RT=1.32 min (Method D).

Example 19: 4-{4-[5-(4-fluorophenyl)-2-oxo-1,3-oxazolidin-3-yl]phenyl}-1,2-dihydrophthalazin-1-one

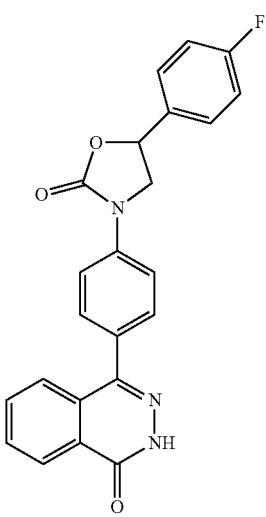 [SMILES: O=C1OC(c2ccc(F)cc2)CN1c1ccc(-c2n[nH]c(=O)c3ccccc23)cc1]

Example 19 was prepared by following a similar procedure to that described in Example 13 by replacing 2-benzyloxirane with 2-(4-fluorophenyl)oxirane in 13A. MS(ESI) m/z 402.1 (M+H)$^+$. $^1$H NMR (500 MHz, DMSO-d$_6$, ppm) δ 8.40-8.30 (m, 1H), 7.97-7.85 (m, 2H), 7.75 (d, J=8.5 Hz, 2H), 7.69 (d, J=7.0 Hz, 1H), 7.64-7.52 (m, 4H), 7.28 (t, J=8.7 Hz, 2H), 5.80 (t, J=8.1 Hz, 1H), 4.53 (t, J=9.0 Hz, 1H), 4.06 (t, J=8.4 Hz, 1H). Analytical HPLC: RT=1.51 min (Method D).

Example 20: 4-(4-{5-[(4-methanesulfonylphenyl)methyl]-2-oxo-1,3-oxazolidin-3-yl}phenyl)-1,2-dihydrophthalazin-1-one

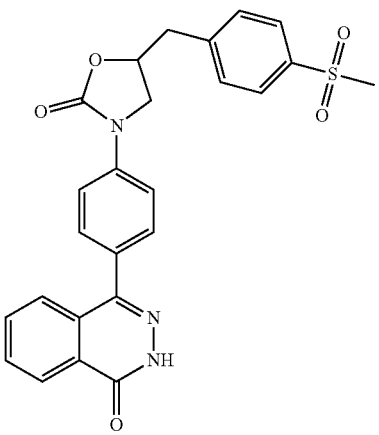 [SMILES: CS(=O)(=O)c1ccc(CC2CN(c3ccc(-c4n[nH]c(=O)c5ccccc45)cc3)C(=O)O2)cc1]

Example 20 was prepared by following a similar procedure to that described in Example 13 by replacing 2-benzyloxirane with 2-(4-(methylsulfonyl)benzyl)oxirane in 13A. MS(ESI) m/z 476 (M+H)$^+$. $^1$H NMR (500 MHz, DMSO-d$_6$, ppm) δ 12.83 (s, 1H), 8.40-8.28 (m, 1H), 7.98-7.79 (m, 4H), 7.73-7.53 (m, 7H), 5.11-4.99 (m, 1H), 4.26 (t, J=8.7 Hz, 1H), 3.94-3.86 (m, 1H), 3.29-3.18 (m, 2H), 3.17 (s, 3H). Analytical HPLC: RT=1.32 min (Method C).

Example 21: 4-[4-(2-oxo-octahydro-1,3-benzoxazol-3-yl)phenyl]-1,2-dihydrophthalazin-1-one

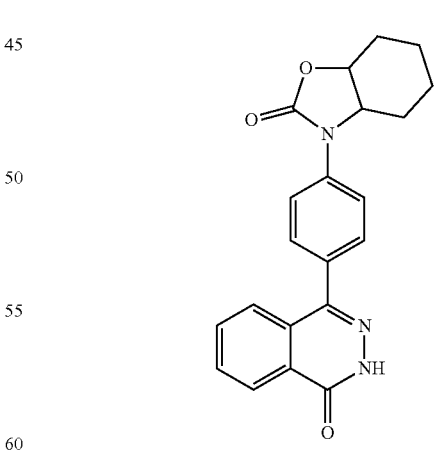

Example 21 was prepared by following a similar procedure to that described in Example 13 by replacing 2-benzyloxirane with 7-oxabicyclo[4.1.0]heptane in 13A. MS(ESI) m/z 362 (M+H)$^+$. $^1$H NMR (500 MHz, DMSO-d$_6$, ppm) δ 12.87 (s, 1H), 8.46-8.29 (m, 1H), 7.99-7.85 (m, 2H), 7.80-7.70 (m, 1H), 7.64 (d, J=8.6 Hz, 2H), 7.47 (d, J=8.6 Hz, 2H), 4.13 (td, J=11.3, 3.5 Hz, 1H), 3.95 (td, J=10.9, 3.0 Hz, 1H), 2.19 (t, J=12.2 Hz, 2H), 1.89 (d, J=7.3 Hz, 1H), 1.83-1.64 (m, 2H), 1.57-1.32 (m, 3H). Analytical HPLC: RT=10.5 min (Method A).

Example 22: 4-{4-[2-oxo-5-(2,2,2-trifluoro-1-hydroxy-1-phenylethyl)-1,3-oxazolidin-3-yl]phenyl}-1,2-dihydrophthalazin-1-one

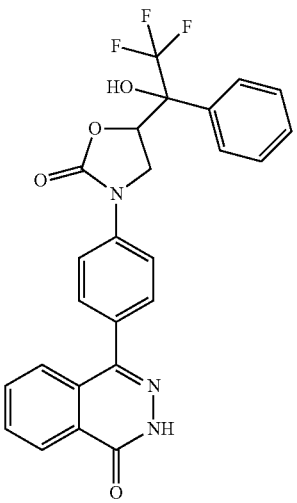 [SMILES: O=C1OC(C(O)(c2ccccc2)C(F)(F)F)CN1c1ccc(-c2n[nH]c(=O)c3ccccc23)cc1]

Example 20 was prepared by following a similar procedure to that described in Example 13 by replacing 2-benzyloxirane with 2,2,2-trifluoro-1-(oxiran-2-yl)-1-phenylethanol in 13A. MS(ESI) m/z 482 (M+H)$^+$. $^1$H NMR (500 MHz, DMSO-d$_6$, ppm) δ 12.80 (s, 1H), 8.34-8.24 (m, 1H), 7.89-7.79 (m, 2H), 7.63 (d, J=8.4 Hz, 5H), 7.57-7.38 (m, 6H), 5.69 (dd, J=8.9, 7.4 Hz, 1H), 3.85 (t, J=9.1 Hz, 1H), 3.51 (t, J=8.0 Hz, 1H). Analytical HPLC: RT=1.74 min (Method C).

Example 23: 4-{4-[(4R,5S)-5-methyl-2-oxo-4-phenyl-1,3-oxazolidin-3-yl]phenyl}-1,2-dihydrophthalazin-1-one

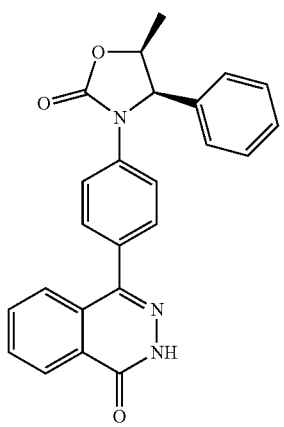 [SMILES: C[C@@H]1OC(=O)N(c2ccc(-c3n[nH]c(=O)c4ccccc34)cc2)[C@@H]1c1ccccc1]

Example 20 was prepared by following a similar procedure to that described in Example 13 by replacing 2-benzyloxirane with (2S,3S)-2-methyl-3-phenyloxirane in 13A. MS(ESI) m/z 398 (M+H)$^+$. $^1$H NMR (500 MHz, DMSO-d$_6$, ppm) δ 12.79 (s, 1H), 8.34-8.16 (m, 1H), 7.91-7.73 (m, 2H), 7.63 (d, J=8.5 Hz, 2H), 7.60-7.54 (m, 1H), 7.47 (d, J=8.5 Hz, 2H), 7.41-7.34 (m, 2H), 7.33-7.27 (m, 1H), 7.23 (d, J=7.0 Hz, 2H), 5.71 (d, J=7.6 Hz, 1H), 5.16-5.06 (m, 1H), 0.85 (d, J=6.4 Hz, 3H). Analytical HPLC: RT=1.63 min (Method C).

Example 24: 4-{4-[3-(morpholin-4-yl)-2-oxopyrrolidin-1-yl]phenyl}-1,2-dihydrophthalazin-1-one

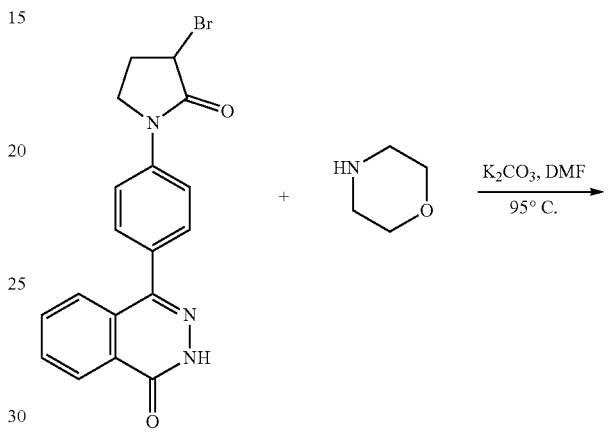

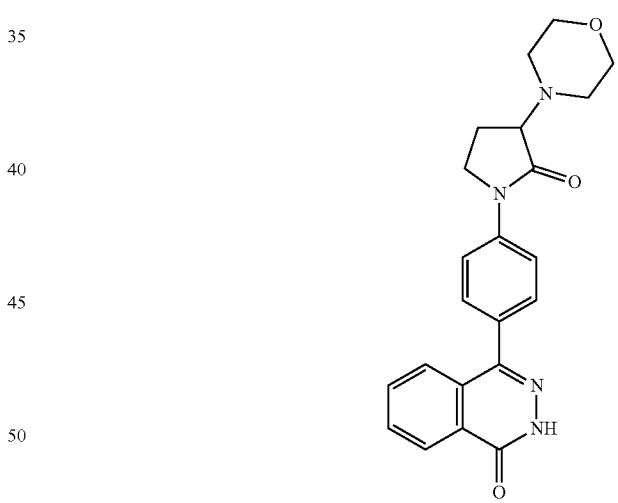

To a solution of Intermediate 3 (20 mg, 0.052 mmol) in DMF (1 mL) were added K$_2$CO$_3$ (36 mg, 0.26 mmol) and morpholine (4.5 mg, 0.052 mmol) at rt. The reaction was stirred under N$_2$ at 95° C. for 1 h. After cooled to rt, the reaction was filtered. Purification by reverse phase chromatography provided Example 24 (2.9 mg, 13%). MS(ESI) m/z 391 (M+H)$^+$. $^1$H NMR (500 MHz, DMSO-d$_6$, ppm) δ 12.83 (s, 1H), 8.42-8.24 (m, 1H), 7.95-7.81 (m, 4H), 7.70 (d, J=8.5 Hz, 1H), 7.61 (d, J=8.5 Hz, 2H), 3.88-3.75 (m, 2H), 3.65-3.54 (m, 4H), 3.47 (br. s., 1H), 2.94-2.80 (m, 2H), 2.57-2.51 (m, 2H), 2.31-2.18 (m, 1H), 2.14-2.00 (m, 1H). Analytical HPLC: RT=1.15 min (Method D).

Example 25: 4-{4-[3-(benzylamino)-2-oxopyrrolidin-1-yl]phenyl}-1,2-dihydrophthalazin-1-one Trifluoroacetic Acid Salt

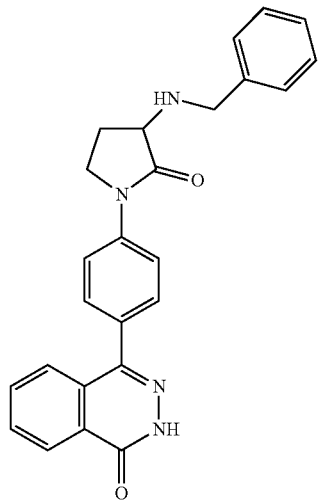 [SMILES: O=C1C(NCc2ccccc2)CCN1c1ccc(-c2n[nH]c(=O)c3ccccc23)cc1]

Example 25 was prepared by following a similar procedure to that described in Example 24 by replacing morpholine with benzylamine. MS(ESI) m/z 411 (M+H)+. 1H NMR (500 MHz, DMSO-$d_6$, ppm) δ 12.86 (s, 1H), 8.37-8.26 (m, 1H), 7.93-7.86 (m, 2H), 7.80 (d, J=8.5 Hz, 2H), 7.69 (d, J=9.2 Hz, 1H), 7.62 (d, J=8.5 Hz, 2H), 7.47 (br. s., 2H), 7.43 (d, J=5.2 Hz, 3H), 4.58-3.76 (m, 5H), 2.60 (br. s., 1H), 2.25-2.09 (m, 1H). Analytical HPLC: RT=1.53 min (Method D).

Example 26: 4-(4-{3-[(3-methoxyphenyl)amino]-2-oxopyrrolidin-1-yl}phenyl)-1,2-dihydrophthalazin-1-one

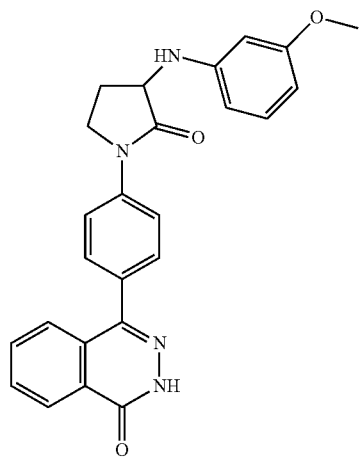 [SMILES: COc1cccc(NC2CCN(c3ccc(-c4n[nH]c(=O)c5ccccc45)cc3)C2=O)c1]

Example 26 was prepared by following a similar procedure to that described in Example 24 by replacing morpholine with 3-methoxyaniline. MS(ESI) m/z 427 (M+H)+. 1H NMR (500 MHz, DMSO-$d_6$, ppm) δ 12.86 (s, 1H), 8.32 (d, J=6.7 Hz, 1H), 7.95-7.85 (m, 2H), 7.82 (d, J=8.9 Hz, 2H), 7.71 (d, J=8.8 Hz, 1H), 7.59 (d, J=8.5 Hz, 2H), 6.99 (t, J=7.9 Hz, 1H), 6.29 (d, J=7.6 Hz, 1H), 6.24 (s, 1H), 6.18 (d, J=8.2 Hz, 1H), 5.75 (d, J=6.4 Hz, 1H), 4.50-3.82 (m, 2H), 3.64 (s, 3H), 2.59 (br. s., 1H), 1.99-1.84 (m, 1H). Analytical HPLC: RT=1.61 min (Method D).

Example 27: 4-{4-[2-oxo-3-(phenylamino)pyrrolidin-1-yl]phenyl}-1,2-dihydrophthalazin-1-one Trifluoroacetic Acid Salt

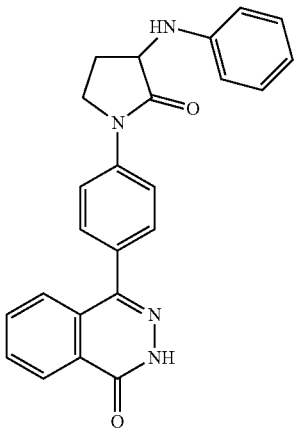 [SMILES: O=C1C(Nc2ccccc2)CCN1c1ccc(-c2n[nH]c(=O)c3ccccc23)cc1]

Example 27 was prepared by following a similar procedure to that described in Example 24 by replacing morpholine with aniline. MS(ESI) m/z 397 (M+H)+. 1H NMR (500 MHz, DMSO-$d_6$, ppm) δ 8.32 (d, J=7.1 Hz, 1H), 7.95-7.86 (m, 2H), 7.84 (d, J=8.4 Hz, 2H), 7.71 (d, J=8.1 Hz, 1H), 7.59 (d, J=8.4 Hz, 2H), 7.09 (t, J=7.7 Hz, 2H), 6.69 (d, J=7.7 Hz, 2H), 6.59 (t, J=7.2 Hz, 1H), 4.44-4.33 (m, 1H), 4.13-4.08 (m, 1H), 3.87 (d, J=8.4 Hz, 1H), 2.61 (br. s., 1H), 2.02-1.83 (m, 1H). Analytical HPLC: RT=1.60 min (Method C).

Example 28: 4-{4-[3-(cyclopentylamino)-2-oxopyrrolidin-1-yl]phenyl}-1,2-dihydrophthalazin-1-one Trifluoroacetic Acid Salt

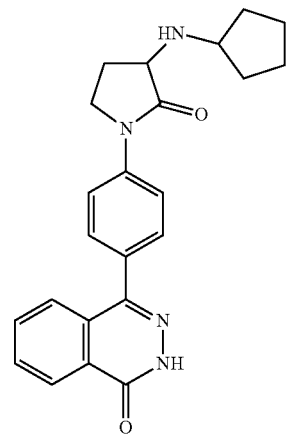 [SMILES: O=C1C(NC2CCCC2)CCN1c1ccc(-c2n[nH]c(=O)c3ccccc23)cc1]

Example 28 was prepared by following a similar procedure to that described in Example 24 by replacing morpholine with cyclopentylamine. MS(ESI) m/z 389 (M+H)+. 1H NMR (500 MHz, DMSO-$d_6$, ppm) δ 12.89 (s, 1H), 8.40-8.28 (m, 1H), 7.99-7.82 (m, 4H), 7.75-7.59 (m, 3H), 4.38 (t, J=9.6 Hz, 1H), 4.08-3.89 (m, 2H), 2.65 (d, J=7.4 Hz, 1H), 2.15 (t, J=10.4 Hz, 1H), 2.04 (br. s., 2H), 1.84-1.35 (m, 7H). Analytical HPLC: RT=1.06 min (Method C).

Example 29: 4-(4-{3-[(2,3-dihydro-1H-inden-2-yl)amino]-2-oxopyrrolidin-1-yl}phenyl)-1,2-dihydrophthalazin-1-one

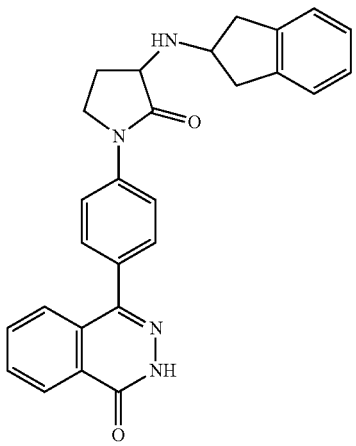 [SMILES: O=C1C(NC2Cc3ccccc3C2)CCN1c1ccc(-c2n[nH]c(=O)c3ccccc23)cc1]

Example 29 was prepared by following a similar procedure to that described in Example 24 by replacing morpholine with 2-aminoindane. MS(ESI) m/z 437 (M+H)⁺. ¹H NMR (500 MHz, DMSO-$d_6$, ppm) δ 12.88 (s, 1H), 8.34 (dd, J=6.4, 2.7 Hz, 1H), 7.90 (t, J=2.9 Hz, 2H), 7.87 (d, J=8.9 Hz, 2H), 7.72-7.68 (m, 1H), 7.64 (d, J=8.5 Hz, 2H), 7.27-7.21 (m, 2H), 7.19-7.14 (m, 2H), 3.91 (br. s., 4H), 3.31-3.21 (m, 2H), 3.03-2.88 (m, 2H), 2.63 (br. s., 1H), 2.13-1.98 (m, 1H). Analytical HPLC: RT=1.29 min (Method C).

Example 30: 4-[4-(3-{[3-(difluoromethoxy)phenyl]amino}-2-oxopyrrolidin-1-yl)phenyl]-1,2-dihydrophthalazin-1-one

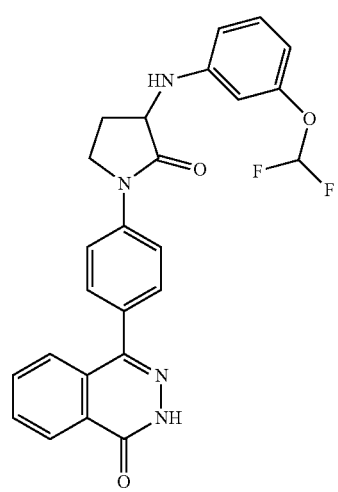 [SMILES: O=C1C(Nc2cccc(OC(F)F)c2)CCN1c1ccc(-c2n[nH]c(=O)c3ccccc23)cc1]

Example 30A, 1-(4-bromophenyl)-3-((3-(difluoromethoxy)phenyl)amino)pyrrolidin-2-one

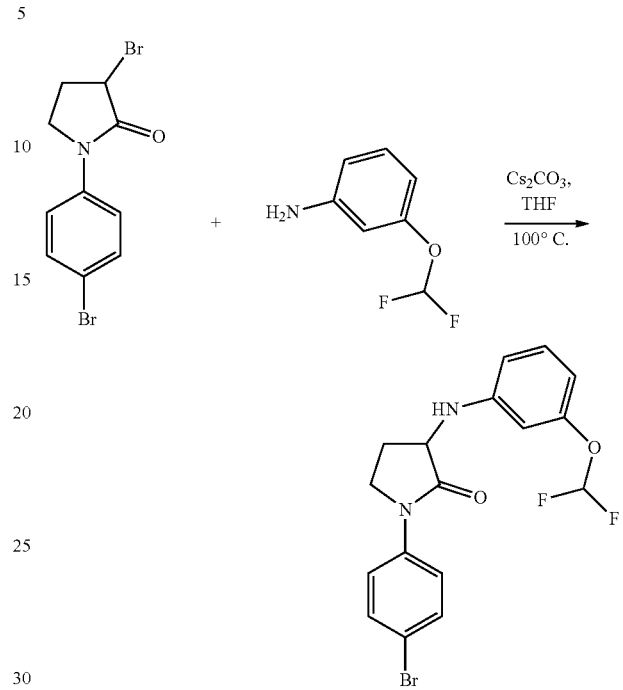

To a solution of Intermediate 2 (100 mg, 0.31 mmol) in THF (2 mL) and H₂O (0.3 mL) were added 3-(difluoromethoxy)aniline (50 mg, 0.31 mmol) and Cs₂CO₃ (102 mg, 0.31 mmol) at rt. The reaction in a sealed tube was stirred under N₂ at 100° C. for 24 h. The sovents were removed. Purification by normal phase chromatography provided Example 30A (65 mg, 52%) as a white solid. MS(ESI) m/z 397/399 (M+H)⁺. ¹H NMR (400 MHz, CDCl₃) δ 7.60-7.46 (m, 4H), 7.18 (t, J=8.1 Hz, 1H), 6.55 (ddd, J=10.3, 8.3, 1.9 Hz, 2H), 6.45 (t, J=2.1 Hz, 1H), 6.50 (t, J=73.9 Hz, 1H), 4.20 (dd, J=10.6, 7.9 Hz, 1H), 3.96-3.78 (m, 2H), 2.86 (dddd, J=12.5, 7.9, 6.2, 1.5 Hz, 1H), 2.12-2.00 (m, 1H).

Example 30B, 3-((3-(difluoromethoxy)phenyl)amino)-1-(4-(4,4,5,5-tetramethyl-1,3,2-dioxaborolan-2-yl)phenyl)pyrrolidin-2-one

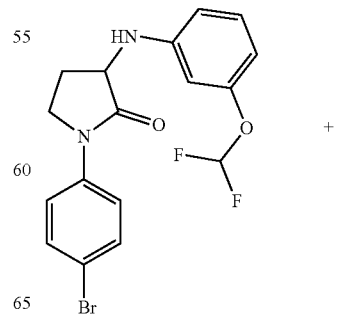

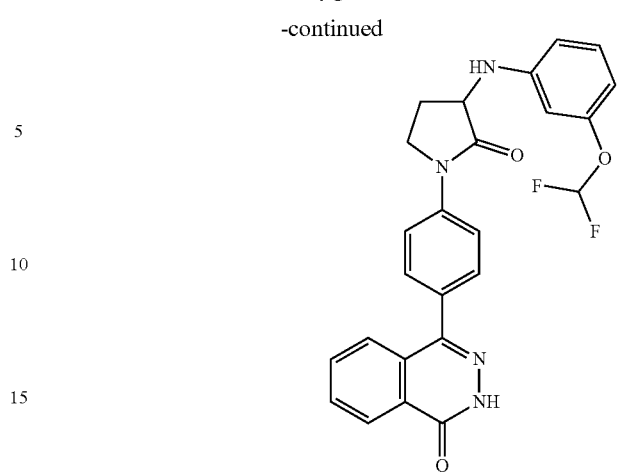

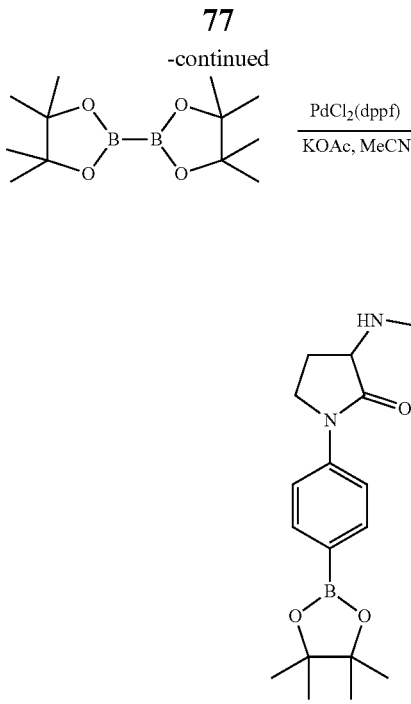

To a solution of Example 30A (65 mg, 0.16 mmol) in acetonitrile (4 mL) were added 4,4,4',4',5,5,5',5'-octamethyl-2,2'-bi(1,3,2-dioxaborolane) (46 mg, 0.18 mmol), KOAc (32 mg, 0.33 mmol) and PdCl$_2$(dppf) (12 mg, 0.016 mmol) at rt. The reaction was stirred under N$_2$ at 90° C. for 1 h. The reaction was cooled to rt and the solvent was removed to afford a crude product of Example 30B. MS(ESI) m/z 445 (M+H)$^+$.

Example 30C

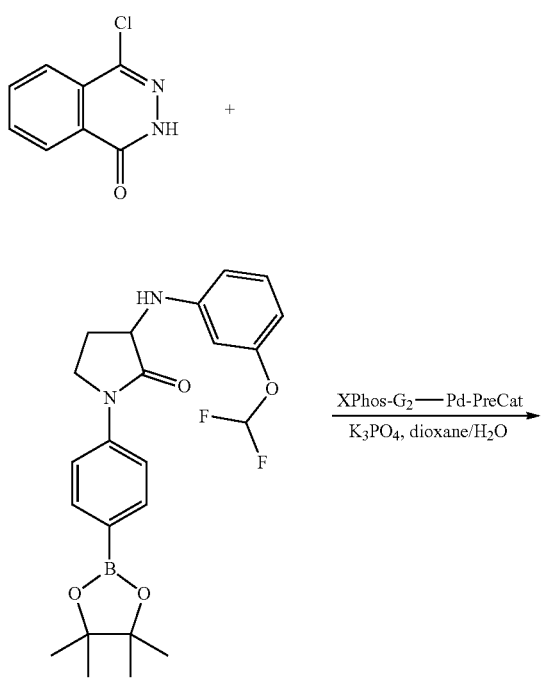

To a solution of Example 30B (44 mg, 0.10 mmol) in dioxane (2 mL) and H$_2$O (0.5 mL) were added 4-chlorophthalazin-1(2H)-one (18 mg, 0.10 mmol), K$_3$PO$_4$ (43 mg, 0.20 mmol) and Xphos-Precatalyst 2$^{nd}$ generation (8 mg, 0.01 mmol) at rt. The reaction was heated with an oil bath at 90° C. for 1 h. The solvent was removed. Purification by reverse phase chromatography afforded Example 30 (38 mg, 82%). MS(ESI) m/z 463 (M+H)$^+$. $^1$H NMR (500 MHz, DMSO-d$_6$, ppm) δ 8.42-8.27 (m, 1H), 7.98-7.85 (m, 4H), 7.77-7.68 (m, 1H), 7.64 (d, J=8.5 Hz, 2H), 7.12 (d, J=7.9 Hz, 1H), 7.12 (t, J=74.2 Hz, 1H), 6.60 (d, J=7.9 Hz, 1H), 6.52 (s, 1H), 6.36 (d, J=7.9 Hz, 1H), 6.31 (d, J=7.3 Hz, 1H), 4.56-4.42 (m, 1H), 4.00-3.82 (m, 2H), 2.70-2.59 (m, 1H), 2.01-1.89 (m, 1H). Analytical HPLC: RT=1.76 min (Method D).

Example 31: 4-(4-{3-[(2-ethylphenyl)amino]-2-oxopyrrolidin-1-yl}phenyl)-1,2-dihydrophthalazin-1-one 1

Example 31 was prepared by following a similar procedure to that described in Example 30 by replacing 3-(difluoromethoxy)aniline with 2-ethylaniline in Example 30A. MS(ESI) m/z 425 (M+H)$^+$. $^1$H NMR (500 MHz, DMSO-d$_6$, ppm) δ 12.85 (s, 1H), 8.42-8.28 (m, 1H), 8.01-7.86 (m, 4H), 7.73 (d, J=7.6 Hz, 1H), 7.65 (d, J=8.5 Hz, 2H), 7.09-6.98 (m, 2H), 6.75 (d, J=7.9 Hz, 1H), 6.63 (t, J=7.3 Hz, 1H), 5.07 (d, J=6.4 Hz, 1H), 4.54-4.36 (m, 1H), 4.04-3.85 (m, 2H), 3.47-3.28 (m, 2H), 2.70 (dt, J=11.7, 6.0 Hz, 1H), 2.11-1.97 (m, 1H), 1.19 (t, J=7.5 Hz, 3H). Analytical HPLC: RT=1.94 min (Method C).

Example 32: 4-(4-{3-[(3-fluoro-5-methoxyphenyl)amino]-2-oxopyrrolidin-1-yl}phenyl)-1,2-dihydrophthalazin-1-one

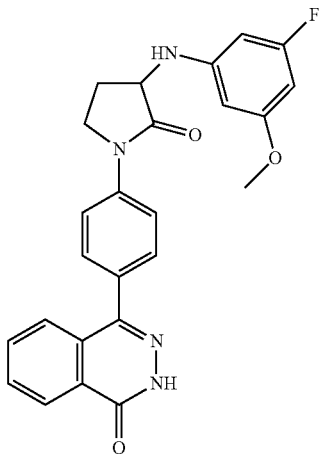 [SMILES: COc1cc(F)cc(NC2CCN(c3ccc(-c4n[nH]c(=O)c5ccccc45)cc3)C2=O)c1]

Example 32 was prepared by following a similar procedure to that described in Example 30 by replacing 3-(difluoromethoxy)aniline with 3-fluoro-5-methoxyaniline in Example 30A. MS(ESI) m/z 445 (M+H)$^+$. $^1$H NMR (500 MHz, DMSO-d$_6$, ppm) δ 12.83 (s, 1H), 8.35 (d, J=7.0 Hz, 1H), 7.90 (d, J=8.2 Hz, 4H), 7.72 (d, J=7.3 Hz, 1H), 7.64 (d, J=8.5 Hz, 2H), 6.33 (d, J=7.3 Hz, 1H), 6.20-6.09 (m, 2H), 6.00 (d, J=11.0 Hz, 1H), 4.46 (q, J=8.3 Hz, 1H), 3.90 (dd, J=17.5, 8.1 Hz, 2H), 3.69 (s, 3H), 2.64 (br. s., 1H), 1.99-1.84 (m, 1H). Analytical HPLC: RT=1.73 min (Method C).

Example 33: 4-(4-{3-[(2H-1,3-benzodioxol-5-yl)amino]-2-oxopyrrolidin-1-yl}phenyl)-1,2-dihydrophthalazin-1-one 1

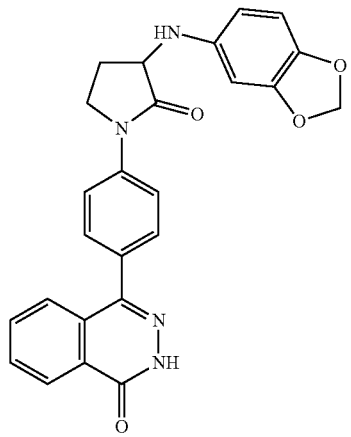 [SMILES: O=C1C(Nc2ccc3c(c2)OCO3)CCN1c1ccc(-c2n[nH]c(=O)c3ccccc23)cc1]

Example 33 was prepared by following a similar procedure to that described in Example 30 by replacing 3-(difluoromethoxy)aniline with benzo[d][1,3]dioxol-5-amine in Example 30A. MS(ESI) m/z 441 (M+H)$^+$. $^1$H NMR (500 MHz, DMSO-d$_6$, ppm) δ 12.83 (s, 1H), 8.34 (d, J=6.7 Hz, 1H), 7.98-7.84 (m, 4H), 7.71 (d, J=7.3 Hz, 1H), 7.63 (d, J=8.2 Hz, 2H), 6.68 (d, J=8.2 Hz, 1H), 6.46 (s, 1H), 6.17 (d, J=7.0 Hz, 1H), 5.85 (s, 2H), 5.67 (d, J=6.4 Hz, 1H), 4.32 (q, J=8.0 Hz, 1H), 3.99-3.76 (m, 2H), 2.70-2.59 (m, 1H), 1.98-1.84 (m, 1H). Analytical HPLC: RT=1.40 min (Method C).

Example 34: 4-(4-{3-[(3,4-dihydro-2H-1,5-benzodioxepin-7-yl)amino]-2-oxopyrrolidin-1-yl}phenyl)-1,2-dihydrophthalazin-1-one

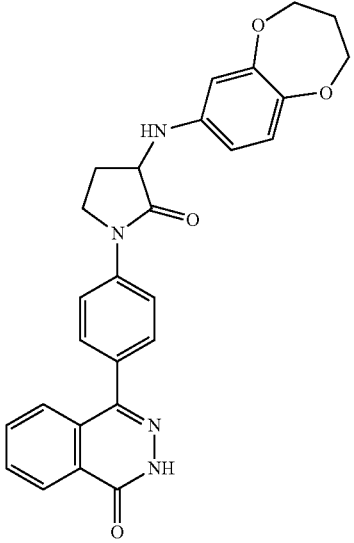 [SMILES: O=C1C(Nc2ccc3c(c2)OCCCO3)CCN1c1ccc(-c2n[nH]c(=O)c3ccccc23)cc1]

Example 34 was prepared by following a similar procedure to that described in Example 30 by replacing 3-(difluoromethoxy)aniline with 3,4-dihydro-2H-benzo[b][1,4]dioxepin-7-amine in Example 30A. MS(ESI) m/z 469 (M+H)$^+$. $^1$H NMR (500 MHz, DMSO-d$_6$, ppm) δ 12.83 (s, 1H), 8.41-8.27 (m, 1H), 7.98-7.83 (m, 4H), 7.76-7.68 (m, 1H), 7.63 (d, J=8.5 Hz, 2H), 6.74 (d, J=8.5 Hz, 1H), 6.38 (d, J=2.7 Hz, 1H), 6.32 (dd, J=8.5, 2.7 Hz, 1H), 5.72 (d, J=7.0 Hz, 1H), 4.38-4.27 (m, 1H), 4.03 (d, J=3.7 Hz, 2H), 3.95 (t, J=5.2 Hz, 2H), 3.92-3.82 (m, 2H), 2.67-2.56 (m, 1H), 2.07-1.97 (m, 2H), 1.95-1.83 (m, 1H). Analytical HPLC: RT=1.49 min (Method C).

Example 35: 4-(4-{3-[(3-cyclopropyl-1-methyl-1H-pyrazol-5-yl)amino]-2-oxopyrrolidin-1-yl}phenyl)-1,2-dihydrophthalazin-1-one

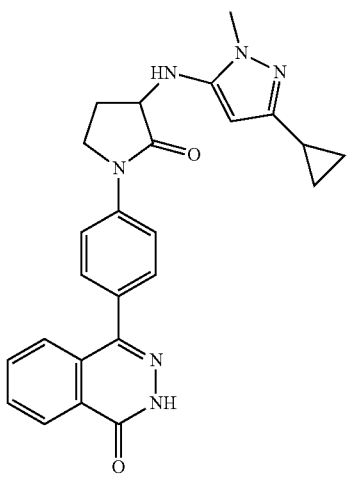 [SMILES: Cn1nc(C2CC2)cc1NC1CCN(c2ccc(-c3n[nH]c(=O)c4ccccc34)cc2)C1=O]

Example 35 was prepared by following a similar procedure to that described in Example 30 by replacing 3-(difluoromethoxy)aniline with 3-cyclopropyl-1-methyl-1H-pyrazol-5-amine in Example 30A. MS(ESI) m/z 441.2 (M+H)⁺. ¹H NMR (500 MHz, DMSO-d₆) 12.84 (s, 1H), 8.41-8.27 (m, 1H), 7.96-7.87 (m, 4H), 7.76-7.69 (m, 1H), 7.65 (d, J=8.5 Hz, 2H), 5.22 (s, 1H), 4.29-4.13 (m, 1H), 3.98-3.79 (m, 2H), 3.48 (s, 3H), 2.63-2.53 (m, 1H), 2.07-1.94 (m, 1H), 1.76-1.62 (m, 1H), 0.84-0.69 (m, 2H), 0.63-0.46 (m, 2H). Analytical HPLC: RT=1.18 min (Method C).

Example 36: 4-(4-{3-[(3-cyclopropyl-5-methyl-1H-pyrazol-4-yl)amino]-2-oxopyrrolidin-1-yl}phenyl)-1,2-dihydrophthalazin-1-one

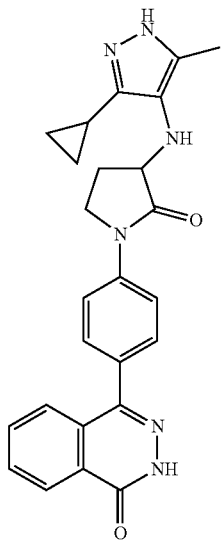 [SMILES: Cc1[nH]nc(C2CC2)c1NC1CCN(c2ccc(-c3n[nH]c(=O)c4ccccc34)cc2)C1=O]

Example 36 was prepared by following a similar procedure to that described in Example 30 by replacing 3-(difluoromethoxy)aniline with 3-cyclopropyl-5-methyl-1H-pyrazol-4-amine in Example 30A. MS(ESI) m/z 441 (M+H)⁺. ¹H NMR (500 MHz, DMSO-d₆, ppm) δ 1H NMR (500 MHz, DMSO-d₆) δ 12.84 (s, 1H), 8.42-8.30 (m, 1H), 7.98-7.84 (m, 4H), 7.78-7.69 (m, 1H), 7.64 (d, J=8.5 Hz, 2H), 4.05-3.88 (m, 3H), 3.51 (s, 3H), 2.45 (dt, J=8.5, 4.2 Hz, 1H), 2.27-2.14 (m, 1H), 1.71-1.55 (m, 1H), 0.87-0.70 (m, 3H), 0.70-0.56 (m, 1H). Analytical HPLC: RT=1.13 min (Method C).

Example 37: 4-(4-{3-[(2-fluoro-5-methoxyphenyl)amino]-2-oxopyrrolidin-1-yl}phenyl)-1,2-dihydrophthalazin-1-one

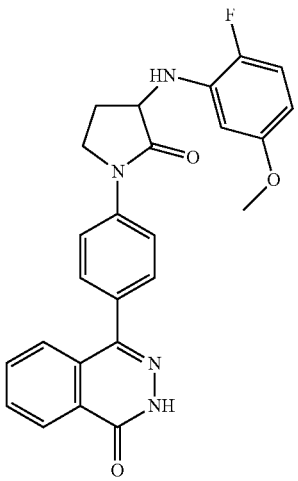 [SMILES: COc1ccc(F)c(NC2CCN(c3ccc(-c4n[nH]c(=O)c5ccccc45)cc3)C2=O)c1]

Example 37 was prepared by following a similar procedure to that described in Example 30 by replacing 3-(difluoromethoxy)aniline with 2-fluoro-5-methoxyaniline in Example 30A. MS(ESI) m/z 445 (M+H)⁺. ¹H NMR (500 MHz, DMSO-d₆, ppm) δ 12.84 (s, 1H), 8.41-8.27 (m, 1H), 7.99-7.86 (m, 4H), 7.73 (d, J=7.3 Hz, 1H), 7.65 (d, J=8.5 Hz, 2H), 6.97 (dd, J=11.4, 9.0 Hz, 1H), 6.48 (dd, J=7.3, 2.7 Hz, 1H), 6.20-6.09 (m, 1H), 5.73 (d, J=7.9 Hz, 1H), 4.67-4.48 (m, 1H), 4.04-3.84 (m, 2H), 3.70 (s, 3H), 2.67-2.57 (m, 1H), 2.16-2.05 (m, 1H). Analytical HPLC: RT=1.73 min (Method C).

Example 38: 4-(4-{3-[(3-methoxy-5-methylphenyl)amino]-2-oxopyrrolidin-1-yl}phenyl)-1,2-dihydrophthalazin-1-one Trifluoroacetic Acid Salt

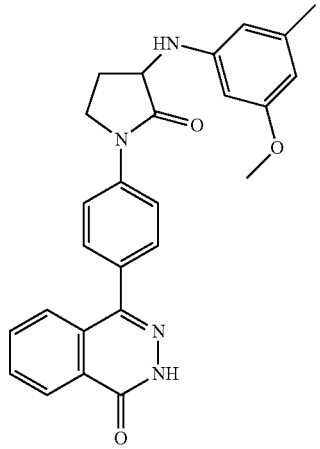 [SMILES: COc1cc(C)cc(NC2CCN(c3ccc(-c4n[nH]c(=O)c5ccccc45)cc3)C2=O)c1]

Example 38 was prepared by following a similar procedure to that described in Example 30 by replacing 3-(difluoromethoxy)aniline with 3-methoxy-5-methylaniline in Example 30A. MS(ESI) m/z 441 (M+H)+. 1H NMR (500 MHz, DMSO-d6, ppm) δ 12.83 (s, 1H), 8.35 (d, J=7.3 Hz, 1H), 7.98-7.83 (m, 4H), 7.72 (d, J=7.3 Hz, 1H), 7.64 (d, J=8.2 Hz, 2H), 6.15 (s, 1H), 6.12 (s, 1H), 6.02 (s, 1H), 5.85 (d, J=7.3 Hz, 1H), 4.47-4.34 (m, 1H), 3.97-3.83 (m, 2H), 3.67 (s, 3H), 2.69-2.59 (m, 1H), 2.17 (s, 3H), 1.99-1.86 (m, 1H). Analytical HPLC: RT=1.69 min (Method C).

Example 39: 4-(4-{2-oxo-3-[(1-phenyl-1H-pyrazol-4-yl)amino]pyrrolidin-1-yl}phenyl)-1,2-dihydrophthalazin-1-one

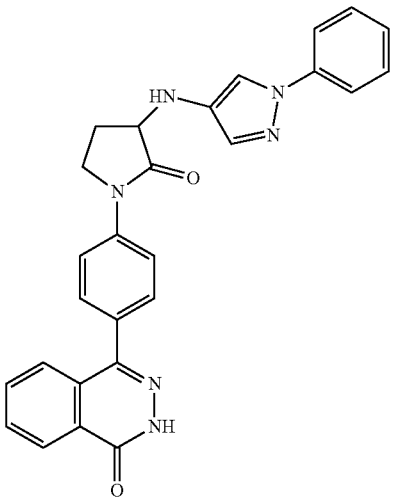 [SMILES: O=C1C(Nc2cnn(-c3ccccc3)c2)CCN1c1ccc(-c2n[nH]c(=O)c3ccccc23)cc1]

Example 39 was prepared by following a similar procedure to that described in Example 30 by replacing 3-(difluoromethoxy)aniline with 1-phenyl-1H-pyrazol-4-amine in Example 30A. MS(ESI) m/z 463 (M+H)+. 1H NMR (500 MHz, DMSO-d6, ppm) δ 12.83 (s, 1H), 8.35 (d, J=7.3 Hz, 1H), 7.98-7.85 (m, 5H), 7.77-7.68 (m, 3H), 7.64 (d, J=8.5 Hz, 2H), 7.49-7.40 (m, 3H), 7.21 (t, J=7.3 Hz, 1H), 5.23 (d, J=5.8 Hz, 1H), 4.19-4.08 (m, 1H), 3.99-3.92 (m, 1H), 3.91-3.83 (m, 1H), 2.80-2.67 (m, 1H), 2.03-1.88 (m, 1H). Analytical HPLC: RT=1.51 min (Method C).

Example 40: 4-(4-{3-[(2,4-difluoro-3-methoxyphenyl)amino]-2-oxopyrrolidin-1-yl}phenyl)-1,2-dihydrophthalazin-1-one

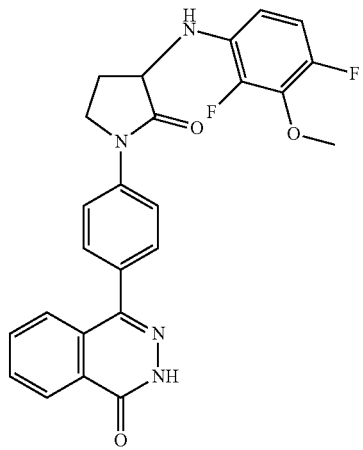 [SMILES: COc1c(F)ccc(NC2CCN(c3ccc(-c4n[nH]c(=O)c5ccccc45)cc3)C2=O)c1F]

Example 40 was prepared by following a similar procedure to that described in Example 30 by replacing 3-(difluoromethoxy)aniline with 2,4-difluoro-3-methoxyaniline in Example 30A. MS(ESI) m/z 463 (M+H)+. 1H NMR (500 MHz, DMSO-d6, ppm) δ 12.83 (s, 1H), 8.34 (d, J=7.0 Hz, 1H), 7.90 (d, J=7.3 Hz, 4H), 7.71 (d, J=7.0 Hz, 1H), 7.64 (d, J=7.9 Hz, 2H), 6.46 (d, J=10.7 Hz, 2H), 6.37 (d, J=6.7 Hz, 1H), 4.43 (d, J=8.5 Hz, 1H), 3.99-3.82 (m, 2H), 3.75 (s, 3H), 2.64 (br. s., 1H), 1.91 (quin, J=9.9 Hz, 1H). Analytical HPLC: RT=1.71 min (Method D).

Example 41: 4-[4-(4-benzyl-5-oxo-4,5-dihydro-1H-1,2,4-triazol-1-yl)phenyl]-1,2-dihydrophthalazin-1-one Trifluoroacetic Acid Salt

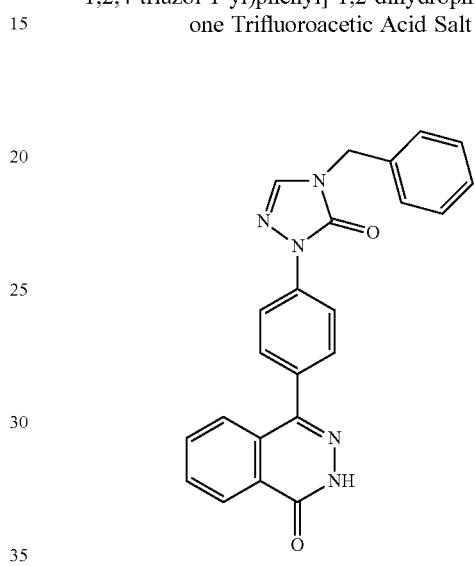

Example 41A, 4-benzyl-1H-1,2,4-triazol-5(4H)-one

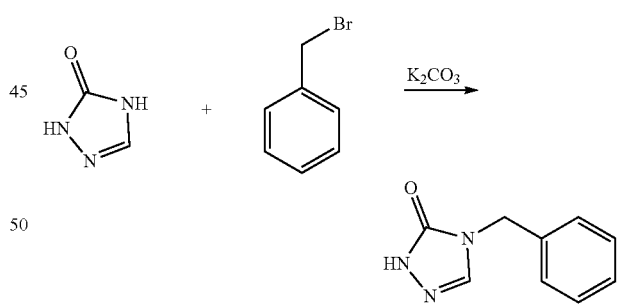

To a solution of 1H-1,2,4-triazol-5(4H)-one (70 mg, 0.82 mmol) in DMF (7 mL) was added K2CO3 (227 mg, 1.65 mmol), and then benzyl bromide (0.10 mL, 0.82 mmol) was added dropwise over 10 min at rt. The reaction was stirred at rt for 24 h. The reaction mixture was diluted with MeOH and filtered. The solvent was removed from the filtrate. Purification by reverse phase chromatography afforded Example 41A (130 mg, 90%). MS(ESI) m/z 176 (M+H)+. 1H NMR (400 MHz, DMSO-d6) δ 11.72 (br. s., 1H), 7.96 (d, J=1.3 Hz, 1H), 7.40-7.33 (m, 2H), 7.33-7.23 (m, 3H), 4.75 (s, 2H).

Example 41B, 4-benzyl-1-(4-(4,4,5,5-tetramethyl-1,3,2-dioxaborolan-2-yl)phenyl)-1H-1,2,4-triazol-5(4H)-one

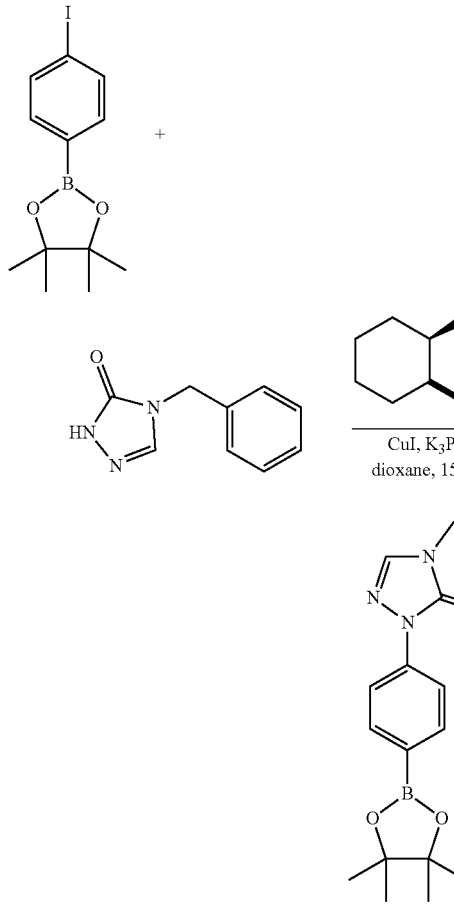

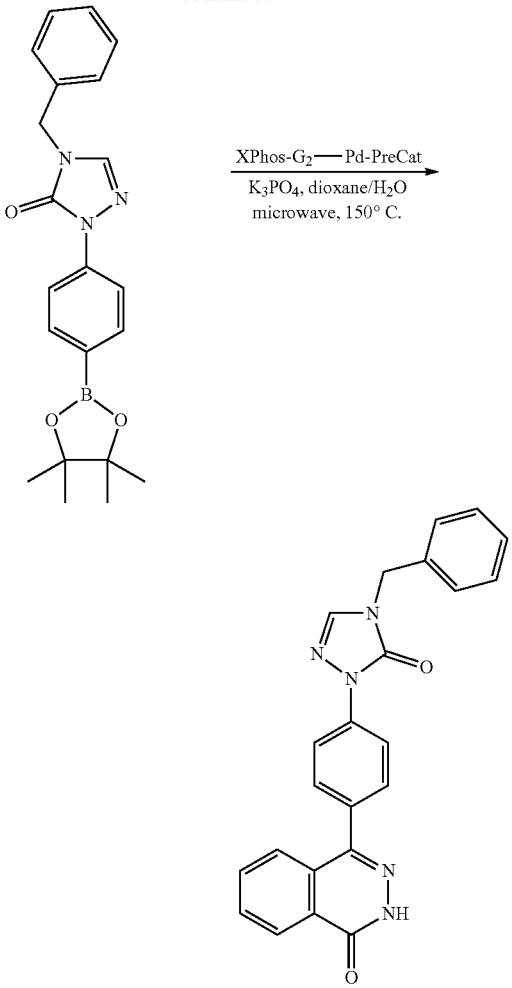

A vial was charged with dioxane (2 mL), CuI (5.4 mg, 0.029 mmol), (1R,2R)—N1,N2-dimethylcyclohexane-1,2-diamine (16 mg, 0.11 mmol), $K_3PO_4$ (133 mg, 0.63 mmol), 2-(4-iodophenyl)-4,4,5,5-tetramethyl-1,3,2-dioxaborolane (141 mg, 0.43 mmol) and Example 41A (50 mg, 0.29 mmol). The reaction was heated with microwave at 150° C. for 70 min. The reaction was filtered through a pad of celite, which was further rinsed with MeOH. The combined solution was concentrated and purified through normal phase chromatography to provide Example 41B (81 mg, 73%) as white solids. MS(ESI) m/z 378 (M+H)$^+$.

Example 41C

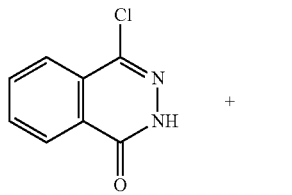

Example 41 was prepared by following a similar procedure to that described in Example 30 by replacing Example 30C with Example 41B. MS(ESI) m/z 396 (M+H)$^+$. $^1$H NMR (500 MHz, DMSO-d$_6$, ppm) δ 12.86 (s, 1H), 8.39 (s, 1H), 8.34 (d, J=7.3 Hz, 1H), 8.08 (d, J=8.2 Hz, 2H), 7.96-7.83 (m, 2H), 7.78-7.62 (m, 3H), 7.46-7.26 (m, 5H), 4.91 (s, 2H). Analytical HPLC: RT=1.59 min (Method D).

Example 42: 4-(4-{3-[(4-fluoro-3-methoxyphenyl)amino]-2-oxopyrrolidin-1-yl}phenyl)-1,2-dihydrophthalazin-1-one

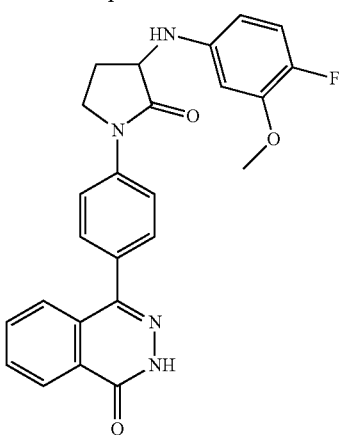

Example 42 was prepared by following a similar procedure to that described in Example 30 by replacing 3-(difluoromethoxy)aniline with 4-fluoro-3-methoxyaniline in Example 30A. MS(ESI) m/z 445 (M+H)+. ¹H NMR (500 MHz, DMSO-d₆, ppm) δ 12.85 (s, 1H), 8.35 (d, J=6.7 Hz, 1H), 7.89 (d, J=8.2 Hz, 4H), 7.71 (d, J=7.0 Hz, 1H), 7.63 (d, J=7.9 Hz, 2H), 6.92 (t, J=9.9 Hz, 1H), 6.54 (d, J=7.3 Hz, 1H), 6.23 (d, J=7.3 Hz, 1H), 4.40 (t, J=9.0 Hz, 1H), 3.96-3.85 (m, 2H), 3.77 (s, 3H), 2.65 (br. s., 1H), 1.93 (quin, J=10.0 Hz, 1H). Analytical HPLC: RT=1.64 min (Method D).

Example 43: 4-(4-{3-[(3-ethoxyphenyl)amino]-2-oxopyrrolidin-1-yl}phenyl)-1,2-dihydrophthalazin-1-one

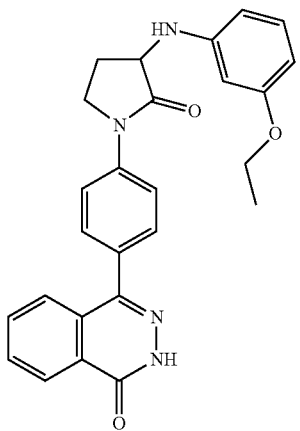 [SMILES: CCOc1cccc(NC2CCN(c3ccc(-c4n[nH]c(=O)c5ccccc45)cc3)C2=O)c1]

Example 43 was prepared by following a similar procedure to that described in Example 30 by replacing 3-(difluoromethoxy)aniline with 3-ethoxyaniline in Example 30A. MS(ESI) m/z 441 (M+H)+. ¹H NMR (500 MHz, DMSO-d₆, ppm) δ 12.85 (br. s., 1H), 8.35 (d, J=6.7 Hz, 1H), 7.90 (d, J=7.9 Hz, 4H), 7.71 (d, J=7.0 Hz, 1H), 7.63 (d, J=7.6 Hz, 2H), 6.98 (t, J=7.8 Hz, 1H), 6.36-6.23 (m, 2H), 6.17 (d, J=7.6 Hz, 1H), 4.41 (d, J=7.0 Hz, 1H), 4.01-3.92 (m, 2H), 3.90 (d, J=7.6 Hz, 2H), 2.63 (br. s., 1H), 1.94 (quin, J=9.8 Hz, 1H), 1.29 (t, J=6.4 Hz, 3H). Analytical HPLC: RT=1.75 min (Method D).

Example 44: 4-[4-(3-{[(1R)-1-(3-methoxyphenyl)ethyl]amino}-2-oxopyrrolidin-1-yl)phenyl]-1,2-dihydrophthalazin-1-one

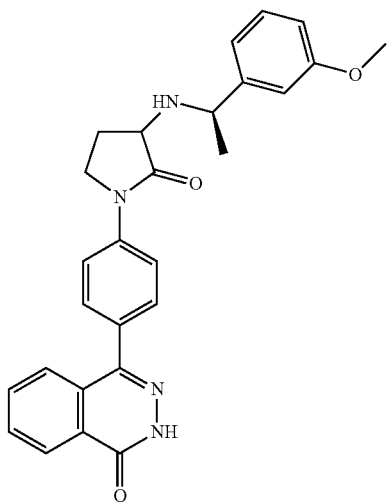 [SMILES: COc1cccc([C@@H](C)NC2CCN(c3ccc(-c4n[nH]c(=O)c5ccccc45)cc3)C2=O)c1]

Example 44 was prepared by following a similar procedure to that described in Example 30 by replacing 3-(difluoromethoxy)aniline with (R)-1-(3-methoxyphenyl)ethanamine in Example 30A. MS(ESI) m/z 455 (M+H)+. ¹H NMR (500 MHz, DMSO-d₆, ppm) δ 12.84 (s, 1H), 8.34 (d, J=6.7 Hz, 1H), 7.91 (br. s., 2H), 7.83 (d, J=8.2 Hz, 2H), 7.70 (d, J=6.7 Hz, 1H), 7.60 (d, J=7.9 Hz, 2H), 7.27 (q, J=8.6 Hz, 1H), 7.07-6.92 (m, 2H), 6.83 (br. s., 1H), 4.26 (br. s., 1H), 3.94-3.82 (m, 1H), 3.76 (s, 3H), 3.60-3.53 (m, 2H), 2.42-2.01 (m, 1H), 1.96-1.64 (m, 1H), 1.35 (dd, J=16.0, 4.7 Hz, 3H). Analytical HPLC: RT=1.68 min (Method D).

Example 45: 4-(4-{2-oxo-3-[(2-phenylethyl)amino]pyrrolidin-1-yl}phenyl)-1,2-dihydrophthalazin-1-one

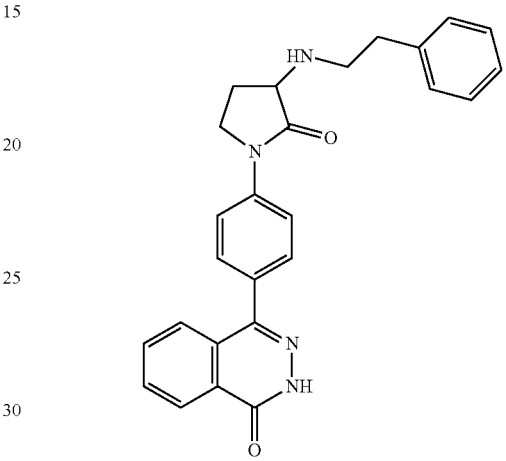

Example 45 was prepared by following a similar procedure to that described in Example 30 by replacing 3-(difluoromethoxy)aniline with phenethylamine in Example 30A. MS(ESI) m/z 425 (M+H)+. ¹H NMR (500 MHz, DMSO-d₆, ppm) δ 12.87 (s, 1H), 8.35 (d, J=6.7 Hz, 1H), 8.00-7.79 (m, 4H), 7.75-7.58 (m, 3H), 7.42-7.17 (m, 5H), 4.18 (t, J=9.2 Hz, 1H), 4.02-3.83 (m, 2H), 3.33-3.21 (m, 1H), 3.21-3.09 (m, 1H), 3.02-2.84 (m, 2H), 2.58 (br. s., 1H), 2.17-1.99 (m, 1H). Analytical HPLC: RT=1.26 min (Method C).

Example 46: 4-(4-{4-[(3-methoxyphenyl)methyl]-5-oxo-4,5-dihydro-1H-1,2,4-triazol-1-yl}phenyl)-1,2-dihydrophthalazin-1-one

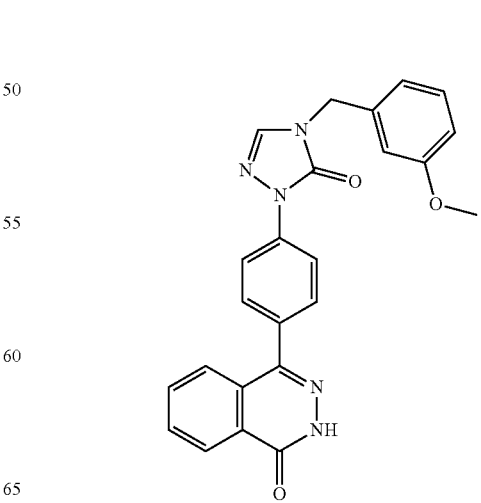

Example 46 was prepared by following a similar procedure to that described in Example 41 by replacing benzyl bromide with 3-methoxybenzyl bromide in Example 41A. MS(ESI) m/z 426 (M+H)+. 1H NMR (500 MHz, DMSO-d6, ppm) δ 12.85 (s, 1H), 8.42 (s, 1H), 8.35 (d, J=7.0 Hz, 1H), 8.10 (d, J=7.9 Hz, 2H), 7.98-7.83 (m, 2H), 7.78-7.60 (m, 3H), 7.32 (t, J=7.9 Hz, 1H), 7.03-6.85 (m, 3H), 4.89 (s, 2H), 3.76 (s, 3H). Analytical HPLC: RT=1.61 min (Method D).

Example 47: 4-benzyl-1-(4-{4-oxo-3H,4H-pyrrolo[1,2-d][1,2,4]triazin-1-yl}phenyl)-4,5-dihydro-1H-1,2,4-triazol-5-one

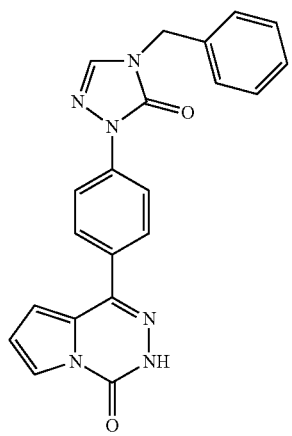 [SMILES: O=c1n(Cc2ccccc2)cnn1-c1ccc(-c2n[nH]c(=O)n3cccc23)cc1]

Example 47A: 1H-pyrrole-2-carbohydrazide

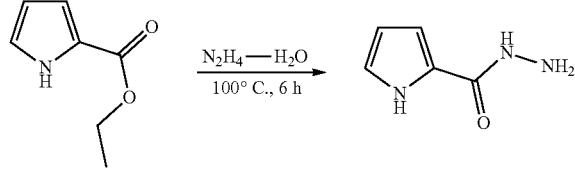

Methyl 1H-pyrrole-2-carboxylate (1.00 g, 8.0 mmol) was placed in a pressure vial, and hydrazine hydrate (7.8 ml, 160 mmol) was added. After ~1 h at rt, the reaction mixture became heterogeneous, and white precipitate was formed. The reaction mixture was stirred at 100° C. for 6 h. The reaction was allowed to cool to rt. The reaction mixture was diluted with H2O (20 mL), filtered, and the filter cake was washed with water (2×5 mL). The obtained residue was dried in a vacuum oven for 24 h to afford Example 47A (0.87 g, 87%) as a white solid. MS(ESI) m/z 148 (M+Na)+. 1H NMR (400 MHz, DMSO-d6, ppm) δ 11.41 (br. s., 1H), 9.21 (br. s., 1H), 6.83 (td, J=2.7, 1.4 Hz, 1H), 6.76-6.66 (m, 1H), 6.05 (dt, J=3.7, 2.4 Hz, 1H), 4.28 (s, 2H).

Example 47B: 2,3-dihydropyrrolo[1,2-d][1,2,4]triazine-1,4-dione

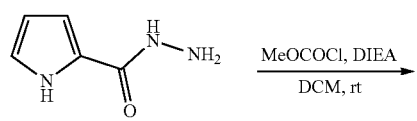

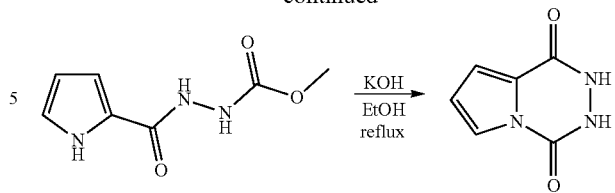

To a suspension of Example 47A (0.55 g, 4.4 mmol) in DCM (29 ml) was added DIEA (2.30 ml, 13.2 mmol) followed by addition of methyl chloroformate (0.51 ml, 6.6 mmol) at rt, then the reaction mixture was stirred at rt for 14 h. The solvent was removed under reduced pressure. The residue was dissolved in anhydrous EtOH (80 mL), and KOH (0.86 g, 15.4 mmol) was added. The reaction was stirred at reflux for 2 h., and it was cooled to rt. The precipitate formed was filtered off, and it was taken up in H2O (20 mL). The obtained solution was acidified with 1.0 N HCl (aq.) to pH ~4, and stirred at rt for 30 min. The obtained precipitated was collected and dried under reduced pressure in a vacuum oven (~50° C., 4 h) to afford Example 47B (0.50 g, 76%) as a white solid. MS(ESI) m/z 152 (M+H)+. 1H NMR (400 MHz, DMSO-d6, ppm) δ 11.43 (br s, 2H), 7.66 (dd, J=2.9, 1.5 Hz, 1H), 6.80 (dd, J=3.5, 1.3 Hz, 1H), 6.71 (t, J=3.3 Hz, 1H).

Example 47C: 1-chloropyrrolo[1,2-d][1,2,4]triazin-4(3H)-one

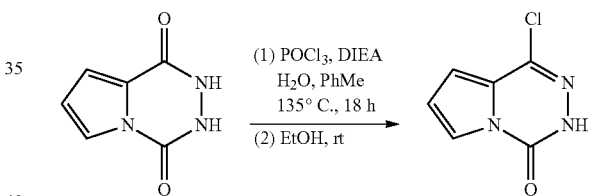

To Example 47B (0.900 g, 5.96 mmol) in a pressure flask with DIEA (2.1 ml, 11.9 mmol) and H2O (0.14 ml, 7.74 mmol) in toluene (20.0 ml) was added POCl3 (2.78 ml, 29.8 mmol) dropwise within 5 min. The flask was capped, and the reaction was stirred at 135° C. for 18 h. The reaction mixture was added dropwise into EtOH (50 mL) at rt within 10 min, and then it was stirred at rt for 15 min. Most of EtOH was removed under reduced pressure. Purification by normal phase chromatography afforded Example 47C (0.554 g, 3.27 mmol, 55%) as a white solid. MS(ESI) m/z 170 (M+H)+. 1H NMR (400 MHz, DMSO-d6, ppm) δ 12.52 (br s, 1H), 7.86 (dd, J=2.8, 1.4 Hz, 1H), 6.91 (dd, J=3.9, 1.9 Hz, 1H), 6.90-6.86 (m, 1H).

Example 47D

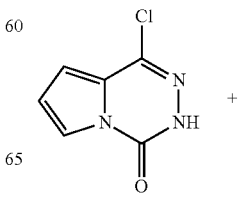 +

-continued

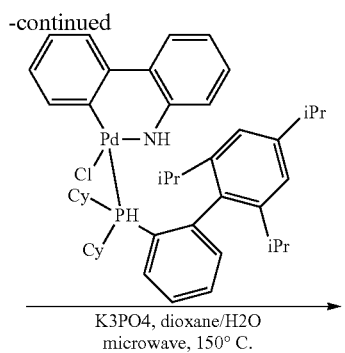

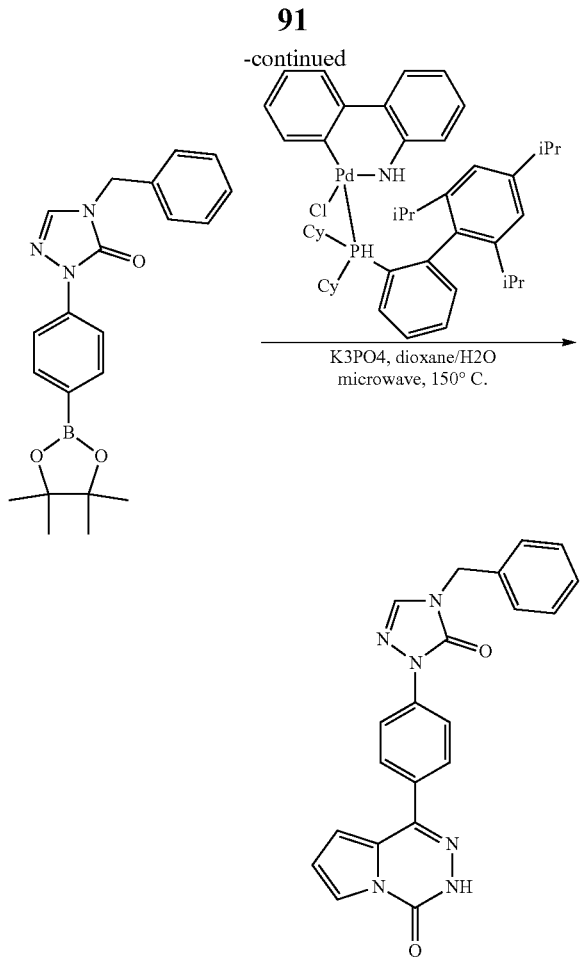

Example 47 was prepared by following a similar procedure to that described in Example 41 by replacing 4-chlorophthalazin-1(2H)-one with Example 47C. MS(ESI) m/z 385 (M+H)+. 1H NMR (500 MHz, DMSO-d6, ppm) δ 12.52 (s, 1H), 8.42 (s, 1H), 8.09 (d, J=7.9 Hz, 2H), 7.96-7.80 (m, 3H), 7.43-7.30 (m, 5H), 6.98 (br. s., 1H), 6.90 (br. s., 1H), 4.92 (s, 2H). Analytical HPLC: RT=1.63 min (Method D).

Example 48: 4-[4-(3-{[3-methoxy-4-(4-methylpiperazin-1-yl)phenyl]amino}-2-oxopyrrolidin-1-yl)phenyl]-1,2-dihydrophthalazin-1-one

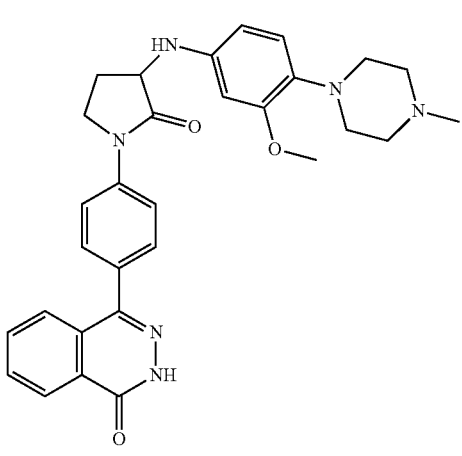 [SMILES: COc1cc(NC2CCN(c3ccc(-c4n[nH]c(=O)c5ccccc45)cc3)C2=O)ccc1N1CCN(C)CC1]

Example 48 was prepared by following a similar procedure to that described in Example 30 by replacing 3-(difluoromethoxy)aniline with 3-methoxy-4-(4-methylpiperazin-1-yl)aniline in Example 30A. MS(ESI) m/z 525 (M+H)+. 1H NMR (500 MHz, DMSO-d6, ppm) δ 12.85 (s, 1H), 8.36 (d, J=6.7 Hz, 1H), 7.91 (d, J=6.7 Hz, 4H), 7.72 (d, J=6.4 Hz, 1H), 7.65 (d, J=7.9 Hz, 2H), 6.76 (d, J=7.9 Hz, 1H), 6.46 (br. s., 1H), 6.26 (d, J=8.5 Hz, 1H), 4.40 (t, J=8.5 Hz, 1H), 3.99-3.86 (m, 2H), 3.80-3.10 (m, 8H), 2.85 (br. s., 4H), 2.64 (br. s., 1H), 2.01-1.85 (m, 1H). Analytical HPLC: RT=1.13 min (Method C).

Example 49: 4-[4-(3-{[3-methoxy-4-(morpholin-4-yl)phenyl]amino}-2-oxopyrrolidin-1-yl)phenyl]-1,2-dihydrophthalazin-1-one

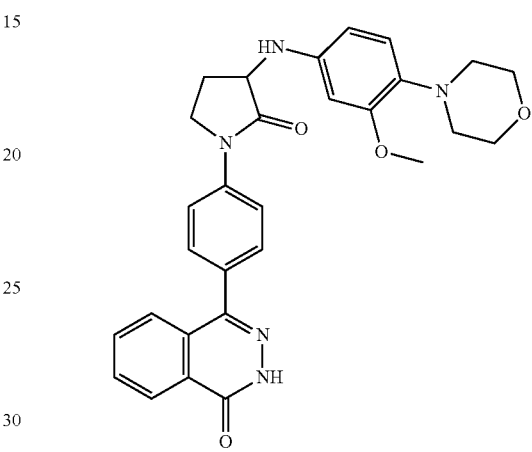

Example 49 was prepared by following a similar procedure to that described in Example 30 by replacing 3-(difluoromethoxy)aniline with 3-methoxy-4-morpholinoaniline in Example 30A. MS(ESI) m/z 512 (M+H)+. 1H NMR (500 MHz, DMSO-d6, ppm) δ 12.84 (s, 1H), 8.36 (d, J=7.0 Hz, 1H), 7.92 (d, J=7.0 Hz, 4H), 7.72 (d, J=7.0 Hz, 1H), 7.65 (d, J=7.9 Hz, 2H), 6.85 (br. s., 1H), 6.48 (br. s., 1H), 6.29 (d, J=7.6 Hz, 1H), 4.42 (br. s., 1H), 4.00-3.85 (m, 2H), 3.78 (br. s., 3H), 3.76-3.64 (m, 2H), 3.59-2.78 (m, 6H), 2.65 (br. s., 1H), 1.95 (quin, J=9.7 Hz, 1H). Analytical HPLC: RT=1.18 min (Method C).

Example 50: 4-(4-{3-[(2,3-dihydro-1,4-benzodioxin-6-yl)amino]-2-oxopyrrolidin-1-yl}phenyl)-1,2-dihydrophthalazin-1-one

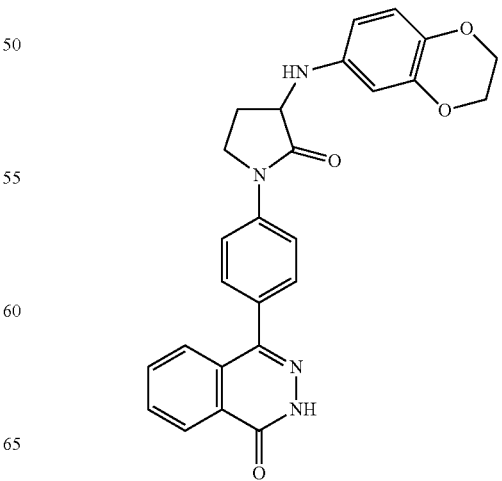

Example 50 was prepared by following a similar procedure to that described in Example 30 by replacing 3-(difluoromethoxy)aniline with 2,3-dihydrobenzo[b][1,4]dioxin-6-amine in Example 30A. MS(ESI) m/z 455 (M+H)+. 1H NMR (500 MHz, DMSO-d6, ppm) δ 12.84 (s, 1H), 8.35 (d, J=7.3 Hz, 1H), 7.91 (d, J=6.7 Hz, 4H), 7.73 (d, J=7.0 Hz, 1H), 7.64 (d, J=7.9 Hz, 2H), 6.62 (d, J=7.9 Hz, 1H), 6.27 (br. s., 1H), 5.55 (d, J=6.4 Hz, 1H), 4.35-4.25 (m, 1H), 4.18 (br. s., 2H), 4.13 (br. s., 2H), 3.97-3.83 (m, 2H), 2.64 (br. s., 1H), 1.97-1.84 (m, 1H). Analytical HPLC: RT=1.40 min (Method C).

Example 51: 4-(4-{3-[(2,2-difluoro-2H-1,3-benzodioxol-5-yl)amino]-2-oxopyrrolidin-1-yl}phenyl)-1,2-dihydrophthalazin-1-one 1

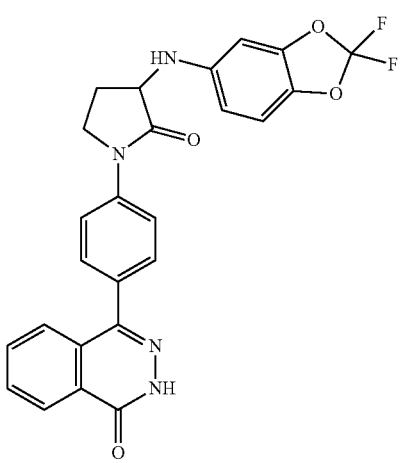 [SMILES: O=C1C(Nc2ccc3c(c2)OC(F)(F)O3)CCN1c1ccc(-c2n[nH]c(=O)c3ccccc23)cc1]

Example 51 was prepared by following a similar procedure to that described in Example 30 by replacing 3-(difluoromethoxy)aniline with 2,2-difluorobenzo[d][1,3]dioxol-5-amine in Example 30A. MS(ESI) m/z 477 (M+H)+. 1H NMR (500 MHz, DMSO-d6, ppm) δ 12.83 (s, 1H), 8.34 (d, J=7.3 Hz, 1H), 7.90 (d, J=7.3 Hz, 4H), 7.71 (d, J=7.0 Hz, 1H), 7.64 (d, J=7.9 Hz, 2H), 7.11 (d, J=8.5 Hz, 1H), 6.80 (s, 1H), 6.49 (d, J=8.9 Hz, 1H), 6.23 (d, J=6.7 Hz, 1H), 4.43 (q, J=8.2 Hz, 1H), 3.96-3.84 (m, 2H), 2.72-2.62 (m, 1H), 1.93 (quin, J=10.0 Hz, 1H). Analytical HPLC: RT=1.90 min (Method C).

Example 52: 4-[4-(2-oxo-3-{[3-(trifluoromethoxy)phenyl]amino}pyrrolidin-1-yl)phenyl]-1,2-dihydrophthalazin-1-one

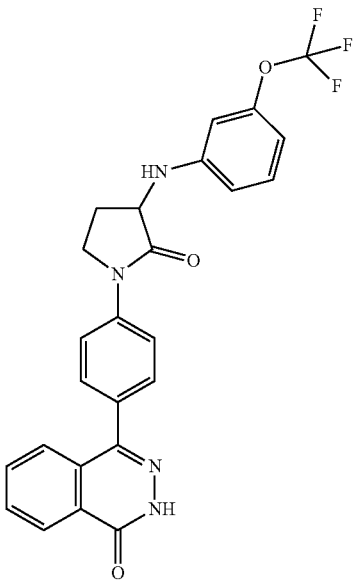 [SMILES: O=C1C(Nc2cccc(OC(F)(F)F)c2)CCN1c1ccc(-c2n[nH]c(=O)c3ccccc23)cc1]

Example 52 was prepared by following a similar procedure to that described in Example 30 by replacing 3-(difluoromethoxy)aniline with 3-(trifluoromethoxy)aniline in Example 30A. MS(ESI) m/z 481 (M+H)+. 1H NMR (500 MHz, DMSO-d6, ppm) δ 12.83 (s, 1H), 8.35 (d, J=7.0 Hz, 1H), 7.90 (d, J=7.0 Hz, 4H), 7.72 (d, J=7.0 Hz, 1H), 7.64 (d, J=7.9 Hz, 2H), 7.19 (t, J=7.9 Hz, 1H), 6.74 (d, J=8.2 Hz, 1H), 6.68 (br. s., 1H), 6.49 (dd, J=13.4, 7.6 Hz, 2H), 4.51 (q, J=8.3 Hz, 1H), 4.01-3.83 (m, 2H), 2.70-2.60 (m, 1H), 1.96 (quin, J=10.0 Hz, 1H). Analytical HPLC: RT=1.95 min (Method D).

Example 53: 4-(4-{4-[(3-fluorophenyl)methyl]-5-oxo-4,5-dihydro-1H-1,2,4-triazol-1-yl}phenyl)-1,2-dihydrophthalazin-1-one

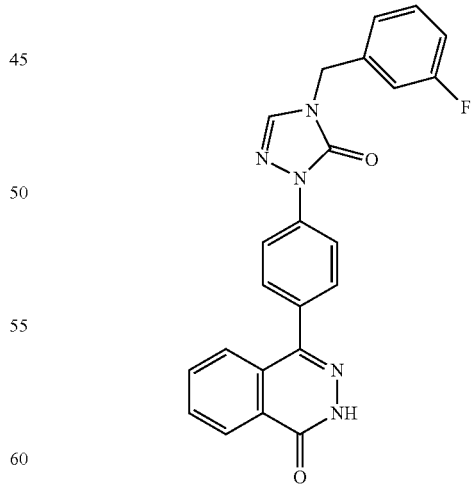

Example 53 was prepared by following a similar procedure to that described in Example 41 by replacing benzyl bromide with 3-fluorobenzyl bromide in Example 41A. MS(ESI) m/z 414 (M+H)+. 1H NMR (500 MHz, DMSO-d6, ppm) δ 12.85 (s, 1H), 8.44 (s, 1H), 8.35 (d, J=6.4 Hz, 1H), 8.10 (d, J=7.9 Hz, 2H), 7.91 (br. s., 2H), 7.78-7.61 (m, 3H), 7.52-7.39 (m, 1H), 7.34-7.11 (m, 3H), 4.95 (br. s., 2H). Analytical HPLC: RT=1.63 min (Method C).

Example 54: 4-{4-[5-oxo-4-(1-phenylethyl)-4,5-dihydro-1H-1,2,4-triazol-1-yl]phenyl}-1,2-dihydrophthalazin-1-one

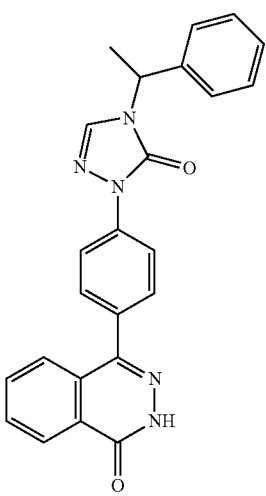 [SMILES: CC(c1ccccc1)n1cnn(-c2ccc(-c3n[nH]c(=O)c4ccccc34)cc2)c1=O]

Example 54 was prepared by following a similar procedure to that described in Example 41 by replacing benzyl bromide with (1-bromoethyl)benzene in Example 41A. MS(ESI) m/z 410 (M+H)+. $^1$H NMR (500 MHz, DMSO-$d_6$, ppm) δ 12.85 (s., 1H), 8.60 (br. s., 1H), 8.34 (d, J=6.4 Hz, 1H), 8.08 (d, J=7.6 Hz, 2H), 7.90 (br. s., 2H), 7.79-7.64 (m, 3H), 7.45-7.27 (m, 5H), 5.32 (d, J=6.7 Hz, 1H), 1.80 (d, J=6.4 Hz, 3H). Analytical HPLC: RT=1.68 min (Method D).

Example 55: 4-[4-(3-{[3-(difluoromethoxy)phenyl]amino}-2-oxopyrrolidin-1-yl)phenyl]-1,2-dihydrophthalazin-1-one (enantiomer 1), and Example 56: 4-[4-(3-{[3-(difluoromethoxy)phenyl]amino}-2-oxopyrrolidin-1-yl)phenyl]-1,2-dihydrophthalazin-1-one (enantiomer 2)

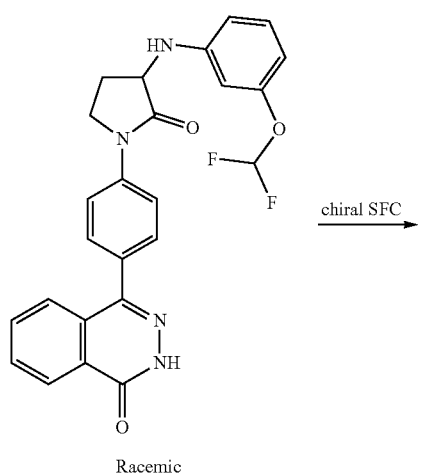

Racemic chiral SFC ⟶

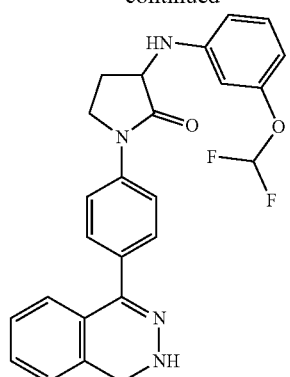

Enantiomer 1
Example 55

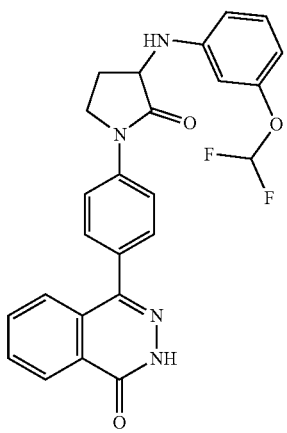

Enantiomer 2
Example 56

Example 30 (racemic) was subjected to SFC chiral separation (column: (R,R) Whelk-O1, 21×250 mm, 5 micron; mobile phase: 50% MeOH/50% CO$_2$; flow conditions: 45 mL/min; pressure: 150 Bar; temperature: 40° C.; detector wavelength: 220 nm). Two enantiomers were obtained as white solids.

Example 55, peak 1, enantiomer 1, ee>99%. MS(ESI) m/z 463 (M+H)+. $^1$H NMR (400 MHz, CDCl$_3$) δ 10.34 (br. s., 1H), 8.63-8.47 (m, 1H), 7.87 (d, J=8.6 Hz, 2H), 7.84-7.74 (m, 3H), 7.65 (d, J=8.6 Hz, 2H), 7.19 (t, J=8.0 Hz, 1H), 6.59 (dd, J=8.1, 1.5 Hz, 1H), 6.53 (d, J=8.1 Hz, 1H), 6.47 (s, 1H), 6.51 (t, J=74.4 Hz, 1H), 4.74 (br. s., 1H), 4.20 (t, J=8.0 Hz, 1H), 4.07-3.85 (m, 2H), 2.93 (dt, J=12.3, 6.2 Hz, 1H), 2.19-2.03 (m, 1H). Analytical HPLC: RT=12.10 min (Method A).

Example 56, peak 2, enantiomer 2, ee 98.4%. MS(ESI) m/z 463 (M+H)+. $^1$H NMR (400 MHz, CDCl$_3$) δ 10.21 (br. s., 1H), 8.61-8.48 (m, 1H), 7.87 (d, J=8.6 Hz, 2H), 7.84-7.76 (m, 3H), 7.65 (d, J=8.6 Hz, 2H), 7.20 (t, J=8.1 Hz, 1H), 6.59 (dd, J=8.1, 2.0 Hz, 1H), 6.56-6.52 (m, 1H), 6.50-6.45 (m, 1H), 6.51 (t, J=74.6 Hz, 1H), 4.74 (d, J=2.6 Hz, 1H), 4.20 (ddd, J=10.6, 7.8, 3.0 Hz, 1H), 4.05-3.89 (m, 2H), 3.01-2.87 (m, 1H), 2.18-2.01 (m, 1H). Analytical HPLC: RT=12.04 min (Method A).

Example 57: 4-[4-(2-oxo-3-{[3-(propan-2-yloxy) phenyl]amino}pyrrolidin-1-yl)phenyl]-1,2-dihydrophthalazin-1-one

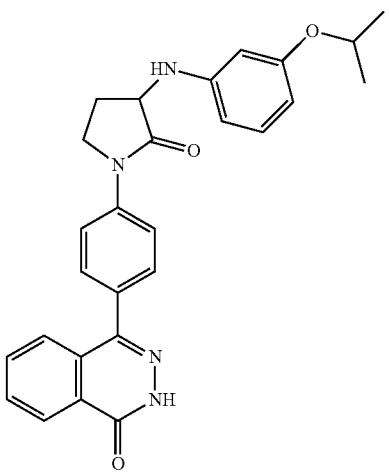 [SMILES: CC(C)Oc1cccc(NC2CCN(c3ccc(-c4n[nH]c(=O)c5ccccc45)cc3)C2=O)c1]

Example 57 was prepared by following a similar procedure to that described in Example 30 by replacing 3-(difluoromethoxy)aniline with 3-isopropoxyaniline in Example 30A. MS(ESI) m/z 455 (M+H)$^+$. $^1$H NMR (500 MHz, DMSO-d$_6$, ppm) δ 12.84 (br. s., 1H), 8.36 (d, J=6.1 Hz, 1H), 7.92 (d, J=5.5 Hz, 4H), 7.73 (d, J=6.4 Hz, 1H), 7.65 (d, J=7.6 Hz, 2H), 6.98 (t, J=6.9 Hz, 1H), 6.30 (br. s., 2H), 6.17 (d, J=7.6 Hz, 1H), 5.92 (d, J=5.2 Hz, 1H), 4.52 (br. s., 1H), 4.42 (d, J=7.9 Hz, 1H), 3.92 (d, J=8.5 Hz, 2H), 2.64 (br. s., 1H), 1.95 (t, J=9.9 Hz, 1H), 1.25 (br. s., 6H). Analytical HPLC: RT=1.84 min (Method D).

Example 58: 4-[4-(3-{[3-(difluoromethoxy)phenyl] amino}-2-oxopyrrolidin-1-yl)phenyl]-1,2-dihydroisoquinolin-1-one

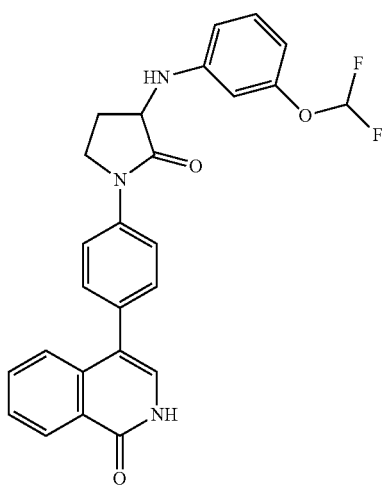 [SMILES: O=C1C(Nc2cccc(OC(F)F)c2)CCN1c1ccc(-c2c[nH]c(=O)c3ccccc23)cc1]

Example 58 was prepared by following a similar procedure to that described in Example 30 by replacing 4-chlorophthalazin-1(2H)-one with 4-bromoisoquinolin-1(2H)-one in Example 30C. MS(ESI) m/z 462 (M+H)$^+$. $^1$H NMR (500 MHz, DMSO-d$_6$, ppm) δ 11.45 (br. s., 1H), 8.30 (d, J=7.3 Hz, 1H), 7.83 (d, J=7.6 Hz, 2H), 7.75-7.64 (m, 1H), 7.59-7.50 (m, 2H), 7.47 (d, J=7.3 Hz, 2H), 7.33-6.93 (m, 3H), 6.60 (d, J=7.6 Hz, 1H), 6.52 (br. s., 1H), 6.36 (d, J=7.6 Hz, 1H), 6.31 (d, J=5.5 Hz, 1H), 4.45 (d, J=7.9 Hz, 1H), 3.89 (d, J=7.9 Hz, 2H), 2.63 (br. s., 1H), 1.94 (t, J=9.9 Hz, 1H). Analytical HPLC: RT=1.83 min (Method C).

Example 59: 2-({2-oxo-1-[4-(4-oxo-3,4-dihydrophthalazin-1-yl)phenyl]pyrrolidin-3-yl}amino)-1,3-thiazole-5-carbonitrile

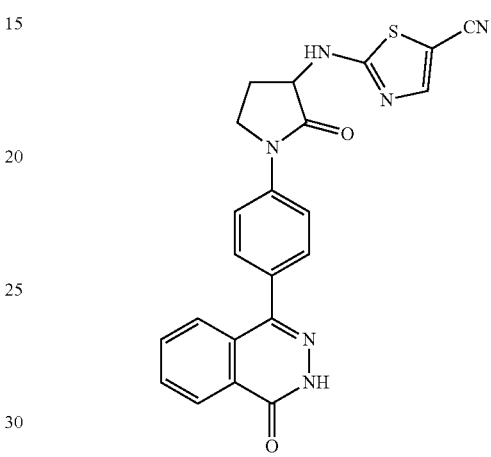

Example 59 was prepared by following a similar procedure to that described in Example 30 by replacing 3-(difluoromethoxy)aniline with 2-aminothiazole-5-carbonitrile in Example 30A. MS(ESI) m/z 429 (M+H)$^+$. $^1$H NMR (500 MHz, DMSO-d$_6$, ppm) δ 12.84 (br. s., 1H), 8.35 (br. s., 1H), 7.99-7.85 (m, 5H), 7.73 (br. s., 1H), 7.65 (d, J=7.3 Hz, 2H), 4.82 (br. s., 1H), 3.94 (d, J=8.5 Hz, 2H), 2.64 (br. s., 1H), 2.15 (t, J=10.2 Hz, 1H). Analytical HPLC: RT=1.34 min (Method D).

Example 60: 4-[4-(3-{[4-(difluoromethoxy)phenyl] amino}-2-oxopyrrolidin-1-yl)phenyl]-1,2-dihydrophthalazin-1-one Trifluoroacetic Acid Salt

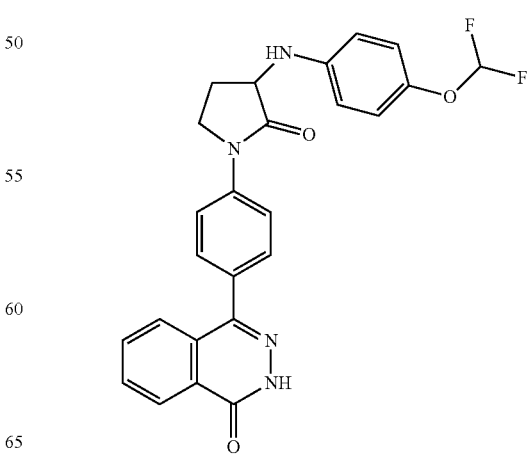

Example 60 was prepared by following a similar procedure to that described in Example 30 by replacing 3-(difluoromethoxy)aniline with 4-(difluoromethoxy)aniline in Example 30A. MS(ESI) m/z 463 (M+H)+. 1H NMR (500 MHz, DMSO-d6, ppm) δ 12.85 (s, 1H), 8.41-8.30 (m, 1H), 7.96-7.85 (m, 4H), 7.75-7.69 (m, 1H), 7.63 (d, J=8.5 Hz, 2H), 7.11-6.78 (m, 3H), 6.75 (d, J=8.9 Hz, 2H), 4.41 (t, J=9.0 Hz, 1H), 4.00-3.81 (m, 2H), 2.70-2.60 (m, 1H), 2.01-1.86 (m, 1H). Analytical HPLC: RT=1.73 min (Method D).

Example 61: 4-(4-{3-[(2-methoxyphenyl)amino]-2-oxopyrrolidin-1-yl}phenyl)-1,2-dihydrophthalazin-1-one Trifluoroacetic Acid Salt

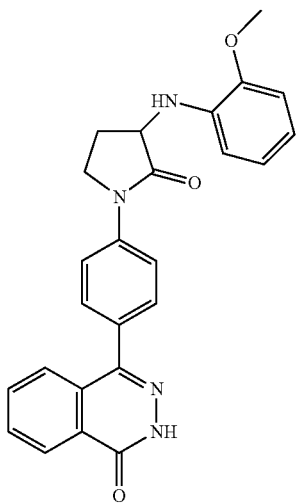 [SMILES: COc1ccccc1NC1CCN(c2ccc(-c3n[nH]c(=O)c4ccccc34)cc2)C1=O]

Example 61 was prepared by following a similar procedure to that described in Example 30 by replacing 3-(difluoromethoxy)aniline with 2-methoxyaniline in Example 30A. MS(ESI) m/z 427 (M+H)+. 1H NMR (500 MHz, DMSO-d6, ppm) δ 12.85 (s, 1H), 8.42-8.30 (m, 1H), 7.97-7.85 (m, 4H), 7.77-7.70 (m, 1H), 7.64 (d, J=8.5 Hz, 2H), 6.87 (d, J=7.9 Hz, 1H), 6.84-6.78 (m, 1H), 6.73 (d, J=7.0 Hz, 1H), 6.68-6.61 (m, 1H), 5.15 (d, J=5.5 Hz, 1H), 4.36 (ddd, J=10.4, 8.1, 5.6 Hz, 1H), 3.93 (dd, J=9.6, 3.8 Hz, 2H), 3.82 (s, 3H), 2.75 (ddt, J=11.8, 7.9, 3.9 Hz, 1H), 2.05-1.94 (m, 1H). Analytical HPLC: RT=1.65 min (Method C).

Example 62: 7-({2-oxo-1-[4-(4-oxo-3,4-dihydrophthalazin-1-yl)phenyl]pyrrolidin-3-yl}amino)-3,4-dihydro-2H-1,4-benzoxazin-3-one

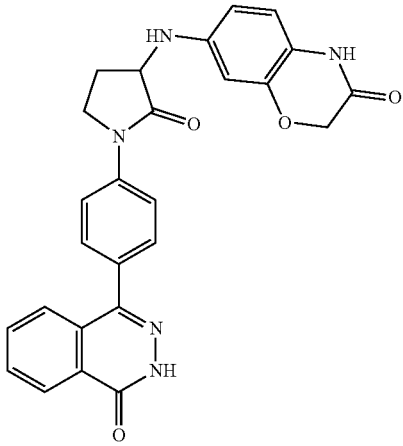 [SMILES: O=C1COc2cc(NC3CCN(c4ccc(-c5n[nH]c(=O)c6ccccc56)cc4)C3=O)ccc2N1]

Example 62 was prepared by following a similar procedure to that described in Example 30 by replacing 3-(difluoromethoxy)aniline with 7-amino-2H-benzo[b][1,4]oxazin-3(4H)-one in Example 30A. MS(ESI) m/z 468 (M+H)+. 1H NMR (500 MHz, DMSO-d6, ppm) δ 12.85 (d, J=7.9 Hz, 1H), 10.34 (d, J=7.6 Hz, 1H), 8.36 (d, J=6.4 Hz, 1H), 7.92 (br. s., 4H), 7.79-7.69 (m, 1H), 7.69-7.57 (m, 2H), 6.76-6.62 (m, 1H), 6.46-6.30 (m, 2H), 5.84 (d, J=6.4 Hz, 1H), 4.51-4.42 (m, 2H), 4.39-4.28 (m, 1H), 3.90 (dd, J=14.5, 7.8 Hz, 2H), 2.63 (br. s., 1H), 1.93 (d, J=8.9 Hz, 1H). Analytical HPLC: RT=1.29 min (Method D).

Example 63: 4-[4-(4-{[3-(difluoromethoxy)phenyl]methyl}-5-oxo-4,5-dihydro-1H-1,2,4-triazol-1-yl)phenyl]-1,2-dihydrophthalazin-1-one

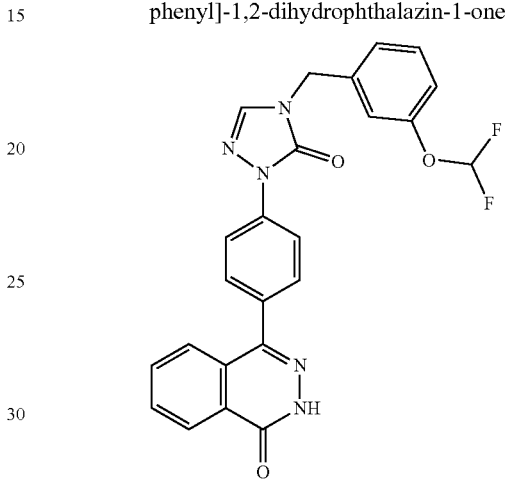

Example 63 was prepared by following a similar procedure to that described in Example 41 by replacing benzyl bromide with 1-(bromomethyl)-3-(difluoromethoxy)benzene in Example 41A. MS(ESI) m/z 462 (M+H)+. 1H NMR (500 MHz, DMSO-d6, ppm) δ 12.86 (s, 1H), 8.43 (s, 1H), 8.34 (dd, J=6.6, 2.6 Hz, 1H), 8.09 (d, J=8.5 Hz, 2H), 7.98-7.86 (m, 2H), 7.77-7.63 (m, 3H), 7.46 (t, J=7.9 Hz, 1H), 7.29-7.21 (m, 2H), 7.16 (dd, J=8.2, 1.8 Hz, 1H), 4.95 (s, 2H). Analytical HPLC: RT=1.7 min (Method D).

Example 64: 4-[4-(2-oxo-3-{[1-(propan-2-yl)-1H-pyrazol-3-yl]amino}pyrrolidin-1-yl)phenyl]-1,2-dihydrophthalazin-1-one

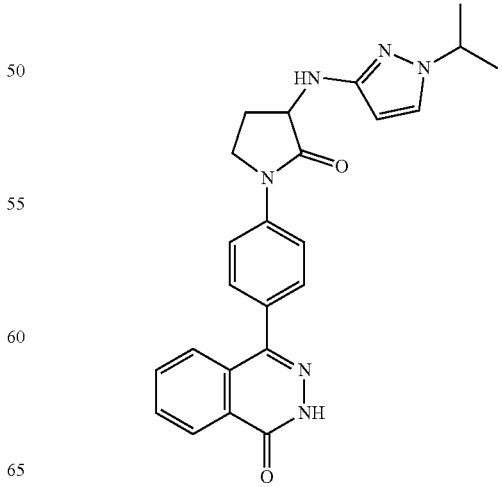

Example 64 was prepared by following a similar procedure to that described in Example 30 by replacing 3-(difluoromethoxy)aniline with 1-isopropyl-1H-pyrazol-3-amine in Example 30A. MS(ESI) m/z 429 (M+H)$^+$. $^1$H NMR (500 MHz, DMSO-d$_6$, ppm) δ 12.76 (s, 1H), 8.34-8.20 (m, 1H), 7.90-7.78 (m, 4H), 7.65 (d, J=7.0 Hz, 1H), 7.56 (d, J=8.5 Hz, 2H), 7.32 (d, J=2.1 Hz, 1H), 5.51-5.39 (m, 2H), 4.28-4.10 (m, 2H), 3.90-3.74 (m, 2H), 2.55-2.50 (m, 1H), 2.00-1.88 (m, 1H), 1.26 (d, J=6.4 Hz, 6H). Analytical HPLC: RT=1.45 min (Method D).

Example 65: 4-(4-{3-[(1-methyl-1H-pyrazol-3-yl)amino]-2-oxopyrrolidin-1-yl}phenyl)-1,2-dihydrophthalazin-1-one

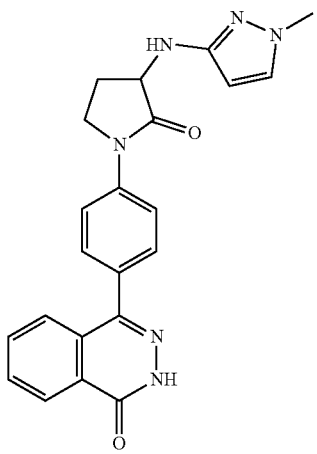 [SMILES: Cn1ccc(NC2CCN(c3ccc(-c4n[nH]c(=O)c5ccccc45)cc3)C2=O)n1]

Example 65 was prepared by following a similar procedure to that described in Example 30 by replacing 3-(difluoromethoxy)aniline with 1-methyl-1H-pyrazol-3-amine in Example 30A. MS(ESI) m/z 401 (M+H)$^+$. $^1$H NMR (500 MHz, DMSO-d$_6$, ppm) δ 12.82 (s, 1H), 8.41-8.27 (m, 1H), 7.98-7.84 (m, 4H), 7.77-7.69 (m, 1H), 7.63 (d, J=8.5 Hz, 2H), 7.33 (d, J=1.8 Hz, 1H), 5.57-5.44 (m, 2H), 4.38-4.25 (m, 1H), 3.96-3.79 (m, 2H), 3.61 (s, 3H), 2.66-2.57 (m, 1H), 2.06-1.91 (m, 1H). Analytical HPLC: RT=1.11 min (Method C).

Example 66: 4-(4-{3-[(2-methyl-1,3-benzothiazol-6-yl)amino]-2-oxopyrrolidin-1-yl}phenyl)-1,2-dihydrophthalazin-1-one

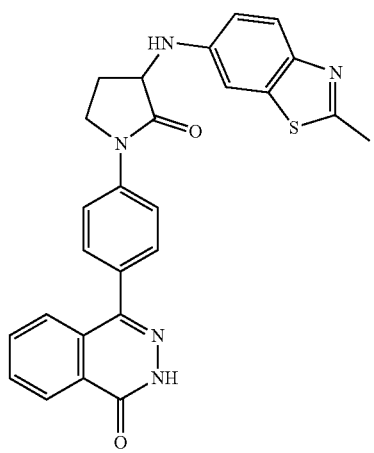 [SMILES: Cc1nc2ccc(NC3CCN(c4ccc(-c5n[nH]c(=O)c6ccccc56)cc4)C3=O)cc2s1]

Example 66 was prepared by following a similar procedure to that described in Example 30 by replacing 3-(difluoromethoxy)aniline with 2-methylbenzo[d]thiazol-6-amine in Example 30A. MS(ESI) m/z 468.1 (M+H)$^+$. $^1$H NMR (500 MHz, DMSO-d$_6$, ppm) δ 12.85 (s, 1H), 8.40-8.28 (m, 1H), 8.01-7.85 (m, 4H), 7.75-7.70 (m, 1H), 7.63 (dd, J=12.1, 8.7 Hz, 3H), 7.24 (d, J=2.1 Hz, 1H), 6.93 (dd, J=8.9, 2.1 Hz, 1H), 6.23 (d, J=7.0 Hz, 1H), 4.56-4.45 (m, 1H), 4.01-3.85 (m, 2H), 2.70-2.67 (m, 3H), 2.78-2.65 (m, 1H), 2.03-1.90 (m, 1H). Analytical HPLC: RT=140 min (Method C).

Example 67: 4-(4-{3-[(3-methanesulfonylphenyl)amino]-2-oxopyrrolidin-1-yl}phenyl)-1,2-dihydrophthalazin-1-one Trifluoroacetic Acid Salt

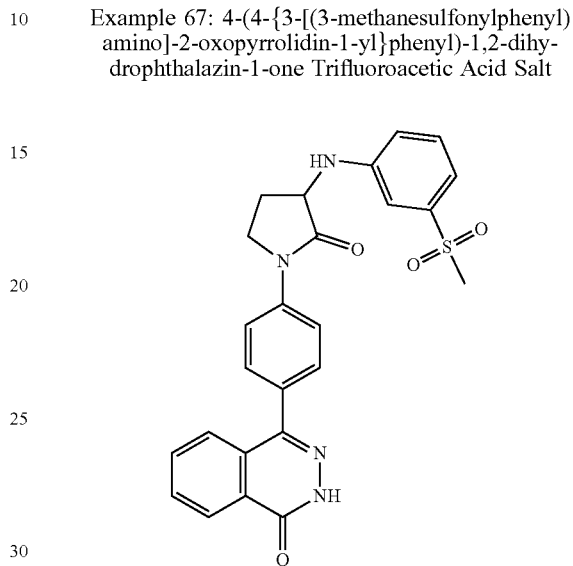

Example 67 was prepared by following a similar procedure to that described in Example 30 by replacing 3-(difluoromethoxy)aniline with 3-(methylsulfonyl)aniline in Example 30A. MS(ESI) m/z 475 (M+H)$^+$. $^1$H NMR (500 MHz, DMSO-d$_6$, ppm) δ 12.83 (s, 1H), 8.40-8.26 (m, 1H), 7.97-7.84 (m, 4H), 7.75-7.69 (m, 1H), 7.64 (d, J=8.5 Hz, 2H), 7.36 (t, J=7.9 Hz, 1H), 7.24 (s, 1H), 7.14-7.00 (m, 2H), 6.65 (d, J=7.3 Hz, 1H), 4.67-4.52 (m, 1H), 4.01-3.84 (m, 2H), 3.14 (s, 3H), 2.65 (dt, J=12.1, 6.2 Hz, 1H), 2.06-1.90 (m, 1H). Analytical HPLC: RT=1.38 min (Method D).

Example 68: 4-[4-(3-{[3-(methylsulfanyl)phenyl]amino}-2-oxopyrrolidin-1-yl)phenyl]-1,2-dihydrophthalazin-1-one

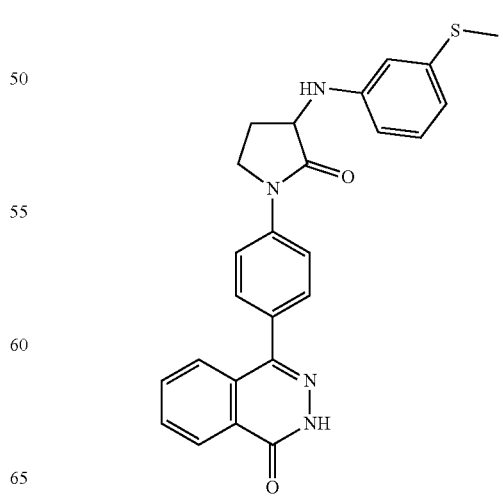

Example 68 was prepared by following a similar procedure to that described in Example 30 by replacing 3-(difluoromethoxy)aniline with 3-(methylthio)aniline in Example 30A. MS(ESI) m/z 443 (M+H)⁺. ¹H NMR (500 MHz, DMSO-d₆, ppm) δ 12.83 (br. s., 1H), 8.43-8.29 (m, 1H), 7.91 (d, J=8.2 Hz, 4H), 7.76-7.69 (m, 1H), 7.64 (d, J=8.5 Hz, 2H), 7.04 (t, J=7.8 Hz, 1H), 6.64 (s, 1H), 6.52 (d, J=7.9 Hz, 1H), 6.48 (d, J=7.6 Hz, 1H), 6.05 (d, J=7.3 Hz, 1H), 4.56-4.40 (m, 1H), 3.99-3.82 (m, 2H), 2.69-2.58 (m, 1H), 2.42 (s, 3H), 2.02-1.88 (m, 1H). Analytical HPLC: RT=1.8 min (Method D).

Example 69: 4-(4-{3-[(6-fluoropyridin-2-yl)amino]-2-oxopyrrolidin-1-yl}phenyl)-1,2-dihydrophthalazin-1-one

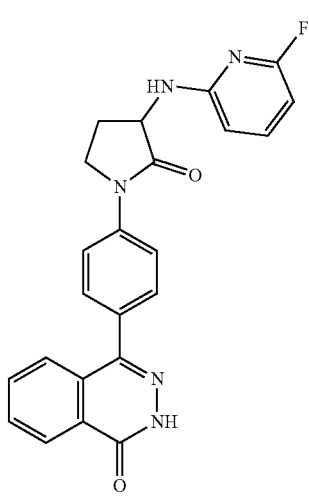 [SMILES: O=C1C(Nc2cccc(F)n2)CCN1c1ccc(-c2n[nH]c(=O)c3ccccc23)cc1]

Example 69A: 1-(4-bromophenyl)-3-((6-fluoropyridin-2-yl)amino)pyrrolidin-2-one

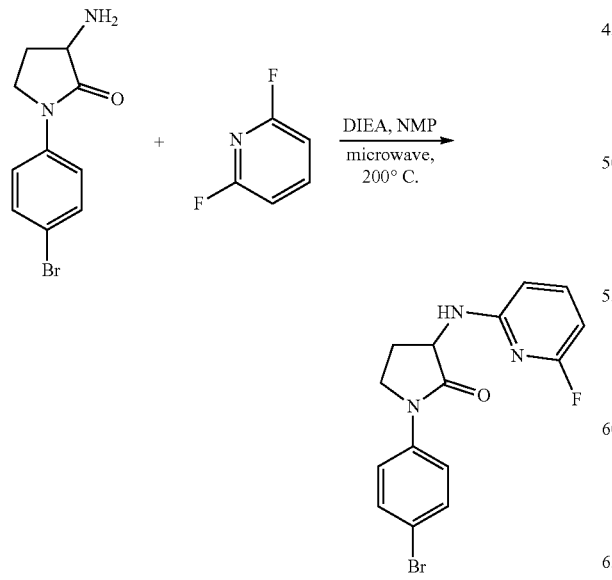

To a solution of Intermediate 4 (30 mg, 0.081 mmol) in NMP (2 mL) were added 2,6-difluoropyridine (18.7 mg, 0.16 mmol), and DIEA (0.07 mL, 0.41 mmol) at rt. The reaction was heated with microwave at 200° C. for 1.5 h. The crude product was purified by reverse phase chromatography to provided Example (17 mg, 60%) as a white solid. MS (ESI) m/z 350.0/352.0 (M+H)⁺. ¹H NMR (400 MHz, CD₃OD) δ 7.76 (s, 1H), 7.63-7.57 (m, 2H), 7.55-7.45 (m, 3H), 6.44 (dd, J=8.0, 1.9 Hz, 1H), 6.13 (dd, J=7.7, 1.8 Hz, 1H), 4.75 (dd, J=10.3, 8.6 Hz, 1H), 3.96-3.81 (m, 2H), 2.71 (dddd, J=12.3, 8.7, 5.9, 2.8 Hz, 1H), 2.19-2.02 (m, 1H).

Example 69B

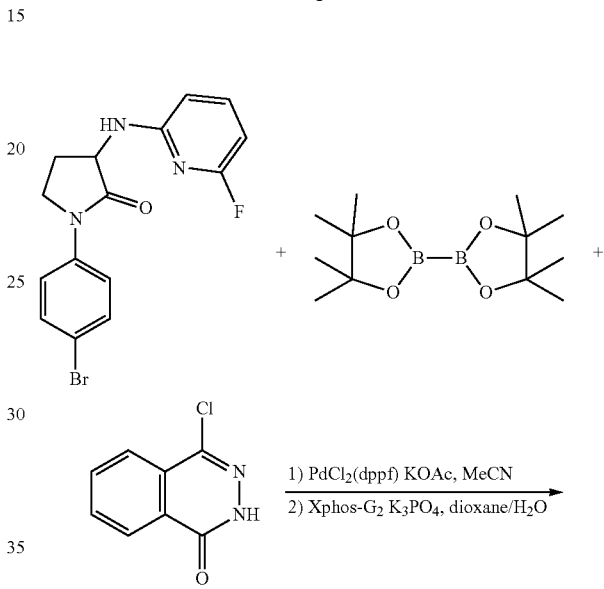

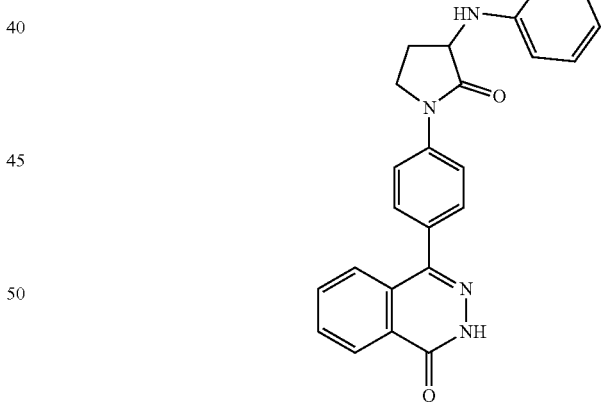

Example 69 was prepared by following a similar procedure to that described in Example 30 by replacing Example 30A with Example 69A. MS(ESI) m/z 416 (M+H)⁺. ¹H NMR (500 MHz, DMSO-d₆, ppm) δ 8.46-8.22 (m, 1H), 7.99-7.84 (m, 4H), 7.77-7.69 (m, 1H), 7.64 (d, J=8.5 Hz, 2H), 7.55 (q, J=8.0 Hz, 1H), 7.42 (d, J=7.9 Hz, 1H), 6.49 (dd, J=8.1, 1.7 Hz, 1H), 6.17 (dd, J=7.6, 1.5 Hz, 1H), 4.90-4.72 (m, 1H), 4.02-3.83 (m, 2H), 2.57 (dt, J=7.9, 4.0 Hz, 1H), 2.13-1.96 (m, 1H). Analytical HPLC: RT=1.53 min (Method D).

Example 70: 4-(4-{2-oxo-3-[(1,2,3,4-tetrahydroiso-quinolin-6-yl)amino]pyrrolidin-1-yl}phenyl)-1,2-dihydrophthalazin-1-one

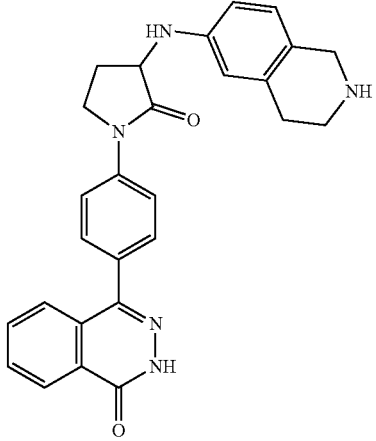 [SMILES: O=C1C(Nc2ccc3c(c2)CCNC3)CCN1c1ccc(-c2n[nH]c(=O)c3ccccc23)cc1]

Tert-butyl 6-((2-oxo-1-(4-(4-oxo-3,4-dihydrophthalazin-1-yl)phenyl)pyrrolidin-3-yl)amino)-3,4-dihydroisoquinoline-2(1H)-carboxylate (70A) was prepared by following a similar procedure to that described in Example 30 by replacing 3-(difluoromethoxy)aniline with ter t-butyl 6-amino-3,4-dihydroisoquinoline-2(1H)-carboxylate in Example 30A.

To 70A were added DCM (2 mL) and TFA (0.5 mL). After stirring at rt for 30 min, the solvent was removed. Reverse phase chromatography afforded Example 70 (21 mg, 39%) as a white solid. MS(ESI) m/z (M+H)+. 1H NMR (500 MHz, CD3OD, ppm) δ 8.49-8.41 (m, 1H), 7.95-7.87 (m, 4H), 7.85-7.79 (m, 1H), 7.66 (d, J=8.6 Hz, 2H), 7.00 (d, J=8.4 Hz, 1H), 6.74 (dd, J=8.4, 2.4 Hz, 1H), 6.66 (d, J=2.0 Hz, 1H), 4.47 (dd, J=10.1, 8.1 Hz, 1H), 4.23 (s, 2H), 4.05-3.94 (m, 2H), 3.46 (t, J=6.4 Hz, 2H), 3.05 (t, J=6.4 Hz, 2H), 2.84-2.72 (m, 1H), 2.06 (dq, J=12.3, 9.6 Hz, 1H). Analytical HPLC: RT=5.55 min (Method B).

Example 71: 4-[4-(3-{[1-methyl-3-(propan-2-yl)-1H-pyrazol-5-yl]amino}-2-oxopyrrolidin-1-yl)phenyl]-1,2-dihydrophthalazin-1-one Trifluoroacetic Acid Salt

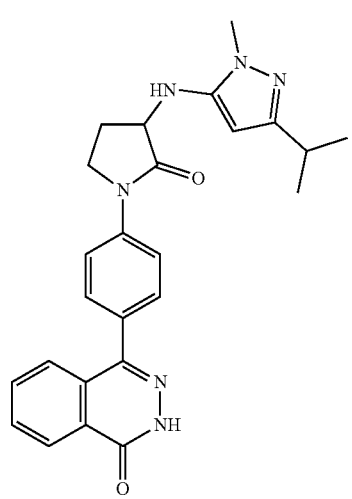 [SMILES: CC(C)c1cc(NC2CCN(c3ccc(-c4n[nH]c(=O)c5ccccc45)cc3)C2=O)n(C)n1]

Example 71 was prepared by following a similar procedure to that described in Example 30 by replacing 3-(difluoromethoxy)aniline with 3-isopropyl-1-methyl-1H-pyrazol-5-amine in Example 30A. MS(ESI) m/z 443 (M+H)+. 1H NMR (500 MHz, DMSO-d6, ppm) δ 12.85 (s, 1H), 8.42-8.29 (m, 1H), 7.97-7.83 (m, 4H), 7.75-7.67 (m, 1H), 7.64 (d, J=8.5 Hz, 2H), 5.75 (s, 1H), 4.46 (t, J=9.5 Hz, 1H), 4.01-3.81 (m, 2H), 3.63 (s, 3H), 2.85 (quin, J=6.9 Hz, 1H), 2.65-2.56 (m, 1H), 2.07 (quin, J=10.4 Hz, 1H), 1.19 (d, J=6.7 Hz, 6H). Analytical HPLC: RT=1.46 min (Method D).

Example 72: 4-[(3-methoxyphenyl)methyl]-3-methyl-1-(4-{4-oxo-3aH,4H,5H,7aH-thieno[3,2-c]pyridin-7-yl}phenyl)-4,5-dihydro-1H-1,2,4-triazol-5-one trifluoroacetic acid Salt

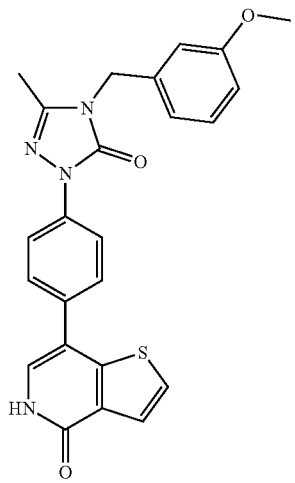

Example 72A: 7-bromothieno[3,2-c]pyridin-4(5H)-one

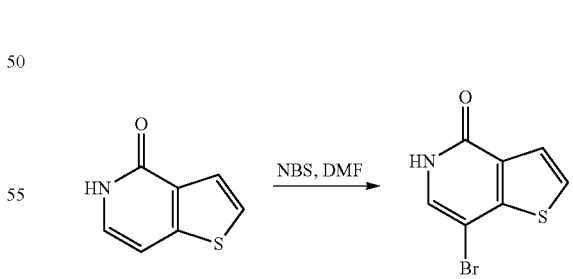

To a solution of thieno[3,2-c]pyridin-4(5H)-one (650 mg, 4.30 mmol) in DMF (5 mL) was added NBS (765 mg, 4.30 mmol) portion wise over 10 min at 0° C. The reaction mixture was stirred at rt for 16 h. The reaction mixture was diluted with cold water (100 mL) to form a solid, which was collected by filtration and dried in vacuum to afford Example 72A (600 mg, 58%). MS(ESI) m/z 230/232 (M+H)+.

Example 72B

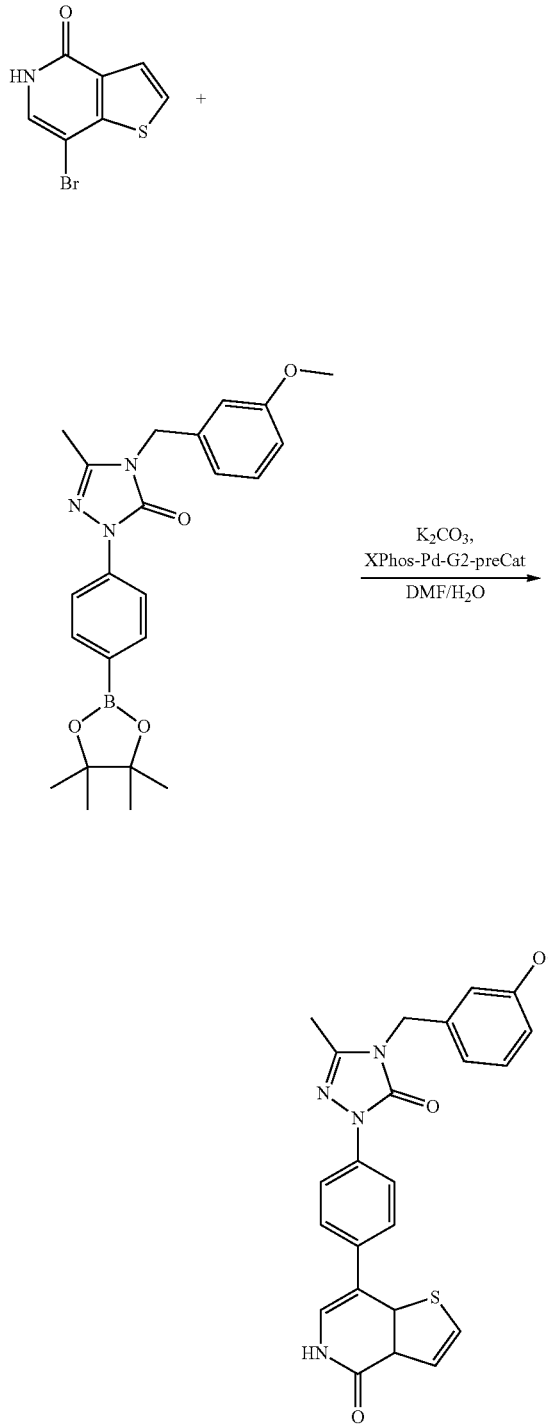

Example 72 was prepared by following a similar procedure to that described in Example 30. MS(ESI) m/z 445 (M+H)+. ¹H NMR (500 MHz, DMSO-d₆, ppm) δ 11.73 (s, 1H) 8.02 (d, J=8.8 Hz, 2H), 7.67-7.73 (m, 3H), 7.57 (d, J=5.2 Hz, 1H), 7.29-7.36 (m, 2H) 6.85-6.91 (m, 3H), 4.91 (s, 2H), 3.75 (s, 3H), 2.25 (s, 3H). Analytical HPLC: RT=1.60 min (Method C).

Example 73: 4-(4-{2-oxo-3-[3-(trifluoromethoxy)phenoxy]pyrrolidin-1-yl}phenyl)-1,2-dihydrophthalazin-1-one

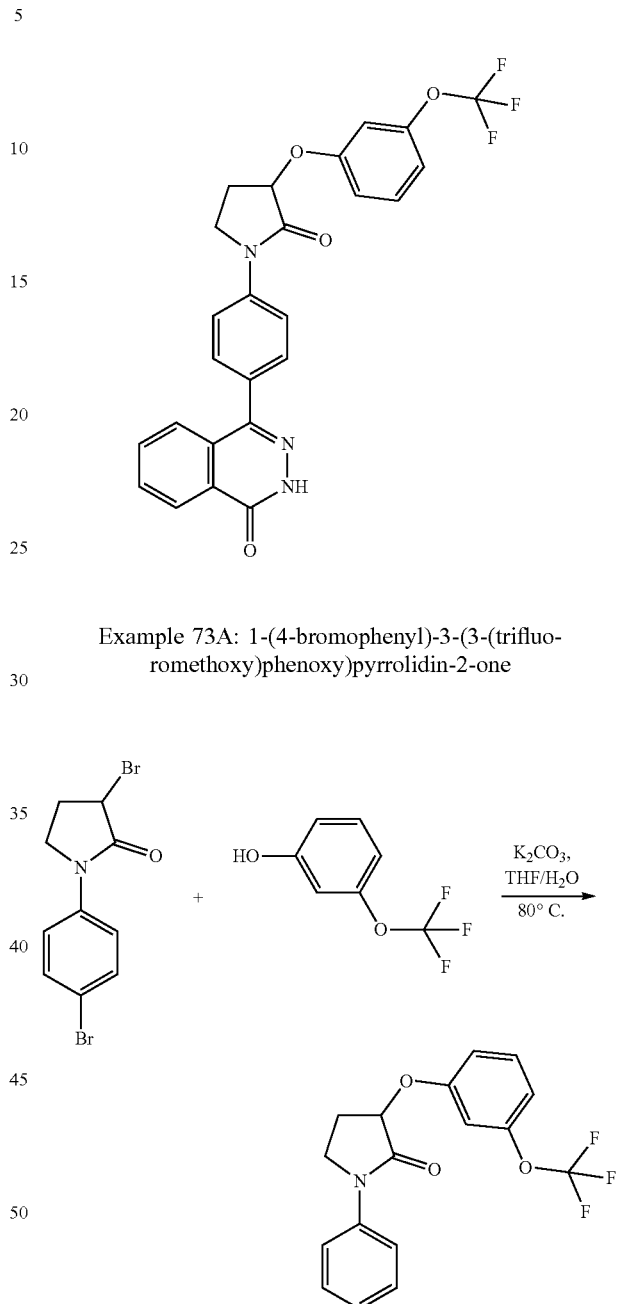

Example 73A: 1-(4-bromophenyl)-3-(3-(trifluoromethoxy)phenoxy)pyrrolidin-2-one To a solution of Intermediate 2 (50 mg, 0.16 mmol) in THF (4 mL) and H₂O (0.3 mL) were added 3-(trifluoromethoxy)phenol (42 mg, 0.24 mmol) and K₂CO₃ (65 mg, 0.470 mmol) at rt. The reaction was heated in a sealed vial at 80° C. for 16 h. The solvent was removed. The crude product was purified by normal phase chromatography to provide Example 73A (56 mg, 86%) as a white solid. MS (ESI) m/z 416/418 (M+H)+. ¹H NMR (400 MHz, CDCl₃) 7.64-7.56 (m, 2H), 7.54-7.47 (m, 2H), 7.31 (t, J=8.3 Hz, 1H), 7.03 (dd, J=8.4, 1.8 Hz, 1H), 6.95 (s, 1H), 6.88 (dt, J=8.2, 1.1 Hz, 1H), 5.03 (t, J=7.6 Hz, 1H), 3.99-3.80 (m, 2H), 2.71 (dtd, J=13.4, 7.5, 3.7 Hz, 1H), 2.33 (ddt, J=13.3, 8.6, 7.3 Hz, 1H).

Example 73B

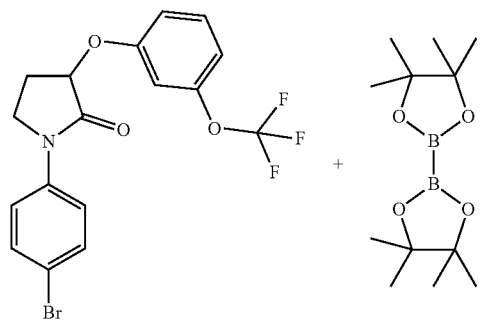

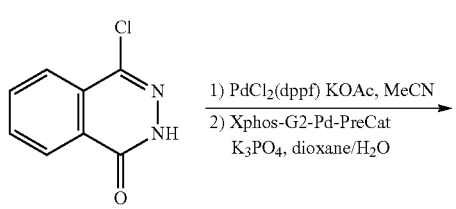

Example 73 was prepared by following a similar procedure to that described in Example 30 by replacing Example 30A with Example 73A. MS(ESI) m/z 482.3 (M+H)⁺. ¹H NMR (500 MHz, DMSO-d₆, ppm) δ 12.87 (s, 1H), 8.34 (d, J=7.8 Hz, 1H), 7.97-7.83 (m, 4H), 7.71 (d, J=7.5 Hz, 1H), 7.65 (d, J=8.3 Hz, 2H), 7.45 (t, J=8.2 Hz, 1H), 7.14 (d, J=8.5 Hz, 1H), 7.12 (br. s., 1H), 6.99 (d, J=8.0 Hz, 1H), 5.40 (t, J=8.2 Hz, 1H), 4.07-3.82 (m, 2H), 2.76 (d, J=6.1 Hz, 1H), 2.25-2.03 (m, 1H). Analytical HPLC: RT=1.88 min (Method D).

Example 74: 2-({2-oxo-1-[4-(4-oxo-3,4-dihydrophthalazin-1-yl)phenyl]pyrrolidin-3-yl}amino)pyridine-4-carbonitrile Trifluoroacetic Acid Salt

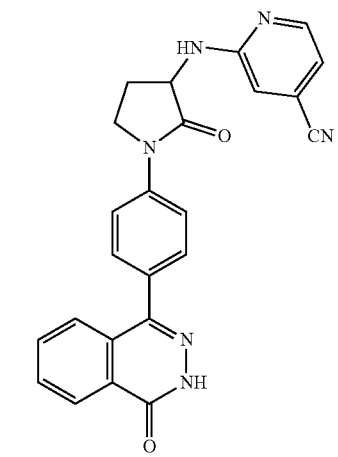 [SMILES: N#Cc1ccnc(NC2CCN(c3ccc(-c4n[nH]c(=O)c5ccccc45)cc3)C2=O)c1]

Example 74 was prepared by following a similar procedure to that described in Example 69 by replacing 2,6-difluoropyridine with 2-fluoroisonicotinonitrile in Example 69A. MS(ESI) m/z 423 (M+H)⁺. ¹H NMR (500 MHz, DMSO-d₆, ppm) δ 12.84 (s, 1H), 8.41-8.29 (m, 1H), 8.17 (d, J=5.2 Hz, 1H), 7.95-7.82 (m, 4H), 7.75-7.68 (m, 1H), 7.62 (d, J=8.9 Hz, 2H), 7.57 (d, J=7.9 Hz, 1H), 6.97 (s, 1H), 6.86 (d, J=4.9 Hz, 1H), 4.97-4.81 (m, 1H), 4.07-3.77 (m, 2H), 2.56 (d, J=2.7 Hz, 1H), 2.14-1.99 (m, 1H). Analytical HPLC: RT=1.48 min (Method D).

Example 75: 4-(4-{3-[(2-methyl-1,2,3,4-tetrahydroisoquinolin-6-yl)amino]-2-oxopyrrolidin-1-yl}phenyl)-1,2-dihydrophthalazin-1-one

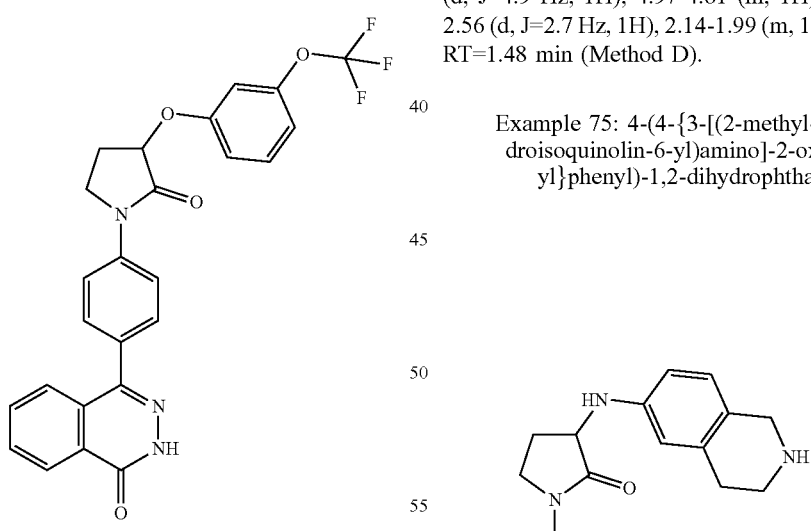

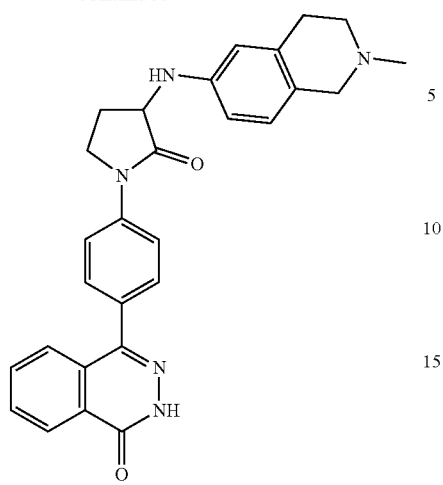

To a solution of Example 70 (18 mg, 0.040 mmol) in DCE (2 mL) were added paraformaldehyde (3.6 mg, 0.12 mmol), NaBH(OAc)₃ (25 mg, 0.12 mmol) and two drops of acetic acid at rt. The reaction was stirred under N₂ at rt for 16 h. Purification by reverse phase chromatography afforded Example 75 (6.5 mg, 35%). MS(ESI) m/z 466 (M+H)⁺. ¹H NMR (500 MHz, DMSO-d₆, ppm) δ 12.85 (s, 1H), 8.41-8.29 (m, 1H), 7.97-7.84 (m, 4H), 7.70 (d, J=7.0 Hz, 1H), 7.62 (d, J=8.5 Hz, 2H), 6.85 (d, J=8.5 Hz, 1H), 6.59 (d, J=8.5 Hz, 1H), 6.52 (s, 1H), 5.88 (br. s., 1H), 4.47-4.35 (m, 1H), 3.89 (d, J=8.9 Hz, 2H), 3.06 (br. s., 2H), 2.86 (br. s., 2H), 2.64 (br. s., 4H), 1.97-1.85 (m, 1H). Analytical HPLC: RT=1.13 min (Method C).

Example 76: 4-(4-{3-[(3,4-dihydro-2H-1,5-benzodioxepin-7-yl)amino]-2-oxopyrrolidin-1-yl}phenyl)-1,2-dihydrophthalazin-1-one (enantiomer 1), and Example 77: 4-(4-{3-[(3,4-dihydro-2H-1,5-benzo dioxepin-7-yl)amino]-2-oxopyrrolidin-1-yl}phenyl)-1,2-dihydrophthalazin-1-one (enantiomer 2)

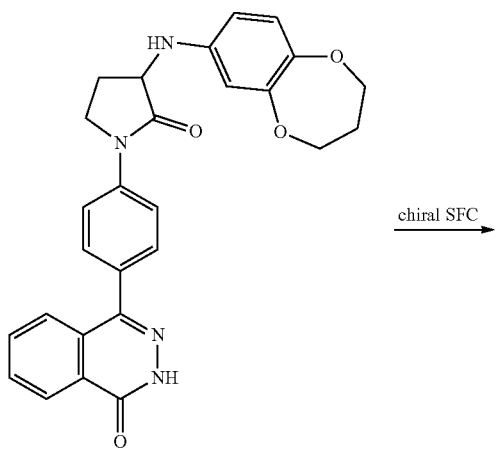

chiral SFC →

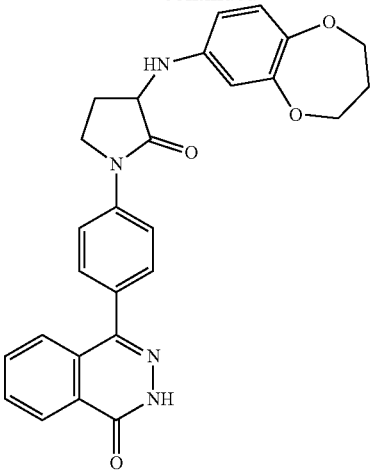

Enantiomer 1
Example 76

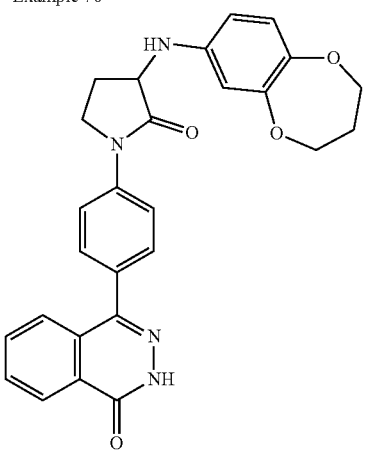

Enantiomer 2
Example 77

Example 34 was subjected to SFC chiral separation (column: (R,R) Whelk-O1, 21×250 mm, 5 micron; mobile phase: 55% MeOH/45% CO₂; flow conditions: 45 mL/min; pressure: 140 Bar; temperature: 40° C.; detector wavelength: 220 nm). Two enantiomers were obtained as white solids.

Example 76, peak 1, enantiomer 1, ee>99%. MS (ESI) m/z 469 (M+H)⁺. ¹H NMR (400 MHz, DMSO-d₆) δ 12.86 (s, 1H), 8.41-8.29 (m, 1H), 7.97-7.86 (m, 4H), 7.74-7.69 (m, 1H), 7.67-7.59 (m, 2H), 6.75 (d, J=8.6 Hz, 1H), 6.38 (d, J=2.6 Hz, 1H), 6.32 (dd, J=8.7, 2.8 Hz, 1H), 5.79 (br. s., 1H), 4.34 (t, J=9.0 Hz, 1H), 4.07-4.01 (m, 2H), 3.95 (t, J=5.4 Hz, 2H), 3.92-3.82 (m, 2H), 2.65-2.56 (m, 1H), 2.06-1.98 (m, 2H), 1.96-1.83 (m, 1H). Analytical HPLC: RT=10.51 min (Method A).

Example 77, peak 2, enantiomer 2, ee>99%. MS (ESI) m/z 469 (M+H)⁺. ¹H NMR (400 MHz, DMSO-d₆) δ 12.86 (s, 1H), 8.41-8.29 (m, 1H), 7.97-7.86 (m, 4H), 7.74-7.69 (m, 1H), 7.67-7.59 (m, 2H), 6.75 (d, J=8.6 Hz, 1H), 6.38 (d, J=2.6 Hz, 1H), 6.32 (dd, J=8.7, 2.8 Hz, 1H), 5.79 (br. s., 1H), 4.34 (t, J=9.0 Hz, 1H), 4.07-4.01 (m, 2H), 3.95 (t, J=5.4 Hz, 2H), 3.92-3.82 (m, 2H), 2.65-2.56 (m, 1H), 2.06-1.98 (m, 2H), 1.96-1.83 (m, 1H). Analytical HPLC: RT=10.42 min (Method A).

Example 78: 4-[4-(3-{[3-(difluoromethoxy)phenyl]amino}-2-oxopyrrolidin-1-yl)phenyl]-1,2-dihydroisoquinolin-1-one (enantiomer 1), and Example 79: 4-[4-(3-{[3-(difluoromethoxy)phenyl]amino}-2-oxopyrrolidin-1-yl)phenyl]-1,2-dihydroisoquinolin-1-one (enantiomer 2)

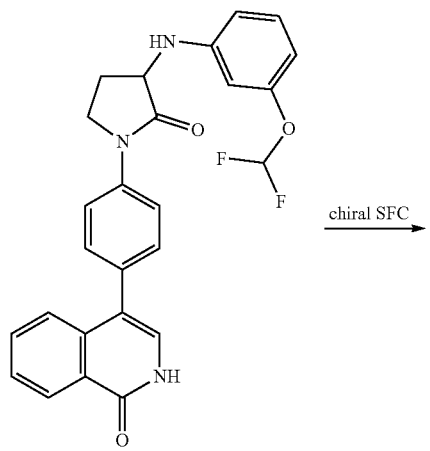

Racemic

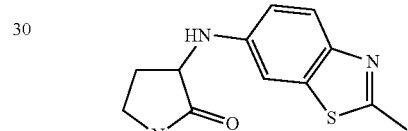

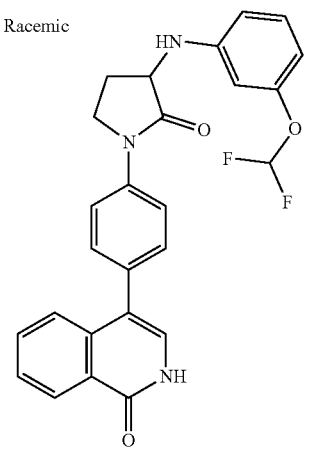

Enantiomer 1
Example 78

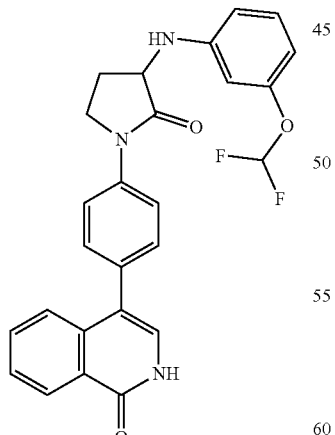

Enantiomer 2
Example 79

Example 58 (racemic) was subjected to SFC chiral separation (column: (R,R) Whelk-O1, 21×250 mm, 5 micron; mobile phase: 50% MeOH/50% CO$_2$; flow conditions: 45 mL/min; pressure: 150 Bar; temperature: 40° C.; detector wavelength: 220 nm). Two enantiomers were obtained as white solids.

Example 78, peak 1, enantiomer 1, ee>99%. MS (ESI) m/z 462 (M+H)$^+$. $^1$H NMR (500 MHz, DMSO-d$_6$) δ 11.45 (d, J=5.5 Hz, 1H), 8.30 (d, J=8.0 Hz, 1H), 7.83 (d, J=8.8 Hz, 2H), 7.75-7.67 (m, 1H), 7.58-7.50 (m, 2H), 7.47 (d, J=8.8 Hz, 2H), 7.32-6.96 (m, 3H), 6.60 (dd, J=8.3, 1.7 Hz, 1H), 6.54-6.48 (m, 1H), 6.36 (dd, J=8.0, 1.9 Hz, 1H), 6.31 (d, J=7.2 Hz, 1H), 4.50-4.40 (m, 1H), 3.96-3.82 (m, 2H), 2.67-2.61 (m, 1H), 1.98-1.87 (m, 1H). Analytical HPLC: RT=11.23 min (Method A).

Example 79, peak 2, enantiomer 2, ee>99%. MS (ESI) m/z 462 (M+H)$^+$. $^1$H NMR (500 MHz, DMSO-d$_6$) δ 11.46 (d, J=4.7 Hz, 1H), 8.39-8.25 (m, 1H), 7.83 (d, J=8.8 Hz, 2H), 7.76-7.67 (m, 1H), 7.59-7.50 (m, 2H), 7.47 (d, J=8.5 Hz, 2H), 7.31-6.96 (m, 3H), 6.60 (dd, J=8.1, 1.8 Hz, 1H), 6.52 (t, J=2.1 Hz, 1H), 6.36 (dd, J=7.8, 2.1 Hz, 1H), 6.31 (d, J=7.4 Hz, 1H), 4.51-4.40 (m, 1H), 3.97-3.83 (m, 2H), 2.70-2.59 (m, 1H), 1.99-1.86 (m, 1H). Analytical HPLC: RT=11.22 min (Method A).

Example 80: 4-(4-{3-[(2-methyl-1,3-benzothiazol-6-yl)amino]-2-oxopyrrolidin-1-yl}phenyl)-1,2-dihydrophthalazin-1-one

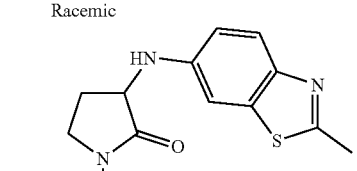

Racemic

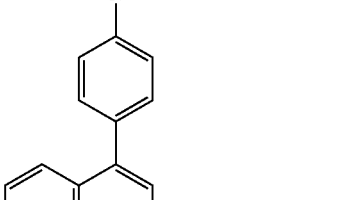

Enantiomer 1
Example 80

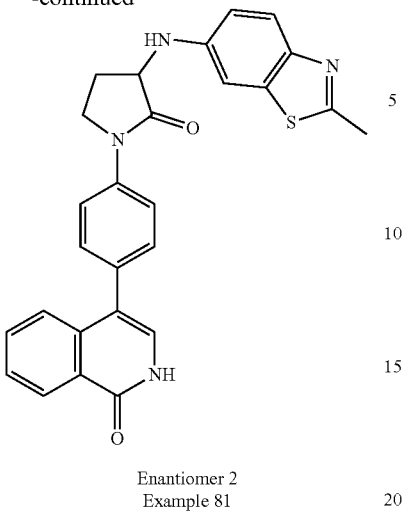

Enantiomer 2
Example 81

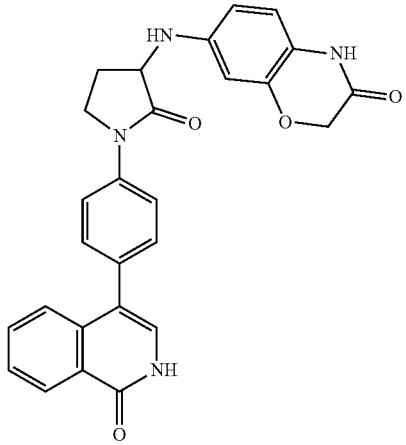

Enantiomer 1
Example 82

Example 66 (racemic) was subjected to SFC chiral separation (column: Chiralcel OJ, 21×250 mm, 5 micron; mobile phase: 45% MeOH/55% $CO_2$; flow conditions: 45 mL/min; pressure: 150 Bar; temperature: 40° C.; detector wavelength: 220 nm). Two enantiomers were obtained as white solids.

Example 80, peak 1, enantiomer 1, ee>97%. MS (ESI) m/z 468 $(M+H)^+$. $^1$H NMR (400 MHz, DMSO-$d_6$) δ 12.83 (s, 1H), 8.38-8.31 (m, 1H), 7.97-7.85 (m, 4H), 7.75-7.69 (m, 1H), 7.63 (dd, J=11.2, 8.8 Hz, 3H), 7.24 (d, J=2.0 Hz, 1H), 6.92 (dd, J=8.9, 2.3 Hz, 1H), 6.24 (d, J=7.0 Hz, 1H), 4.58-4.44 (m, 1H), 4.02-3.84 (m, 2H), 2.77-2.70 (m, 1H), 2.68 (s, 3H), 2.06-1.91 (m, 1H). Analytical HPLC: RT=6.03 min (Method A).

Example 81, peak 2, enantiomer 2, ee>96%. MS (ESI) m/z 468 $(M+H)^+$. $^1$H NMR (400 MHz, DMSO-$d_6$) δ 12.83 (s, 1H), 8.35 (dd, J=6.4, 2.6 Hz, 1H), 7.97-7.86 (m, 4H), 7.77-7.69 (m, 1H), 7.68-7.58 (m, 3H), 7.24 (d, J=2.2 Hz, 1H), 6.92 (dd, J=8.8, 2.2 Hz, 1H), 6.24 (d, J=7.0 Hz, 1H), 4.56-4.44 (m, 1H), 4.02-3.83 (m, 2H), 2.77-2.70 (m, 1H), 2.69 (s, 3H), 2.05-1.87 (m, 1H). Analytical HPLC: RT=6.04 min (Method A).

Example 82: 7-({2-oxo-1-[4-(4-oxo-3,4-dihydrophthalazin-1-yl)phenyl]pyrrolidin-3-yl}amino)-3,4-dihydro-2H-1,4-benzoxazin-3-one (enantiomer 1), and Example 83: 7-({2-oxo-1-[4-(4-oxo-3,4-dihydrophthalazin-1-yl)phenyl]pyrrolidin-3-yl}amino)-3,4-dihydro-2H-1,4-benzoxazin-3-one (enantiomer 2)

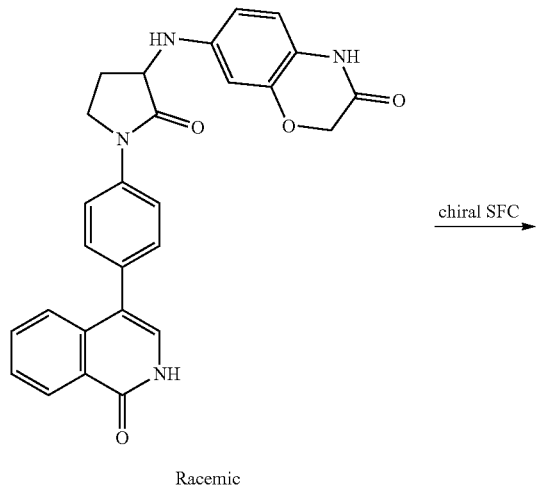

Racemic

→ chiral SFC

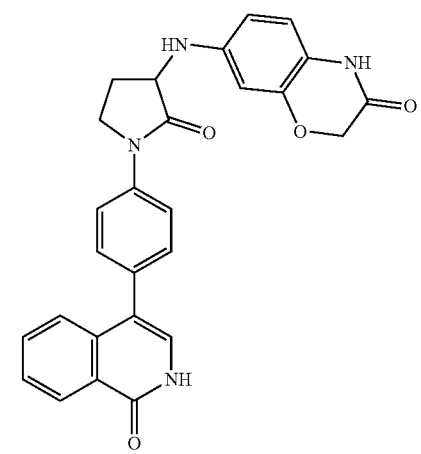

Enantiomer 2
Example 83

Example 62 (racemic) was subjected to SFC chiral separation (column: (R,R) Whelk-O1, 21×250 mm, 5 micron; mobile phase: 60% MeOH/40% $CO_2$; flow conditions: 45 mL/min; pressure: 125 Bar; temperature: 40° C.; detector wavelength: 220 nm). Two enantiomers were obtained as white solids.

Example 82, peak 1, enantiomer 1, ee>97%. MS (ESI) m/z 468 $(M+H)^+$. $^1$H NMR (400 MHz, DMSO-$d_6$) δ 12.83 (br. s., 1H), 10.32 (s, 1H), 8.35 (d, J=7.0 Hz, 1H), 7.92-7.89 (m, 4H), 7.72 (d, J=9.2 Hz, 1H), 7.64 (d, J=8.6 Hz, 2H), 6.66 (d, J=8.4 Hz, 1H), 6.39 (s, 1H), 6.35 (d, J=8.4 Hz, 1H), 5.83 (d, J=7.3 Hz, 1H), 4.46 (s, 2H), 4.35 (q, J=8.6 Hz, 1H), 3.89 (br. s., 2H), 2.61 (br. s., 1H), 1.97-1.87 (m, 1H). Analytical HPLC: RT=6.56 min (Method B).

Example 83, peak 2, enantiomer 2, ee>96%. MS (ESI) m/z 468 $(M+H)^+$. $^1$H NMR (400 MHz, DMSO-$d_6$) δ 12.87 (s, 1H), 10.37 (s, 1H), 8.42-8.29 (m, 1H), 7.99-7.86 (m, 4H), 7.78-7.70 (m, 1H), 7.68-7.59 (m, 2H), 6.67 (d, J=8.4 Hz, 1H), 6.40 (d, J=2.4 Hz, 1H), 6.36 (dd, J=8.6, 2.4 Hz, 1H), 4.47 (s, 2H), 4.38 (dd, J=9.9, 8.4 Hz, 1H), 3.98-3.84 (m, 2H), 2.61 (dd, J=12.0, 6.1 Hz, 1H), 1.99-1.85 (m, 1H). Analytical HPLC: RT=6.56 min (Method B).

Example 84: 4-(4-{2-oxo-3-[3-(trifluoromethoxy) phenoxy]pyrrolidin-1-yl}phenyl)-1,2-dihydrophthalazin-1-one (enantiomer 1), and Example 85: 4-(4-{2-oxo-3-[3-(trifluoromethoxy) phenoxy]pyrrolidin-1-yl}phenyl)-1,2-dihydrophthalazin-1-one (enantiomer 2)

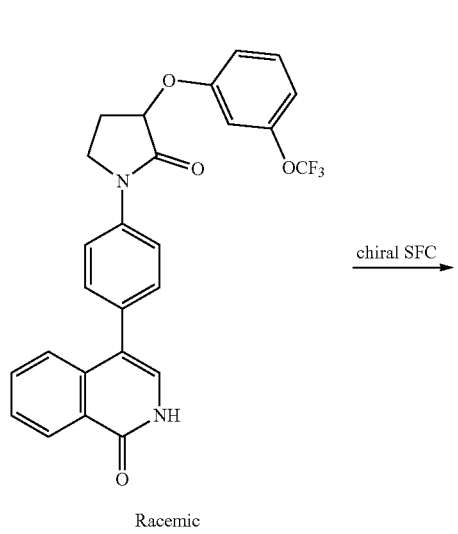

Racemic chiral SFC

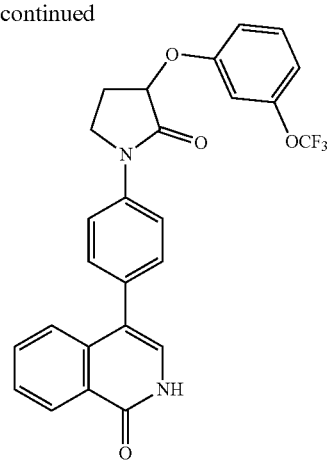

Enantiomer 2
Example 85

Example 73 (racemic) was subjected to SFC chiral separation (column: Chiralcel OJ, 21×250 mm, 5 micron; mobile phase: 45% MeOH/55% $CO_2$; flow conditions: 45 mL/min; pressure: 125 Bar; temperature: 40° C.; detector wavelength: 220 nm). Two enantiomers were obtained as white solids.

Example 84, peak 1, enantiomer 1, ee>99%. MS (ESI) m/z 482 (M+H)$^+$. $^1$H NMR (400 MHz, DMSO-d$_6$) δ 12.84 (s, 1H), 8.39-8.31 (m, 1H), 7.97-7.87 (m, 4H), 7.75-7.69 (m, 1H), 7.66 (d, J=8.8 Hz, 2H), 7.50-7.41 (m, 1H), 7.18-7.10 (m, 2H), 7.00 (d, J=8.1 Hz, 1H), 5.41 (t, J=8.3 Hz, 1H), 4.05-3.85 (m, 2H), 2.84-2.71 (m, 1H), 2.24-2.11 (m, 1H). Analytical HPLC: RT=9.48 min (Method A).

Example 85, peak 2, enantiomer 2, ee>99%. MS (ESI) m/z 482 (M+H)$^+$. $^1$H NMR (400 MHz, DMSO-d$_6$) δ 12.84 (s, 1H), 8.38-8.32 (m, 1H), 7.98-7.86 (m, 4H), 7.76-7.69 (m, 1H), 7.66 (d, J=8.6 Hz, 2H), 7.51-7.41 (m, 1H), 7.19-7.10 (m, 2H), 7.00 (d, J=8.1 Hz, 1H), 5.41 (t, J=8.3 Hz, 1H), 4.04-3.88 (m, 2H), 2.84-2.72 (m, 1H), 2.21-2.14 (m, 1H). Analytical HPLC: RT=9.37 min (Method A).

Example 86: 4-{4-[3-(3-methoxyphenoxy)-2-oxopyrrolidin-1-yl]phenyl}-1,2-dihydrophthalazin-1-one Trifluoroacetic Acid Salt

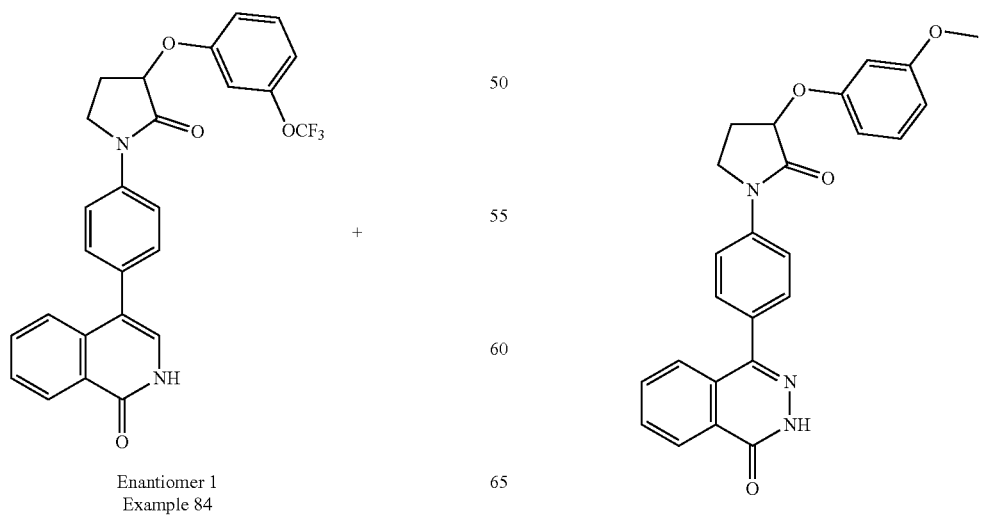

Enantiomer 1
Example 84

+

Example 86 was prepared by following a similar procedure to that described in Example 73 by replacing 3-trifluoromethoxyphenol with 3-methoxyphenol in Example 73A. MS(ESI) m/z 428.1 (M+H)+. 1H NMR (500 MHz, DMSO-d6, ppm) δ 12.85 (s, 1H), 8.39-8.27 (m, 1H), 7.98-7.83 (m, 4H), 7.71 (d, J=7.0 Hz, 1H), 7.65 (d, J=8.5 Hz, 2H), 7.22 (t, J=8.1 Hz, 1H), 6.70-6.61 (m, 2H), 6.60-6.54 (m, 1H), 5.28 (t, J=8.1 Hz, 1H), 4.04-3.85 (m, 2H), 3.75 (s, 3H), 2.82-2.67 (m, 1H), 2.19-2.05 (m, 1H). Analytical HPLC: RT=1.68 min (Method C).

Example 87: 4-{4-[3-(2-fluoro-5-methoxyphenoxy)-2-oxopyrrolidin-1-yl]phenyl}-1,2-dihydrophthalazin-1-one

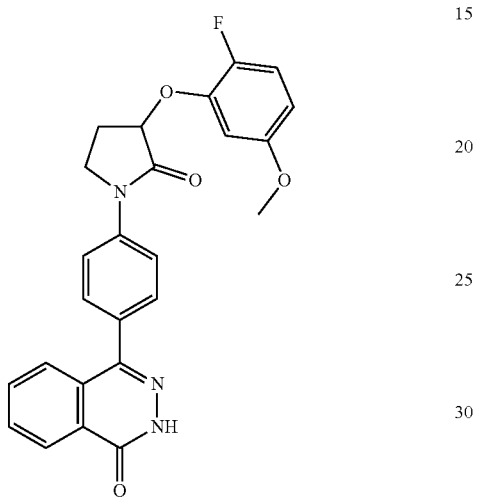

Example 87 was prepared by following a similar procedure to that described in Example 73 by replacing 3-trifluoromethoxyphenol with 2-fluoro-5-methoxyphenol in Example 73A. MS(ESI) m/z 446.2 (M+H)+. 1H NMR (500 MHz, DMSO-d6, ppm) δ 12.87 (s, 1H), 8.34 (d, J=6.6 Hz, 1H), 7.90 (d, J=7.6 Hz, 4H), 7.71 (d, J=7.0 Hz, 1H), 7.65 (d, J=8.2 Hz, 2H), 7.16 (t, J=9.8 Hz, 1H), 6.95 (d, J=4.8 Hz, 1H), 6.54 (d, J=8.8 Hz, 1H), 5.36 (t, J=7.9 Hz, 1H), 4.03-3.94 (m, 1H), 3.94-3.85 (m, 1H), 3.74 (s, 3H), 2.75 (br. s., 1H), 2.24-2.07 (m, 1H). Analytical HPLC: RT=1.61 min (Method C).

Example 88: 4-{4-[3-(4-fluoro-3-methoxyphenoxy)-2-oxopyrrolidin-1-yl]phenyl}-1,2-dihydrophthalazin-1-one

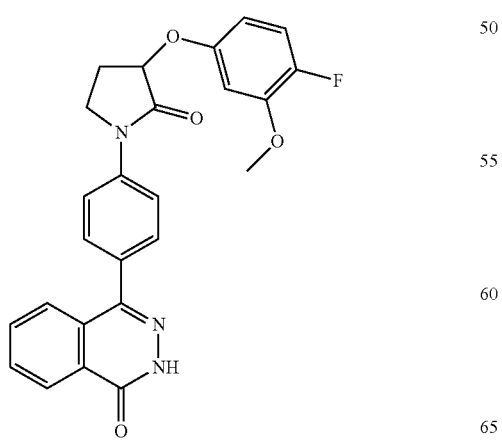

Example 88 was prepared by following a similar procedure to that described in Example 73 by replacing 3-trifluoromethoxyphenol with 4-fluoro-5-methoxyphenol in Example 73A. MS(ESI) m/z 446 (M+H)+. 1H NMR (500 MHz, DMSO-d6, ppm) δ 12.87 (s, 1H), 8.35 (d, J=7.2 Hz, 1H), 7.92 (d, J=7.2 Hz, 4H), 7.71 (d, J=6.8 Hz, 1H), 7.66 (d, J=7.9 Hz, 2H), 7.15 (t, J=10.0 Hz, 1H), 6.89 (d, J=6.6 Hz, 1H), 6.64 (d, J=7.7 Hz, 1H), 5.28 (t, J=8.1 Hz, 1H), 4.03-3.94 (m, 1H), 3.91 (d, J=7.8 Hz, 1H), 3.83 (s, 3H), 2.75 (br. s., 1H), 2.18-2.06 (m, 1H). Analytical HPLC: RT=1.59 min (Method C).

Example 89: 4-{4-[3-(3-fluoro-5-methoxyphenoxy)-2-oxopyrrolidin-1-yl]phenyl}-1,2-dihydrophthalazin-1-one

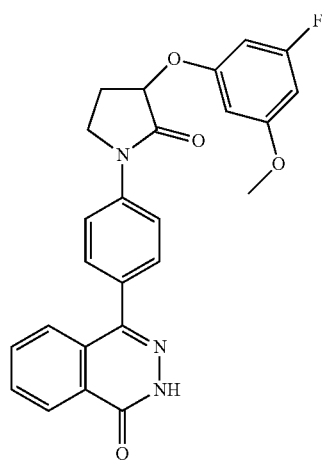 [SMILES: COc1cc(F)cc(OC2CCN(c3ccc(-c4n[nH]c(=O)c5ccccc45)cc3)C2=O)c1]

Example 89 was prepared by following a similar procedure to that described in Example 73 by replacing 3-trifluoromethoxyphenol with 3-fluoro-5-methoxyphenol in Example 73A. MS(ESI) m/z 446 (M+H)+. 1H NMR (500 MHz, DMSO-d6) δ 12.84 (s, 1H), 8.34 (d, J=7.9 Hz, 1H), 7.98-7.84 (m, 4H), 7.71 (d, J=7.0 Hz, 1H), 7.65 (d, J=8.5 Hz, 2H), 6.58 (d, J=11.0 Hz, 1H), 6.51 (s, 1H), 6.47 (d, J=11.0 Hz, 1H), 5.34 (t, J=8.1 Hz, 1H), 4.03-3.94 (m, 1H), 3.93-3.85 (m, 1H), 3.76 (s, 3H), 2.82-2.68 (m, 1H), 2.18-2.07 (m, 1H). Analytical HPLC: RT=1.78 min (Method C).

What is claimed is:

1. A compound of Formula (I):

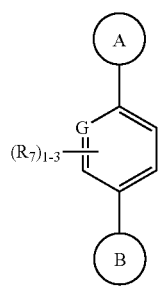

(I)

or a stereoisomer, a tautomer, a pharmaceutically acceptable salt thereof, wherein:

Ring A is independently selected from

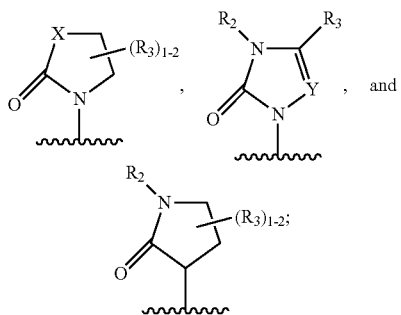

Ring B is independently selected from

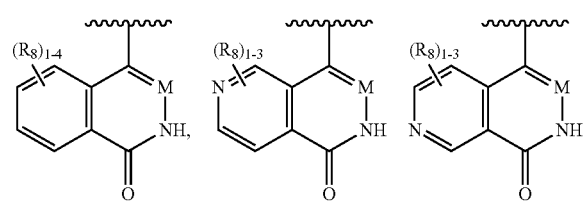

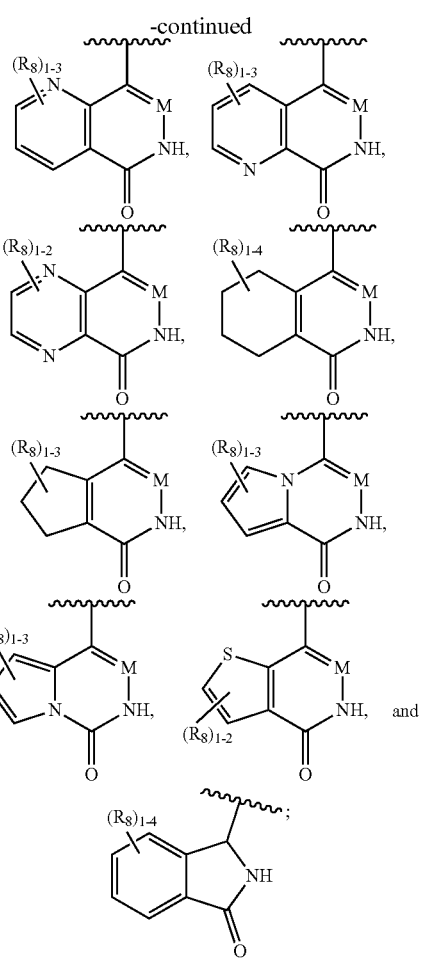

G is independently selected from N and $CR_7$;
M is independently selected from N and $CR_9$;
X is independently selected from $CR_1$, $NR_2$, and O;
Y is independently selected from $CR_3$ and N;
L is absent or independently selected from —$NR_4$—, —C(O)$NR_4$(C$R_4R_4$)$_n$—, and —O—;
$R_1$ is L-$R^5$;
$R_2$ is —(C$R_4R_4$)$_n$—$R_5$;

$R_3$ is independently selected from H, $C_{1-4}$alkyl substituted with 0-4 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H and $C_{1-4}$alkyl substituted with 0-4 $R_e$;

$R_5$ is independently selected from $C_{3-6}$ cycloalkyl, heterocyclyl, aryl and heteroaryl, each substituted with 1-5 $R_6$;

alternatively, when L is —$NR_4$—, —$C(O)NR_4$—, $R_4$ and $R_5$ together with the nitrogen atom to which they are both attached form a heterocyclic ring substituted with 1-5 $R_6$;

$R_6$ is independently selected from H, =O, F, Cl, Br, $C_{1-4}$alkyl, $C_{2-4}$alkenyl, $C_{2-4}$alkynyl, nitro, —$(CR_dR_d)_r$ $S(O)_pR_c$, —$(CR_dR_d)_rS(O)_pNR_aR_a$, —$(CR_dR_d)_rNR_aS(O)_pR_c$, —$(CR_dR_d)_rOR_b$, —$(CR_dR_d)_rCN$, —$(CR_dR_d)_rNR_aR_a$, —$(CR_dR_d)_rNR_aC(=O)R_b$, —$(CR_dR_d)_rNR_aC(=O)NR_aR_a$, —$(CR_dR_d)_rNR_aC(=O)OR_b$, —$(CR_dR_d)_r$ $C(=O)R_b$, —$(CR_dR_d)_rC(=O)NR_aR_a$, —$(CR_dR_d)_r$ $C(=O)R_b$, —$(CR_dR_d)_rOC(=O)R_b$, —$(CR_dR_d)_rOC(=O)NR_aR_a$, —$(CR_dR_d)_r$-cycloalkyl, —$(CR_dR_d)_r$-heterocyclyl, —$(CR_dR_d)_r$-aryl, and —$(CR_dR_d)_r$-heteroaryl, wherein said alkyl, cycloalkyl, heterocyclyl, aryl, or heteroaryl is substituted with 0-4 $R_e$;

$R_7$ is independently selected from H, F, Cl, Br, CN, $C_{1-4}$ alkyl substituted with 0-3 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rCN$, —$(CH_2)_rNR_aC(=O)R_b$, —$(CH_2)_r$ $NR_aC(=O)OR_b$, —$(CH_2)_rOC(=O)NR_aR_a$, —$(CH_2)_r$ $NR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_8$ is independently selected from H, F, Cl, Br, —$(CH_2)_r$ $OR_b$, $(CH_2)_rS(O)_pR_c$, —$(CH_2)_rC(=O)R_b$, —$(CH_2)_r$ $NR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_r$ $NR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_9$ is independently selected from H and $C_{1-4}$alkyl substituted with 0-4 $R_e$;

$R_a$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$— $C_{3-10}$carbocyclyl substituted with 0-5 $R_e$, and —$(CH_2)_r$-heterocyclyl substituted with 0-5 $R_e$;

$R_c$ is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$ is independently selected from H and $C_{1-4}$alkyl substituted with 0-5 $R_e$;

$R_e$ is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, —$(CH_2)_r$-aryl, —$(CH_2)_r$-heteroaryl, F, Cl, Br, CN, $NO_2$, =O, $CO_2H$, —$(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)OR_d$, $OC(=O)NR_fR_f$ and —$(CH_2)_rNR_fR_f$;

$R_f$ is independently selected from H, F, Cl, Br, CN, OH, $C_{1-5}$alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

n, at each occurrence, is independently selected from 0, 1, 2, and 3;

p, at each occurrence, is independently selected from 0, 1, and 2; and r is independently selected from 0, 1, 2, 3, and 4.

2. The compound of claim 1, having Formula (II):

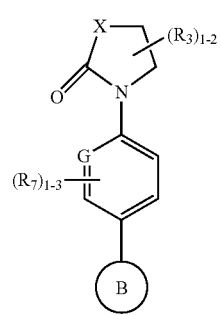

or a stereoisomer, a tautomer, or a pharmaceutically acceptable salt thereof, wherein:

Ring B is selected from

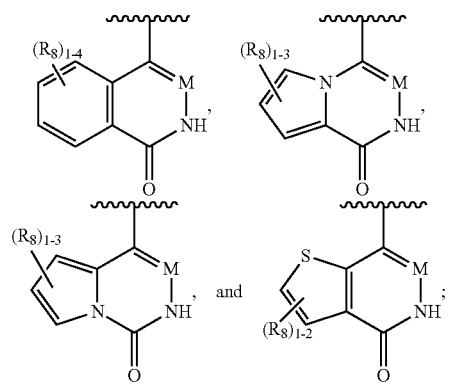

G is selected from N and $CR_7$;
M is independently selected from N and $CR_9$;
X is independently selected from $CR_1$, $NR_2$, and O;
L is absent or independently selected from —$NR_4$—, —$C(O)NR_4(CR_4R_4)_n$—, and —O—;
$R_1$ is L-$R_5$;
$R_2$ is —$(CR_4R_4)_n$—$R_5$;

$R_3$ is independently selected from H, $C_{1-4}$alkyl substituted with 0-4 $R_e$, $(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H and $C_{1-4}$alkyl substituted with 0-4 $R_e$;

$R_5$ is independently selected from $C_{3-6}$ cycloalkyl, heterocyclyl, aryl and heteroaryl, each substituted with 1-5 $R_6$;

alternatively, when L is —$NR_4$—, —$C(O)NR_4$—, $R_4$ and $R_5$ together with the nitrogen atom to which they are both attached form a heterocyclic ring substituted with 1-5 $R_6$;

$R_6$ is independently selected from H, =O, F, Cl, Br, $C_{1-4}$alkyl, $C_{2-4}$alkenyl, $C_{2-4}$alkynyl, nitro, —$(CR_dR_d)_rS(O)_pR_c$, —$(CR_dR_d)_rS(O)_pNR_aR_a$, —$(CR_dR_d)_rNR_aS(O)_pR_c$, —$(CR_dR_d)_rOR_b$, —$(CR_dR_d)_rCN$, —$(CR_dR_d)_rNR_aR_a$, —$(CR_dR_d)_rNR_aC(=O)R_b$, —$(CR_dR_d)_rNR_aC(=O)NR_aR_a$, —$(CR_dR_d)_rNR_aC(=O)OR_b$, —$(CR_dR_d)_r C(=O)OR_b$, —$(CR_dR_d)_rC(=O)NR_aR_a$, —$(CR_dR_d)_r C(=O)R_b$, —$(CR_dR_d)_rOC(=O)R_b$, —$(CR_dR_d)_rOC(=O)NR_aR_a$, —$(CR_dR_d)_r$-cycloalkyl, —$(CR_dR_d)_r$-heterocyclyl, —$(CR_dR_d)_r$-aryl, and —$(CR_dR_d)_r$-heteroaryl, wherein said alkyl, cycloalkyl, heterocyclyl, aryl, or heteroaryl is substituted with 0-4 $R_e$;

$R_7$ is independently selected from H, F, Cl, Br, CN, $C_{1-4}$ alkyl substituted with 0-3 $R_e$, —$(CH_2)_rOR_b$;

$R_8$ is independently selected from H, F, Cl, Br, and —$(CH_2)_rOR_b$;

$R_9$ is independently selected from H and $C_{1-4}$alkyl substituted with 0-4 $R_e$;

$R_a$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$ is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$ is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, —$(CH_2)_r$-aryl, —$(CH_2)_r$-heteroaryl, F, Cl, Br, CN, $NO_2$, =O, $CO_2H$, —$(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)OR_d$, $OC(=O)NR_fR_f$, and —$(CH_2)_rNR_fR_f$;

$R_f$ is independently selected from H, F, Cl, Br, CN, OH, $C_{1-5}$alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

n, at each occurrence, is independently selected from 0, 1, and 2;

p, at each occurrence, is independently selected from 0, 1, and 2; and r is independently selected from 0, 1, 2, 3, and 4.

3. The compound of claim 1, having Formula (III):

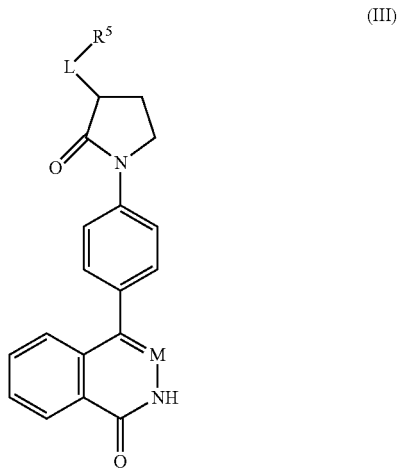

(III)

or a stereoisomer, a tautomer, or a pharmaceutically acceptable salt thereof, wherein:

L is absent or independently from —$NR_4$—, —$C(O)NR_4$ $(CR_4R_4)_n$—, and —O—;

M is independently selected from N and CH;

$R_4$ is independently selected from H and $C_{1-4}$alkyl substituted with 0-4 $R_e$;

$R_5$ is independently selected from $C_{3-6}$ cycloalkyl, heterocyclyl, aryl and heteroaryl, each substituted with 1-5 $R_6$;

alternatively, when L is —$NR_4$—, —$C(O)NR_4$—, $R_4$ and $R_5$ together with the nitrogen atom to which they are both attached form a heterocyclic ring substituted with 1-5 $R_6$;

$R_6$ is independently selected from H, =O, F, Cl, Br, $C_{1-4}$alkyl, $C_{2-4}$alkenyl, $C_{2-4}$alkynyl, nitro, —$(CR_dR_d)_rS(O)_pR_c$, —$(CR_dR_d)_rS(O)_pNR_aR_a$, —$(CR_dR_d)_rNR_aS(O)_pR_c$, —$(CR_dR_d)_rOR_b$, —$(CR_dR_d)_rCN$, —$(CR_dR_d)_rNR_aR_a$, —$(CR_dR_d)_rNR_aC(=O)R_b$, —$(CR_dR_d)_rNR_aC(=O)NR_aR_a$, —$(CR_dR_d)_rNR_aC(=O)OR_b$, —$(CR_dR_d)_r C(=O)OR_b$, —$(CR_dR_d)_rC(=O)NR_aR_a$, —$(CR_dR_d)_r C(=O)R_b$, —$(CR_dR_d)_rOC(=O)R_b$, —$(CR_dR_d)_rOC(=O)NR_aR_a$, —$(CR_dR_d)_r$-cycloalkyl, —$(CR_dR_d)_r$-heterocyclyl, —$(CR_dR_d)_r$-aryl, and —$(CR_dR_d)_r$-heteroaryl, wherein said alkyl, cycloalkyl, heterocyclyl, aryl, or heteroaryl is substituted with 0-4 $R_e$;

$R_a$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$;

$R_c$ is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$ is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, —$(CH_2)_r$-aryl, —$(CH_2)_r$-heteroaryl, F, Cl, Br, CN, $NO_2$, =O, $CO_2H$, —$(CH_2)_r OR_f$, $S(O)_p R_f$, $C(=O)NR_f R_f$, $NR_f C(=O)R_d$, $S(O)_p NR_f R_f$, $NR_f S(O)_p R_d$, $NR_f C(=O)OR_d$, $OC(=O)NR_f R_f$ and —$(CH_2)_r NR_f R_f$;

$R_f$ is independently selected from H, F, Cl, Br, CN, OH, $C_{1-5}$alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from 0, 1, and 2; and r is independently selected from 0, 1, 2, 3, and 4.

4. The compound of claim 3 or a stereoisomer, a tautomer, or a pharmaceutically acceptable salt thereof, wherein:

L is independently selected from —$NR_4$—, —$C(O)NR_4$ $(CH_2)_{0-1}$—, and —O—;

$R_4$ is independently selected from H and $C_{1-4}$alkyl substituted with 0-4 $R_e$;

$R_5$ is independently selected from

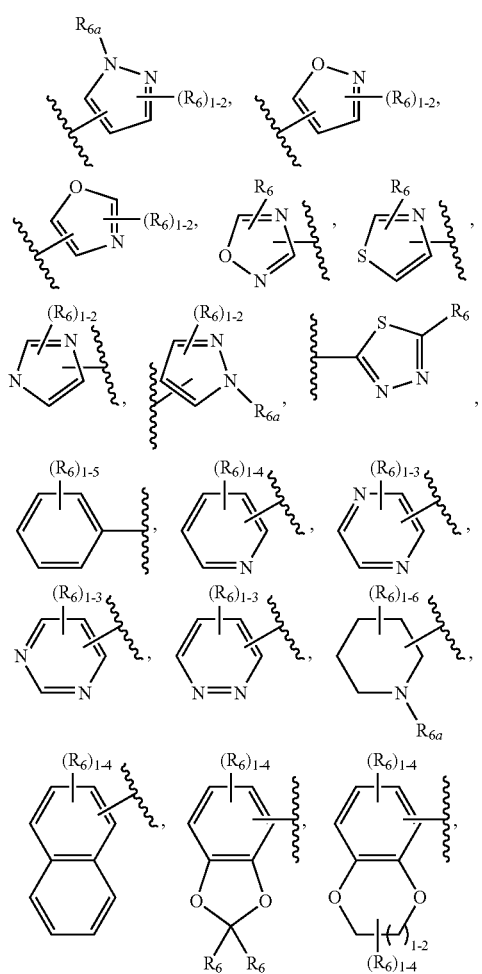

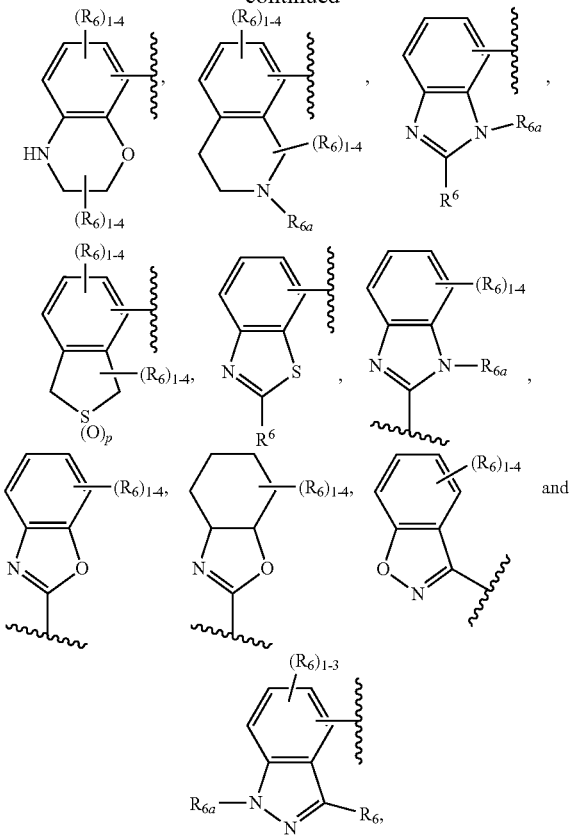

$R_6$ is independently selected from H, =O, F, Cl, Br, $C_{1-4}$alkyl, $C_{2-4}$alkenyl, $C_{2-4}$alkynyl, nitro, —$(CHR_d)_r S(O)_p R_c$, —$(CHR_d)_r S(O)_p NR_a R_a$, —$(CHR_d)_r NR_a S(O)_p R_c$, —$(CHR_d)_r OR_b$, —$(CHR_d)_r CN$, —$(CHR_d)_r NR_a R_a$, —$(CHR_d)_r NR_a C(=O)R_b$, —$(CHR_d)_r NR_a C(=O)NR_a R_a$, —$(CHR_d)_r NR_a C(=O)OR_b$, —$(CHR_d)_r C(=O)OR_b$, —$(CHR_d)_r C(=O)NR_a R_a$, —$(CHR_d)_r OC(=O)NR_a R_a$, —$(CHR_d)_r C(=O)R_b$, —$(CHR_d)_r OC(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_{6a}$ is independently selected from H, $C_{1-4}$ alkyl, —$S(O)_p R_c$, —$S(O)_p NR_a R_a$, —$C(=O)OR_b$, —$(CH_2)_r C(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_r$ $OR_f$, $S(O)_pR_f$, $S(O)_pNR_fR_f$, and —$(CH_2)_r$ $NR_fR_f$;

$R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

5. The compound of claim 3, or a stereoisomer, a tautomer, or a pharmaceutically acceptable salt thereof, wherein:

L is independently selected from —$NR_4$— and —C(O) $NR_4$—;

$R_4$ and $R_5$ are taken together with the nitrogen atom to which they are attached to form a heterocycle selected from

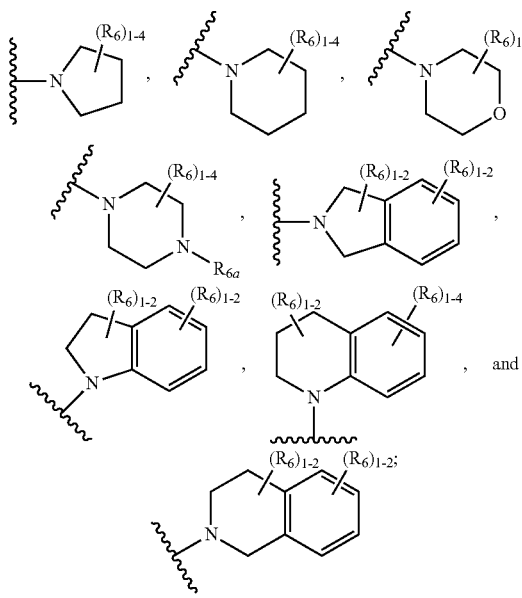

$R_6$ is independently selected from H, =O, F, Cl, Br, $C_{1-4}$alkyl, $C_{2-4}$alkenyl, $C_{2-4}$alkynyl, nitro, —$(CHR_d)_r$S $(O)_pR_c$, —$(CHR_d)_rS(O)_pNR_aR_a$, —$(CHR_d)_rNR_aS(O)_p$ $R_c$, —$(CHR_d)_rOR_b$, —$(CHR_d)_rCN$, —$(CHR_d)_rNR_a$ $R_a$, —$(CHR_d)_rNR_aC(=O)R_b$, —$(CHR_d)_rNR_aC(=O)$ $NR_aR_a$, —$(CHR_d)_rNR_aC(=O)OR_b$, —$(CHR_d)_rC$ $(=O)OR_b$, —$(CHR_d)_rC(=O)NR_aR_a$, —$(CHR_d)_rOC$ $(=O)NR_aR_a$, —$(CHR_d)_rC(=O)R_b$, —$(CHR_d)_rOC$ $(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_{6a}$ is independently selected from H, $C_{1-4}$ alkyl, —$S(O)_p$ $R_c$, —$S(O)_pNR_aR_a$, —$C(=O)OR_b$, —$(CH_2)_rC(=O)$ $R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_r$ $OR_f$, $S(O)_pR_f$, $S(O)_pNR_fR_f$, and —$(CH_2)_r$ $NR_fR_f$;

$R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

6. The compound of claim 3 or a stereoisomer, a tautomer, or a pharmaceutically acceptable salt thereof, wherein:

L is —O—;

$R_5$ is independently selected from

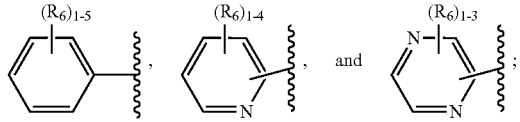

$R_6$ is independently selected from H, =O, F, Cl, Br, $C_{1-4}$alkyl, $C_{2-4}$alkenyl, $C_{2-4}$alkynyl, nitro, —$(CHR_d)_r$S $(O)_pR_c$, —$(CHR_d)_rS(O)_pNR_aR_a$, —$(CHR_d)_rNR_aS(O)_p$ $R_c$, —$(CHR_d)_rOR_b$, —$(CHR_d)_rCN$, —$(CHR_d)_rNR_a$ $R_a$, —$(CHR_d)_rNR_aC(=O)R_b$, —$(CHR_d)_rNR_aC(=O)$ $NR_aR_a$, —$(CHR_d)_rNR_aC(=O)OR_b$, —$(CHR_d)_rC$ $(=O)OR_b$, —$(CHR_d)_rC(=O)NR_aR_a$, —$(CHR_d)_rOC$ $(=O)NR_aR_a$, —$(CHR_d)_rC(=O)R_b$, —$(CHR_d)_rOC$ $(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_r$ $OR_f$, $S(O)_pR_f$, $S(O)_pNR_fR_f$, and —$(CH_2)_r$ $NR_fR_f$;

$R_f$, at each occurrence, is independently selected from H, F, Cl, Br, CN, OH, $C_{1-5}$ alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

7. The compound of claim 2, having Formula (IV):

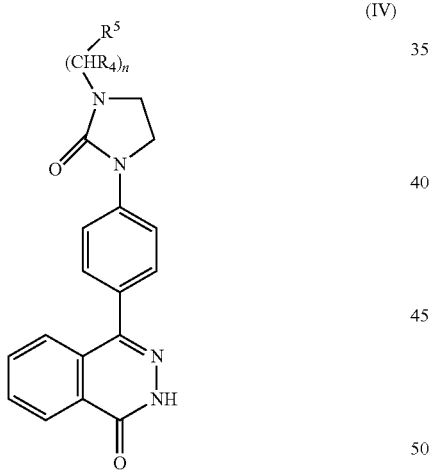

(IV)

or a stereoisomer, a tautomer, or a pharmaceutically acceptable salt thereof, wherein:

$R_4$ is independently selected from H and $C_{1-4}$alkyl substituted with 0-4 $R_e$;

$R_5$ is independently selected from $C_{3-6}$ cycloalkyl, heterocyclyl, aryl and heteroaryl, each substituted with 1-5 $R_6$;

$R_6$ is independently selected from H, =O, F, Cl, Br, $C_{1-4}$alkyl, $C_{2-4}$alkenyl, $C_{2-4}$alkynyl, nitro, —$(CR_dR_d)_r$ $S(O)_pR_c$, —$(CR_dR_d)_rS(O)_pNR_aR_a$, —$(CR_dR_d)_rNR_aS(O)_pR_c$, —$(CR_dR_d)_rOR_b$, —$(CR_dR_d)_rCN$, —$(CR_dR_d)_r NR_aR_a$, —$(CR_dR_d)_rNR_aC(=O)R_b$, —$(CR_dR_d)_rNR_aC(=O)NR_aR_a$, —$(CR_dR_d)_rNR_aC(=O)OR_b$, —$(CR_dR_d)_r$ $C(=O)OR_b$, —$(CR_dR_d)_rC(=O)NR_aR_a$, —$(CR_dR_d)_r$ $C(=O)R_b$, —$(CR_dR_d)_rOC(=O)R_b$, —$(CR_dR_d)_rOC(=O)NR_aR_a$, —$(CR_dR_d)_r$-cycloalkyl, —$(CR_dR_d)_r$-heterocyclyl, —$(CR_dR_d)_r$-aryl, and —$(CR_dR_d)_r$-heteroaryl, wherein said alkyl, cycloalkyl, heterocyclyl, aryl, or heteroaryl is substituted with 0-4 $R_e$;

$R_a$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$ is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$ is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$ is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, —$(CH_2)_r$-aryl, —$(CH_2)_r$-heteroaryl, F, Cl, Br, CN, $NO_2$, =O, $CO_2H$, —$(CH_2)_rOR_b$, $S(O)_pR_f$, $C(=O)NR_fR_f$, $NR_fC(=O)R_d$, $S(O)_pNR_fR_f$, $NR_fS(O)_pR_d$, $NR_fC(=O)OR_d$, $OC(=O)NR_fR_f$, and —$(CH_2)_rNR_fR_f$;

$R_f$ is independently selected from H, F, Cl, Br, CN, OH, $C_{1-5}$alkyl, $C_{3-6}$ cycloalkyl, and phenyl; or $R_f$ and $R_f$ together with the nitrogen atom to which they are both attached form a heterocyclic ring optionally substituted with $C_{1-4}$alkyl;

n, at each occurrence, is independently selected from 0 and 1;

p, at each occurrence, is independently selected from 0, 1, and 2; and r is independently selected from 0, 1, 2, 3, and 4.

8. The compound of claim 2, having Formula (V):

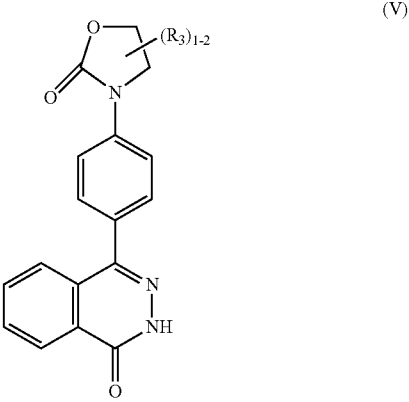

(V)

or a stereoisomer, a tautomer, or a pharmaceutically acceptable salt thereof, wherein:

$R_3$ is independently selected from H, $C_{1-4}$alkyl substituted with 0-4 $R_e$, —$(CH_2)_rOR_b$, $(CH_2)_rS(O)_pR_c$, —$(CH_2)_r$ $C(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS (O)$_p$NR$_a$R$_a$, —(CH$_2$)$_r$NR$_a$S(O)$_p$NR$_a$R$_a$, —(CH$_2$)$_r$N-R$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_a$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$ is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$ is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$ and —(CH$_2$)$_r$NR$_f$R$_f$;

R$_f$ is independently selected from H, F, Cl, Br, CN, OH, C$_{1-5}$alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

p, at each occurrence, is independently selected from 0, 1, and 2; and r is independently selected from 0, 1, 2, 3, and 4.

9. The compound of claim 1, having Formula (VI):

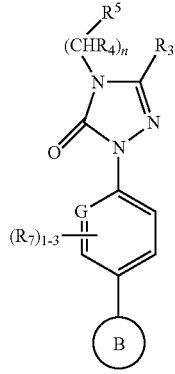

(VI)

or a stereoisomer, a tautomer, or a pharmaceutically acceptable salt thereof, wherein:

Ring B is selected from

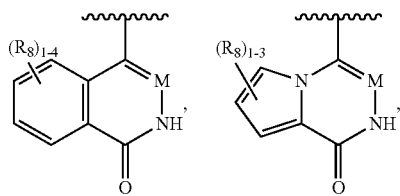

-continued

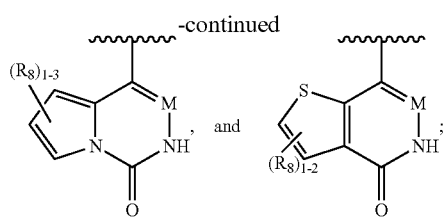

G is selected from N and CR$_7$;

M is independently selected from N and CR$_9$;

R$_3$ is independently selected from H, C$_{1-4}$alkyl substituted with 0-4 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_4$ is independently selected from H and C$_{1-4}$alkyl substituted with 0-4 R$_e$;

R$_5$ is independently selected from C$_{3-6}$ cycloalkyl, heterocyclyl, aryl and heteroaryl, each substituted with 1-5 R$_6$;

R$_6$ is independently selected from H, =O, F, Cl, Br, C$_{1-4}$alkyl, C$_{2-4}$alkenyl, C$_{2-4}$alkynyl, nitro, —(CR$_d$R$_d$)$_r$S(O)$_p$R$_c$, —(CR$_d$R$_d$)$_r$S(O)$_p$NR$_a$R$_a$, —(CR$_d$R$_d$)$_r$NR$_a$S(O)$_p$R$_c$, —(CR$_d$R$_d$)$_r$OR$_b$, —(CR$_d$R$_d$)$_r$CN, —(CR$_d$R$_d$)$_r$NR$_a$R$_a$, —(CR$_d$R$_d$)$_r$NR$_a$C(=O)R$_b$, —(CR$_d$R$_d$)$_r$NR$_a$C(=O)NR$_a$R$_a$, —(CR$_d$R$_d$)$_r$NR$_a$C(=O)OR$_b$, —(CR$_d$R$_d$)$_r$C(=O)OR$_b$, —(CR$_d$R$_d$)$_r$C(=O)NR$_a$R$_a$, —(CR$_d$R$_d$)$_r$C(=O)R$_b$, —(CR$_d$R$_d$)$_r$OC(=O)R$_b$, —(CR$_d$R$_d$)$_r$OC(=O)NR$_a$R$_a$, —(CR$_d$R$_d$)$_r$-cycloalkyl, —(CR$_d$R$_d$)$_r$-heterocyclyl, —(CR$_d$R$_d$)$_r$-aryl, and —(CR$_d$R$_d$)$_r$-heteroaryl, wherein said alkyl, cycloalkyl, heterocyclyl, aryl, or heteroaryl is substituted with 0-4 R$_e$;

R$_7$ is independently selected from H, F, Cl, Br, CN, C$_{1-4}$ alkyl substituted with 0-3 R$_e$, —(CH$_2$)$_r$OR$_b$;

R$_8$ is independently selected from H, F, Cl, Br, and —(CH$_2$)$_r$OR$_b$;

R$_9$ is independently selected from H and C$_{1-4}$alkyl substituted with 0-4 R$_e$;

R$_a$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$ is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$ is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C (=O)R$_d$, S(O)$_p$NR$_f$R$_f$, NR$_f$S(O)$_p$R$_d$, NR$_f$C(=O)OR$_d$, OC(=O)NR$_f$R$_f$ and —(CH$_2$)$_r$NR$_f$R$_f$;

R$_f$ is independently selected from H, F, Cl, Br, CN, OH, C$_{1-5}$alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

n, at each occurrence, is independently selected from 0 and 1;

p, at each occurrence, is independently selected from 0, 1, and 2; and r is independently selected from 0, 1, 2, 3, and 4.

10. The compound of claim 1, having Formula (VII):

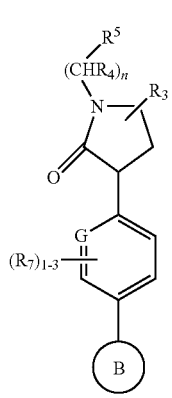

(VII)

or a stereoisomer, a tautomer, or a pharmaceutically acceptable salt thereof, wherein:

Ring B is selected from

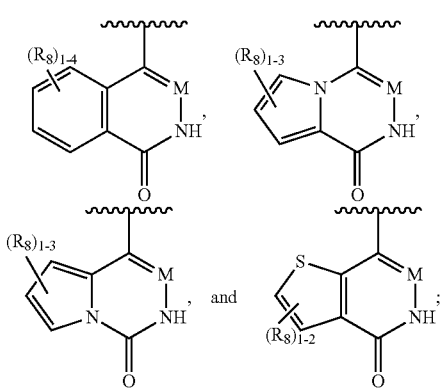

and

G is selected from N and CR$_7$;

M is independently selected from N and CR$_9$;

R$_3$ is independently selected from H, C$_{1-4}$alkyl substituted with 0-4 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_4$ is independently selected from H and C$_{1-4}$alkyl substituted with 0-4 R$_e$;

R$_5$ is independently selected from C$_{3-6}$ cycloalkyl, heterocyclyl, aryl and heteroaryl, each substituted with 1-5 R$_6$;

R$_6$ is independently selected from H, =O, F, Cl, Br, C$_{1-4}$alkyl, C$_{2-4}$alkenyl, C$_{2-4}$alkynyl, nitro, —(CR$_d$R$_d$)$_r$S(O)$_p$R$_c$, —(CR$_d$R$_d$)$_r$S(O)$_p$NR$_a$R$_a$, —(CR$_d$R$_d$)$_r$NR$_a$S(O)$_p$R$_c$, —(CR$_d$R$_d$)$_r$OR$_b$, —(CR$_d$R$_d$)$_r$CN, —(CR$_d$R$_d$)$_r$NR$_a$R$_a$, —(CR$_d$R$_d$)$_r$NR$_a$C(=O)R$_b$, —(CR$_d$R$_d$)$_r$NR$_a$C(=O)NR$_a$R$_a$, —(CR$_d$R$_d$)$_r$NR$_a$C(=O)OR$_b$, —(CR$_d$R$_d$)$_r$C(=O)OR$_b$, —(CR$_d$R$_d$)$_r$C(=O)NR$_a$R$_a$, —(CR$_d$R$_d$)$_r$C(=O)R$_b$, —(CR$_d$R$_d$)$_r$OC(=O)R$_b$, —(CR$_d$R$_d$)$_r$OC(=O)NR$_a$R$_a$, —(CR$_d$R$_d$)$_r$-cycloalkyl, —(CR$_d$R$_d$)$_r$-heterocyclyl, —(CR$_d$R$_d$)$_r$-aryl, and —(CR$_d$R$_d$)$_r$-heteroaryl, wherein said alkyl, cycloalkyl, heterocyclyl, aryl, or heteroaryl is substituted with 0-4 R$_e$;

R$_7$ is independently selected from H, F, Cl, Br, CN, C$_{1-4}$ alkyl substituted with 0-3 R$_e$, —(CH$_2$)$_r$OR$_b$;

R$_8$ is independently selected from H, F, Cl, Br, and —(CH$_2$)$_r$OR$_b$;

R$_9$ is independently selected from H and C$_{1-4}$alkyl substituted with 0-4 R$_e$;

R$_a$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$ is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$ carbocyclyl substituted with 0-5 R$_e$, and —(CH$_2$)$_r$-heterocyclyl substituted with 0-5 R$_e$;

R$_c$ is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$ is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$ and —(CH$_2$)$_r$NR$_f$R$_f$;

R$_f$ is independently selected from H, F, Cl, Br, CN, OH, C$_{1-5}$alkyl, C$_{3-6}$ cycloalkyl, and phenyl; or R$_f$ and R$_f$ together with the nitrogen atom to which they are both attached form a heterocyclic ring optionally substituted with C$_{1-4}$alkyl;

n, at each occurrence, is independently selected from 0 and 1;

p, at each occurrence, is independently selected from 0, 1, and 2; and r is independently selected from 0, 1, 2, 3, and 4.

11. A pharmaceutical composition comprising one or more compounds according to claim 1 and a pharmaceutically acceptable carrier or diluent.

12. A method for the treatment of, a cardiovascular disorder, a smooth muscle related disorder, a fibrotic disease, an inflammatory disease, neuropathic disorders, oncologic disorders, and an autoimmune disorder, comprising administering to a patient in need thereof a therapeutically effective amount of at least one compound of claim 1.

13. The method of claim 12, wherein said cardiovascular disorder is selected from the group consisting of angina, atherosclerosis, stroke, cerebrovascular disease, heart failure, coronary artery disease, myocardial infarction, peripheral vascular disease, stenosis, vasospasm, hypertension and pulmonary hypertension.

14. The compound of claim 1, which is selected from:
4-[4-(2-oxo-3-phenylpyrrolidin-1-yl)phenyl]-1,2-dihydrophthalazin-1-one;
4-[4-(2-oxo-3-phenylimidazolidin-1-yl)phenyl]-1,2-dihydrophthalazin-1-one trifluoroacetic acid salt;
4-{4-[3-(2,3-dihydro-1H-indole-1-carbonyl)-2-oxopyrrolidin-1-yl]phenyl}-1,2-dihydrophthalazin-1-one;
4-[4-(2-oxo-4-phenylpyrrolidin-1-yl)phenyl]-1,2-dihydrophthalazin-1-one;
4-{4-[3-(2,3-dihydro-1H-isoindole-2-carbonyl)-2-oxopyrrolidin-1-yl]phenyl}-1,2-dihydrophthalazin-1-one trifluoroacetic acid salt;
2-oxo-1-[4-(4-oxo-3,4-dihydrophthalazin-1-yl)phenyl]-N-phenylpyrrolidine-3-carboxamide;
N-benzyl-2-oxo-1-[4-(4-oxo-3,4-dihydrophthalazin-1-yl)phenyl]pyrrolidine-3-carboxamide;
8: 4-[4-(1-benzyl-2-oxopyrrolidin-3-yl)phenyl]-1,2-dihydrophthalazin-1-one;
4-[4-(2-oxo-1-phenylpyrrolidin-3-yl)phenyl]-1,2-dihydrophthalazin-1-one;
4-[4-(3-benzyl-2-oxoimidazolidin-1-yl)phenyl]-1,2-dihydrophthalazin-1-one;
4-{4-[2-oxo-3-(pyridin-3-yl)imidazolidin-1-yl]phenyl}-1,2-dihydrophthalazin-1-one;
4-{4-[2-oxo-3-(pyridin-2-yl)imidazolidin-1-yl]phenyl}-1,2-dihydrophthalazin-1-one; trifluoroacetic acid salt;
4-[4-(5-benzyl-2-oxo-1,3-oxazolidin-3-yl)phenyl]-1,2-dihydrophthalazin-1-one; trifluoroacetic acid salt;
4-[4-(2-oxo-4-phenyl-1,3-oxazolidin-3-yl)phenyl]-1,2-dihydrophthalazin-1-one;
4-[4-(2-oxo-5-phenyl-1,3-oxazolidin-3-yl)phenyl]-1,2-dihydrophthalazin-1-one;
tert-butyl N-({2-oxo-3-[4-(4-oxo-3,4-dihydrophthalazin-1-yl)phenyl]-1,3-oxazolidin-5-yl}methyl)carbamate;
4-[4-(2-oxo-5-propyl-1,3-oxazolidin-3-yl)phenyl]-1,2-dihydrophthalazin-1-one;
N-({2-oxo-3-[4-(4-oxo-3,4-dihydrophthalazin-1-yl)phenyl]-1,3-oxazolidin-5-yl}methyl)benzamide;
4-{4-[5-(4-fluorophenyl)-2-oxo-1,3-oxazolidin-3-yl]phenyl}-1,2-dihydrophthalazin-1-one;
4-(4-{5-[(4-methanesulfonylphenyl)methyl]-2-oxo-1,3-oxazolidin-3-yl}phenyl)-1,2-dihydrophthalazin-1-one;
4-[4-(2-oxo-octahydro-1,3-benzoxazol-3-yl)phenyl]-1,2-dihydrophthalazin-1-one;
4-{4-[2-oxo-5-(2,2,2-trifluoro-1-hydroxy-1-phenylethyl)-1,3-oxazolidin-3-yl]phenyl}-1,2-dihydrophthalazin-1-one;
4-{4-[(4R,5 S)-5-methyl-2-oxo-4-phenyl-1,3-oxazolidin-3-yl]phenyl}-1,2-dihydrophthalazin-1-one;
4-{4-[3-(morpholin-4-yl)-2-oxopyrrolidin-1-yl]phenyl}-1,2-dihydrophthalazin-1-one;
4-{4-[3-(benzylamino)-2-oxopyrrolidin-1-yl]phenyl}-1,2-dihydrophthalazin-1-one; trifluoroacetic acid salt;
4-(4-{3-[(3-methoxyphenyl)amino]-2-oxopyrrolidin-1-yl}phenyl)-1,2-dihydrophthalazin-1-one;
4-{4-[2-oxo-3-(phenylamino)pyrrolidin-1-yl]phenyl}-1,2-dihydrophthalazin-1-one trifluoroacetic acid salt;
4-{4-[3-(cyclopentylamino)-2-oxopyrrolidin-1-yl]phenyl-1,2-dihydrophthalazin-1-one trifluoroacetic acid salt;
4-(4-{3-[(2,3-dihydro-1H-inden-2-yl)amino]-2-oxopyrrolidin-1-yl}phenyl)-1,2-dihydrophthalazin-1-one;
4-[4-(3-{[3-(difluoromethoxy)phenyl]amino}-2-oxopyrrolidin-1-yl)phenyl]-1,2-dihydrophthalazin-1-one;
4-(4-{3-[(2-ethylphenyl)amino]-2-oxopyrrolidin-1-yl}phenyl)-1,2-dihydrophthalazin-1-one;
4-(4-{3-[(3-fluoro-5-methoxyphenyl)amino]-2-oxopyrrolidin-1-yl}phenyl)-1,2-dihydrophthalazin-1-one;
4-(4-{3-[(2H-1,3-benzodioxol-5-yl)amino]-2-oxopyrrolidin-1-yl}phenyl)-1,2-dihydrophthalazin-1-one;
4-(4-{3-[(3,4-dihydro-2H-1,5-benzodioxepin-7-yl)amino]-2-oxopyrrolidin-1-yl}phenyl)-1,2-dihydrophthalazin-1-one;
4-(4-{3-[(3-cyclopropyl-1-methyl-1H-pyrazol-5-yl)amino]-2-oxopyrrolidin-1-yl}phenyl)-1,2-dihydrophthalazin-1-one;
4-(4-{3-[(3-cyclopropyl-5-methyl-1H-pyrazol-4-yl)amino]-2-oxopyrrolidin-1-yl}phenyl)-1,2-dihydrophthalazin-1-one;
4-(4-{3-[(2-fluoro-5-methoxyphenyl)amino]-2-oxopyrrolidin-1-yl}phenyl)-1,2-dihydrophthalazin-1-one;
4-(4-{3-[(3-methoxy-5-methylphenyl)amino]-2-oxopyrrolidin-1-yl}phenyl)-1,2-dihydrophthalazin-1-one trifluoroacetic acid salt;
4-(4-{2-oxo-3-[(1-phenyl-1H-pyrazol-4-yl)amino]pyrrolidin-1-yl}phenyl)-1,2-dihydrophthalazin-1-one;
4-(4-{3-[(2,4-difluoro-3-methoxyphenyl)amino]-2-oxopyrrolidin-1-yl}phenyl)-1,2-dihydrophthalazin-1-one;
4-[4-(4-benzyl-5-oxo-4,5-dihydro-1H-1,2,4-triazol-1-yl)phenyl]-1,2-dihydrophthalazin-1-one trifluoroacetic acid salt;
4-(4-{3-[(4-fluoro-3-methoxyphenyl)amino]-2-oxopyrrolidin-1-yl}phenyl)-1,2-dihydrophthalazin-1-one;
4-(4-{3-[(3-ethoxyphenyl)amino]-2-oxopyrrolidin-1-yl}phenyl)-1,2-dihydrophthalazin-1-one;
4-[4-(3-{[(1R)-1-(3-methoxyphenyl)ethyl]amino}-2-oxopyrrolidin-1-yl)phenyl]-1,2-dihydrophthalazin-1-one;
4-(4-{2-oxo-3-[(2-phenylethyl)amino]pyrrolidin-1-yl}phenyl)-1,2-dihydrophthalazin-1-one;
4-(4-{4-[(3-methoxyphenyl)methyl]-5-oxo-4,5-dihydro-1H-1,2,4-triazol-1-yl}phenyl)-1,2-dihydrophthalazin-1-one;
4-benzyl-1-(4-{4-oxo-3H,4H-pyrrolo[1,2-d][1,2,4]triazin-1-yl)}phenyl)-4,5-dihydro-1H-1,2,4-triazol-5-one;
4-[4-(3-{[3-methoxy-4-(4-methylpiperazin-1-yl)phenyl]amino}-2-oxopyrrolidin-1-yl)phenyl]-1,2-dihydrophthalazin-1-one;
4-[4-(3-{[3-methoxy-4-(morpholin-4-yl)phenyl]amino}-2-oxopyrrolidin-1-yl)phenyl]-1,2-dihydrophthalazin-1-one;
4-(4-{3-[(2,3-dihydro-1,4-benzodioxin-6-yl)amino]-2-oxopyrrolidin-1-yl}phenyl)-1,2-dihydrophthalazin-1-one;
4-(4-{3-[(2,2-difluoro-2H-1,3-benzodioxol-5-yl)amino]-2-oxopyrrolidin-1-yl}phenyl)-1,2-dihydrophthalazin-1-one;
4-[4-(2-oxo-3-{[3-(trifluoromethoxy)phenyl]amino}pyrrolidin-1-yl)phenyl]-1,2-dihydrophthalazin-1-one;
4-(4-{4-[(3-fluorophenyl)methyl]-5-oxo-4,5-dihydro-1H-1,2,4-triazol-1-yl}phenyl)-1,2-dihydrophthalazin-1-one;
4-{4-[5-oxo-4-(1-phenylethyl)-4,5-dihydro-1H-1,2,4-triazol-1-yl]phenyl}-1,2-dihydrophthalazin-1-one;
4-[4-(3-{[3-(difluoromethoxy)phenyl]amino}-2-oxopyrrolidin-1-yl)phenyl]-1,2-dihydrophthalazin-1-one;
4-[4-(2-oxo-3-{[3-(propan-2-yloxy)phenyl]amino}pyrrolidin-1-yl)phenyl]-1,2-dihydrophthalazin-1-one;
4-[4-(3-{[3-(difluoromethoxy)phenyl]amino}-2-oxopyrrolidin-1-yl)phenyl]-1,2-dihydroisoquinolin-1-one;

2-({2-oxo-1-[4-(4-oxo-3,4-dihydrophthalazin-1-yl)phenyl]pyrrolidin-3-yl)}amino)-1,3-thiazole-5-carbonitrile;

4-[4-(3-{[4-(difluoromethoxy)phenyl]amino}-2-oxopyrrolidin-1-yl)phenyl]-1,2-dihydrophthalazin-1-one trifluoroacetic acid salt;

4-(4-{3-[(2-methoxyphenyl)amino]-2-oxopyrrolidin-1-yl}phenyl)-1,2-dihydrophthalazin-1-one trifluoroacetic acid salt;

7-({2-oxo-1-[4-(4-oxo-3,4-dihydrophthalazin-1-yl)phenyl]pyrrolidin-3-yl}amino)-3,4-dihydro-2H-1,4-benzoxazin-3-one;

4-[4-(4-{[3-(difluoromethoxy)phenyl]methyl}-5-oxo-4,5-dihydro-1H-1,2,4-triazol-1-yl)phenyl]-1,2-dihydrophthalazin-1-one;

4-[4-(2-oxo-3-{[1-(propan-2-yl)-1H-pyrazol-3-yl]amino}pyrrolidin-1-yl)phenyl]-1,2-dihydrophthalazin-1-one;

4-(4-{3-[(1-methyl-1H-pyrazol-3-yl)amino]-2-oxopyrrolidin-1-yl}phenyl)-1,2-dihydrophthalazin-1-one;

4-(4-{3-[(2-methyl-1,3-benzothiazol-6-yl)amino]-2-oxopyrrolidin-1-yl)}phenyl)-1,2-dihydrophthalazin-1-one;

4-(4-{3-[(3-methanesulfonylphenyl)amino]-2-oxopyrrolidin-1-yl)}phenyl)-1,2-dihydrophthalazin-1-one trifluoroacetic acid salt;

4-[4-(3-{[3-(methyl sulfanyl)phenyl]amino}-2-oxopyrrolidin-1-yl)phenyl]-1,2-dihydrophthalazin-1-one;

4-(4-{3-[(6-fluoropyridin-2-yl)amino]-2-oxopyrrolidin-1-yl)}phenyl)-1,2-dihydrophthalazin-1-one;

4-(4-{2-oxo-3-[(1,2,3,4-tetrahydroisoquinolin-6-yl)amino]pyrrolidin-1-yl}phenyl)-1,2-dihydrophthalazin-1-one;

4-[4-(3-{[1-methyl-3-(propan-2-yl)-1H-pyrazol-5-yl]amino}-2-oxopyrrolidin-1-yl)phenyl]-1,2-dihydrophthalazin-1-one trifluoroacetic acid salt;

4-[(3-methoxyphenyl)methyl]-3-methyl-1-(4-{4-oxo-3aH,4H,5H,7aH-thieno[3,2-c]pyridin-7-yl}phenyl)-4,5-dihydro-1H-1,2,4-triazol-5-one trifluoroacetic acid salt;

4-(4-{2-oxo-3-[3-(trifluoromethoxy)phenoxy]pyrrolidin-1-yl}phenyl)-1,2-dihydrophthalazin-1-one;

2-({2-oxo-1-[4-(4-oxo-3,4-dihydrophthalazin-1-yl)phenyl]pyrrolidin-3-yl}amino)pyridine-4-carbonitrile trifluoroacetic acid salt;

4-(4-{3-[(2-methyl-1,2,3,4-tetrahydroisoquinolin-6-yl)amino]-2-oxopyrrolidin-1-yl)}phenyl)-1,2-dihydrophthalazin-1-one;

4-(4-{3-[(3,4-dihydro-2H-1,5-benzodioxepin-7-yl)amino]-2-oxopyrrolidin-1-yl}phenyl)-1,2-dihydrophthalazin-1-one;

4-[4-(3-{[3-(difluoromethoxy)phenyl]amino}-2-oxopyrrolidin-1-yl)phenyl]-1,2-dihydroisoquinolin-1-one;

4-(4-{3-[(2-methyl-1,3-benzothiazol-6-yl)amino]-2-oxopyrrolidin-1-yl)}phenyl)-1,2-dihydrophthalazin-1-one;

7-({2-oxo-1-[4-(4-oxo-3,4-dihydrophthalazin-1-yl)phenyl]pyrrolidin-3-yl}amino)-3,4-dihydro-2H-1,4-benzoxazin-3-one;

4-(4-{2-oxo-3-[3-(trifluoromethoxy)phenoxy]pyrrolidin-1-yl}phenyl)-1,2-dihydrophthalazin-1-one;

4-{4-[3-(3-methoxyphenoxy)-2-oxopyrrolidin-1-yl]phenyl}-1,2-dihydrophthalazin-1-one trifluoroacetic acid salt;

4-{4-[3-(2-fluoro-5-methoxyphenoxy)-2-oxopyrrolidin-1-yl]phenyl}-1,2-dihydrophthalazin-1-one;

4-{4-[3-(4-fluoro-3-methoxyphenoxy)-2-oxopyrrolidin-1-yl]phenyl}-1,2-dihydrophthalazin-1-one; and 4-{4-[3-(3-fluoro-5-methoxyphenoxy)-2-oxopyrrolidin-1-yl]phenyl}-1,2-dihydrophthalazin-1-one.

\* \* \* \* \*